United States Patent
Tarinelli et al.

(10) Patent No.: US 8,231,043 B2
(45) Date of Patent: Jul. 31, 2012

(54) SURGICAL STAPLING APPARATUS

(75) Inventors: Danyel Tarinelli, Middletown, CT (US); Ernie Aranyi, Easton, CT (US); Richard Simpson, Hamden, CT (US); Sachin Shah, Milford, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/197,252

(22) Filed: Aug. 3, 2011

(65) Prior Publication Data

US 2011/0284615 A1 Nov. 24, 2011

Related U.S. Application Data

(63) Continuation of application No. 12/342,400, filed on Dec. 23, 2008, now Pat. No. 8,011,555, which is a continuation-in-part of application No. 12/528,526, filed as application No. PCT/US2008/002981 on Mar. 5, 2008.

(60) Provisional application No. 60/905,566, filed on Mar. 6, 2007.

(51) Int. Cl.
*A61B 17/068* (2006.01)
(52) U.S. Cl. ............ 227/180.1; 227/19; 227/175.1; 227/176.1
(58) Field of Classification Search ............ 227/176.1, 227/19, 175.1, 180.1
See application file for complete search history.

(56) References Cited

U.S. PATENT DOCUMENTS

| | | | |
|---|---|---|---|
| 3,054,406 A | 9/1962 | Usher | |
| 3,124,136 A | 3/1964 | Usher | |
| 4,347,847 A | 9/1982 | Usher | |
| 4,354,628 A | 10/1982 | Green | |
| 4,452,245 A | 6/1984 | Usher | |
| 4,605,730 A | 8/1986 | Shalaby et al. | |
| 4,655,221 A | 4/1987 | Devereux | |
| 4,834,090 A | 5/1989 | Moore | |
| 4,838,884 A | 6/1989 | Dumican et al. | |
| 4,930,674 A | 6/1990 | Barak | |
| 5,002,551 A | 3/1991 | Linsky et al. | |

(Continued)

FOREIGN PATENT DOCUMENTS

DE 1 99 24 311 A1 11/2000

(Continued)

OTHER PUBLICATIONS

International Search Report corresponding to European Application No. EP 06 00 4598, completed on Jun. 22, 2006; 2 pages.

(Continued)

*Primary Examiner* — Brian D Nash

(57) ABSTRACT

A surgical stapling apparatus is provided and includes a cartridge assembly defining a tissue contacting surface and a longitudinally extending elongate slot, an anvil assembly defining a tissue contacting surface, and a longitudinally extending elongate slot. A surgical buttress is releasably secured to at least one of the tissue contacting surface of the cartridge assembly and the tissue contacting surface of the anvil assembly by at least one anchor. A central knife blade is slidably disposable in the longitudinal extending elongate slot of the cartridge assembly and the anvil assembly, and a knife blade is supported in a distal end portion of at least one of the cartridge assembly and the anvil assembly. The distal knife blade is actuatable by the central knife blade upon an actuation of the central knife blade.

20 Claims, 76 Drawing Sheets

U.S. PATENT DOCUMENTS

| | | |
|---|---|---|
| 5,014,899 A | 5/1991 | Presty et al. |
| 5,040,715 A | 8/1991 | Green et al. |
| 5,065,929 A | 11/1991 | Schulze et al. |
| 5,205,459 A | 4/1993 | Brinkerhoff et al. |
| 5,263,629 A | 11/1993 | Trumbull et al. |
| 5,314,471 A | 5/1994 | Brauker et al. |
| 5,344,454 A | 9/1994 | Clarke et al. |
| 5,392,979 A | 2/1995 | Green et al. |
| 5,397,324 A | 3/1995 | Carroll et al. |
| 5,425,745 A | 6/1995 | Green et al. |
| 5,441,193 A | 8/1995 | Gravener |
| 5,441,507 A | 8/1995 | Wilk et al. |
| 5,468,253 A | 11/1995 | Bezwada et al. |
| 5,503,638 A | 4/1996 | Cooper et al. |
| 5,542,594 A | 8/1996 | McKean et al. |
| 5,549,628 A | 8/1996 | Cooper et al. |
| 5,575,803 A | 11/1996 | Cooper et al. |
| 5,653,756 A | 8/1997 | Clarke et al. |
| 5,683,809 A | 11/1997 | Freeman et al. |
| 5,690,675 A | 11/1997 | Sawyer et al. |
| 5,702,409 A | 12/1997 | Rayburn et al. |
| 5,752,965 A | 5/1998 | Francis et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,833,695 A | 11/1998 | Yoon |
| 5,843,096 A | 12/1998 | Igaki et al. |
| 5,895,412 A | 4/1999 | Tucker |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,019,791 A | 2/2000 | Wood |
| 6,030,392 A | 2/2000 | Dakov et al. |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,099,551 A | 8/2000 | Gabbay |
| 6,149,667 A | 11/2000 | Hovland et al. |
| 6,155,265 A | 12/2000 | Hammerslag |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,436,030 B2 | 8/2002 | Rehil |
| 6,454,780 B1 | 9/2002 | Wallace |
| 6,461,368 B2 | 10/2002 | Fogarty et al. |
| 6,503,257 B2 | 1/2003 | Grant et al. |
| 6,514,283 B2 | 2/2003 | DiMatteo et al. |
| 6,517,566 B1 | 2/2003 | Hovland et al. |
| 6,551,356 B2 | 4/2003 | Rousseau |
| 6,592,597 B2 | 7/2003 | Grant et al. |
| 6,638,285 B2 | 10/2003 | Gabbay |
| 6,652,594 B2 | 11/2003 | Francis et al. |
| 6,656,193 B2 | 12/2003 | Grant et al. |
| 6,669,735 B1 | 12/2003 | Pelissier |
| 6,677,258 B2 | 1/2004 | Carroll et al. |
| 6,685,714 B2 | 2/2004 | Rousseau |
| 6,704,210 B1 | 3/2004 | Myers |
| 6,723,114 B2 | 4/2004 | Shalaby |
| 6,726,706 B2 | 4/2004 | Dominguez |
| 6,736,823 B2 | 5/2004 | Darois et al. |
| 6,736,854 B2 | 5/2004 | Vadurro et al. |
| 6,746,458 B1 | 6/2004 | Cloud |
| 6,773,458 B1 | 8/2004 | Brauker et al. |
| 6,927,315 B1 | 8/2005 | Heinecke et al. |
| 7,044,353 B2 * | 5/2006 | Mastri et al. ............... 227/176.1 |
| 7,128,748 B2 | 10/2006 | Mooradian et al. |
| 7,147,138 B2 | 12/2006 | Shelton, IV |
| 7,434,717 B2 | 10/2008 | Shelton, IV et al. |
| 7,438,209 B1 | 10/2008 | Hess et al. |
| 7,547,312 B2 | 6/2009 | Bauman et al. |
| 7,559,937 B2 | 7/2009 | de la Torre et al. |
| 7,604,151 B2 | 10/2009 | Hess et al. |
| 7,665,646 B2 | 2/2010 | Prommersberger |
| 7,669,747 B2 | 3/2010 | Weisenburgh, II et al. |
| 7,744,627 B2 | 6/2010 | Orban, III et al. |
| 7,793,813 B2 | 9/2010 | Bettuchi |
| 7,823,592 B2 | 11/2010 | Bettuchi et al. |
| 7,845,533 B2 | 12/2010 | Marczyk et al. |
| 7,845,536 B2 | 12/2010 | Viola et al. |
| 7,909,224 B2 | 3/2011 | Prommersberger |
| 2002/0016626 A1 | 2/2002 | DiMatteo et al. |
| 2002/0019187 A1 | 2/2002 | Carroll et al. |
| 2002/0052622 A1 | 5/2002 | Rousseau |
| 2002/0091397 A1 | 7/2002 | Chen |
| 2002/0133236 A1 | 9/2002 | Rousseau |
| 2002/0138152 A1 | 9/2002 | Francis et al. |
| 2002/0151911 A1 | 10/2002 | Gabbay |
| 2002/0165559 A1 | 11/2002 | Grant et al. |
| 2002/0165562 A1 | 11/2002 | Grant et al. |
| 2002/0165563 A1 | 11/2002 | Grant et al. |
| 2002/0177859 A1 | 11/2002 | Monassevitch et al. |
| 2003/0065345 A1 | 4/2003 | Weadock |
| 2003/0065346 A1 | 4/2003 | Evens et al. |
| 2003/0083676 A1 | 5/2003 | Wallace |
| 2003/0088256 A1 | 5/2003 | Conston et al. |
| 2003/0105510 A1 | 6/2003 | DiMatteo et al. |
| 2003/0114866 A1 | 6/2003 | Ulmsten et al. |
| 2003/0120284 A1 | 6/2003 | Palacios |
| 2003/0167064 A1 | 9/2003 | Whayne |
| 2003/0181927 A1 | 9/2003 | Wallace |
| 2003/0183671 A1 | 10/2003 | Mooradian et al. |
| 2003/0208231 A1 | 11/2003 | Williamson, IV et al. |
| 2004/0034377 A1 | 2/2004 | Sharkawy et al. |
| 2004/0092960 A1 | 5/2004 | Abrams et al. |
| 2004/0093029 A1 | 5/2004 | Zubik et al. |
| 2004/0107006 A1 | 6/2004 | Francis et al. |
| 2004/0116945 A1 | 6/2004 | Sharkawy et al. |
| 2004/0142621 A1 | 7/2004 | Carroll et al. |
| 2004/0172048 A1 | 9/2004 | Browning |
| 2004/0209059 A1 | 10/2004 | Foss |
| 2004/0215214 A1 | 10/2004 | Crews et al. |
| 2004/0215219 A1 | 10/2004 | Eldridge et al. |
| 2004/0215221 A1 | 10/2004 | Suyker et al. |
| 2004/0254590 A1 | 12/2004 | Hoffman et al. |
| 2004/0260315 A1 | 12/2004 | Dell et al. |
| 2005/0002981 A1 | 1/2005 | Lahtinen et al. |
| 2005/0021026 A1 | 1/2005 | Baily |
| 2005/0021053 A1 | 1/2005 | Heinrich |
| 2005/0021085 A1 | 1/2005 | Abrams et al. |
| 2005/0059996 A1 | 3/2005 | Bauman et al. |
| 2005/0059997 A1 | 3/2005 | Bauman et al. |
| 2005/0070929 A1 | 3/2005 | Dalessandro et al. |
| 2005/0118435 A1 | 6/2005 | DeLucia et al. |
| 2005/0173490 A1 * | 8/2005 | Shelton ....................... 227/175.2 |
| 2005/0228446 A1 | 10/2005 | Mooradian et al. |
| 2005/0245965 A1 | 11/2005 | Orban et al. |
| 2006/0004407 A1 | 1/2006 | Hiles et al. |
| 2006/0025816 A1 * | 2/2006 | Shelton ........................ 606/215 |
| 2006/0085034 A1 | 4/2006 | Bettuchi |
| 2006/0135992 A1 | 6/2006 | Bettuchi et al. |
| 2006/0173470 A1 | 8/2006 | Oray et al. |
| 2006/0178683 A1 | 8/2006 | Shimoji et al. |
| 2006/0212050 A1 | 9/2006 | D'Agostino et al. |
| 2006/0212069 A1 * | 9/2006 | Shelton ........................ 606/205 |
| 2006/0271104 A1 | 11/2006 | Viola et al. |
| 2007/0034669 A1 | 2/2007 | de la Torre et al. |
| 2007/0049953 A2 | 3/2007 | Shimoji et al. |
| 2007/0179528 A1 | 8/2007 | Soltz et al. |
| 2007/0203509 A1 | 8/2007 | Bettuchi |
| 2007/0203510 A1 | 8/2007 | Bettuchi |
| 2007/0246505 A1 | 10/2007 | Pace-Floridia et al. |

| | | | |
|---|---|---|---|
| 2008/0029570 A1 | 2/2008 | Shelton et al. | |
| 2008/0082126 A1 | 4/2008 | Murray et al. | |
| 2008/0110959 A1 | 5/2008 | Orban et al. | |
| 2008/0125812 A1 | 5/2008 | Zubik et al. | |
| 2008/0140115 A1 | 6/2008 | Stopek | |
| 2008/0161831 A1 | 7/2008 | Bauman et al. | |
| 2008/0161832 A1 | 7/2008 | Bauman et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0290134 A1 | 11/2008 | Bettuchi et al. | |
| 2008/0308608 A1 | 12/2008 | Prommersberger | |
| 2008/0314960 A1 | 12/2008 | Marczyk et al. | |
| 2009/0001121 A1 | 1/2009 | Hess et al. | |
| 2009/0001122 A1 | 1/2009 | Prommersberger et al. | |
| 2009/0001123 A1 | 1/2009 | Morgan et al. | |
| 2009/0001124 A1 | 1/2009 | Hess et al. | |
| 2009/0001125 A1 | 1/2009 | Hess et al. | |
| 2009/0001126 A1 | 1/2009 | Hess et al. | |
| 2009/0001128 A1 | 1/2009 | Weisenburgh, II et al. | |
| 2009/0001130 A1 | 1/2009 | Hess et al. | |
| 2009/0005808 A1 | 1/2009 | Hess et al. | |
| 2009/0030452 A1 | 1/2009 | Bauman et al. | |
| 2009/0043334 A1 | 2/2009 | Bauman et al. | |
| 2009/0078739 A1 | 3/2009 | Viola | |
| 2009/0095791 A1 | 4/2009 | Eskaros et al. | |
| 2009/0095792 A1 | 4/2009 | Bettuchi | |
| 2009/0120994 A1 | 5/2009 | Murray et al. | |
| 2009/0134200 A1 | 5/2009 | Tarinelli et al. | |
| 2009/0206125 A1 | 8/2009 | Huitema et al. | |
| 2009/0206126 A1 | 8/2009 | Huitema et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0218384 A1 | 9/2009 | Aranyi | |
| 2009/0277947 A1 | 11/2009 | Viola | |
| 2009/0287230 A1 | 11/2009 | D'Agostino et al. | |
| 2010/0012704 A1 | 1/2010 | Tarinelli Racenet et al. | |
| 2010/0065606 A1 | 3/2010 | Stopek | |
| 2010/0065607 A1 | 3/2010 | Orban, III et al. | |
| 2010/0072254 A1 | 3/2010 | Aranyi et al. | |
| 2010/0147921 A1 | 6/2010 | Olson | |
| 2010/0147922 A1 | 6/2010 | Olson | |
| 2010/0147923 A1 | 6/2010 | D'Agostino et al. | |
| 2010/0243707 A1 | 9/2010 | Olson et al. | |
| 2010/0243708 A1 | 9/2010 | Aranyi et al. | |
| 2010/0243711 A1 | 9/2010 | Olson et al. | |
| 2010/0249805 A1 | 9/2010 | Olson et al. | |
| 2010/0264195 A1 | 10/2010 | Bettuchi | |
| 2010/0282815 A1 | 11/2010 | Bettuchi et al. | |
| 2011/0024476 A1 | 2/2011 | Bettuchi et al. | |
| 2011/0024481 A1 | 2/2011 | Bettuchi et al. | |
| 2011/0036894 A1 | 2/2011 | Bettuchi | |
| 2011/0042442 A1 | 2/2011 | Viola et al. | |
| 2011/0046650 A1 | 2/2011 | Bettuchi | |
| 2011/0057016 A1 | 3/2011 | Bettuchi | |

FOREIGN PATENT DOCUMENTS

| | | |
|---|---|---|
| DE | 199 24 311 A1 | 11/2000 |
| EP | 0 594 148 A1 | 4/1994 |
| EP | 0 327 022 B1 | 4/1995 |
| EP | 0 667 119 A1 | 8/1995 |
| EP | 1 064 883 A1 | 1/2001 |
| EP | 1 256 317 A2 | 11/2002 |
| EP | 1 520 525 A1 | 4/2005 |
| EP | 1 621 141 A2 | 2/2006 |
| EP | 1 759 640 A2 | 3/2007 |
| EP | 1 994 890 A1 | 11/2008 |
| EP | 2 005 894 A2 | 12/2008 |
| EP | 2 005 895 A2 | 12/2008 |
| WO | WO 90/05489 A1 | 5/1990 |
| WO | WO 96/22055 A1 | 7/1996 |
| WO | WO 97/01989 A1 | 1/1997 |
| WO | WO 97/13463 A1 | 4/1997 |
| WO | WO 98/17180 A1 | 4/1998 |
| WO | WO 99/45849 A1 | 9/1999 |
| WO | WO 03/082126 A1 | 10/2003 |
| WO | WO 03/105698 A2 | 12/2003 |
| WO | WO 2006/023578 A2 | 3/2006 |
| WO | WO 2006/044490 A2 | 4/2006 |
| WO | WO 2006/083748 A1 | 8/2006 |
| WO | WO 2007/121579 A1 | 11/2007 |
| WO | WO 2008/057281 A2 | 5/2008 |
| WO | WO 2008/109125 A1 | 9/2008 |

OTHER PUBLICATIONS

International Search Report corresponding to European Application No. EP 06 01 6962.0, completed on Jan. 3, 2007 and mailed on Jan. 11, 2007; 10 pages.

International Search Report corresponding to International Application No. PCT/US05/36740, completed on Feb. 20, 2007 and mailed on Mar. 23, 2007; 8 pages.

International Search Report corresponding to International Application No. PCT/US2008/002981, completed on Jun. 9, 2008 and mailed on Jun. 26, 2008; 2 pages.

International Search Report corresponding to European Application No. EP 08 25 1779, completed on Jul. 14, 2008 and mailed on Jul. 23, 2008; 5 pages.

International Search Report corresponding to European Application No. EP 08 25 1989.3, completed on Mar. 11, 2010 and mailed on Mar. 24, 2010; 6 pages.

International Search Report corresponding to European Application No. EP 10 25 0715.9, completed on Jun. 30, 2010 and mailed on Jul. 20, 2010; 3 pages.

International Search Report corresponding to European Application No. EP 05 80 4382.9, completed on Oct. 5, 2010 and mailed on Oct. 12, 2010; 3 pages.

International Search Report corresponding to European Application No. EP 10 25 1437.9, completed on Nov. 22, 2010 and mailed on Dec. 16, 2010; 3 pages.

International Search Report corresponding to European Application No. EP 09 25 2897.5, completed on Feb. 7, 2011 and mailed on Feb. 15, 2011; 3 pages.

International Search Report corresponding to European Application No. EP 10 25 0642.5, completed on Mar. 25, 2011 and mailed on Apr. 4, 2011; 4 pages.

International Search Report corresponding to European Application No. EP 11 18 8309.6, completed on Dec. 15, 2011 and mailed on Jan. 12, 2012; 3 pages.

* cited by examiner

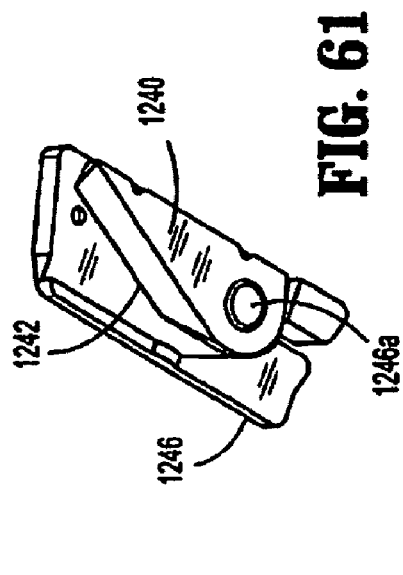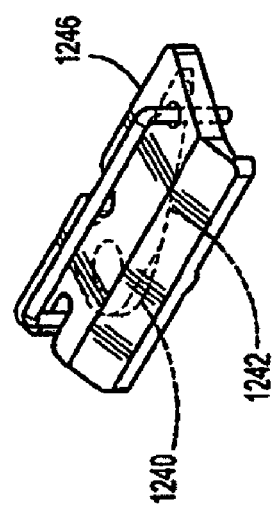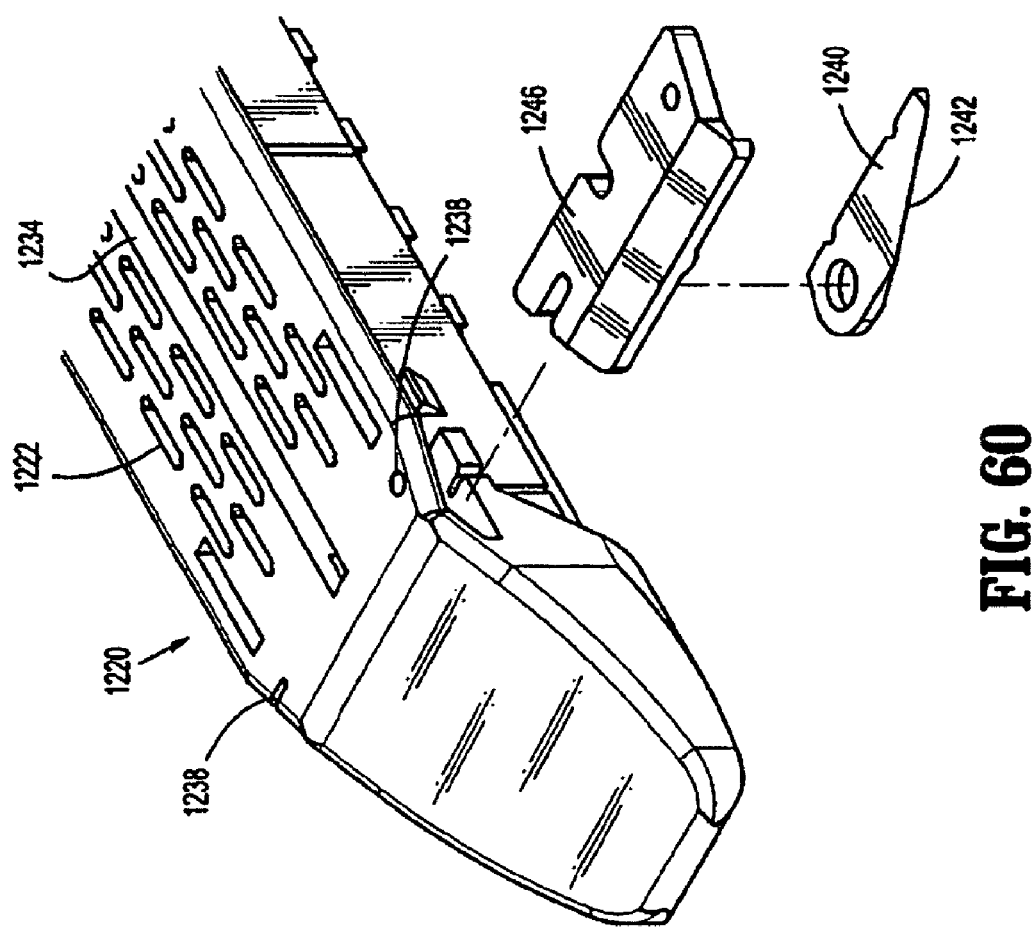

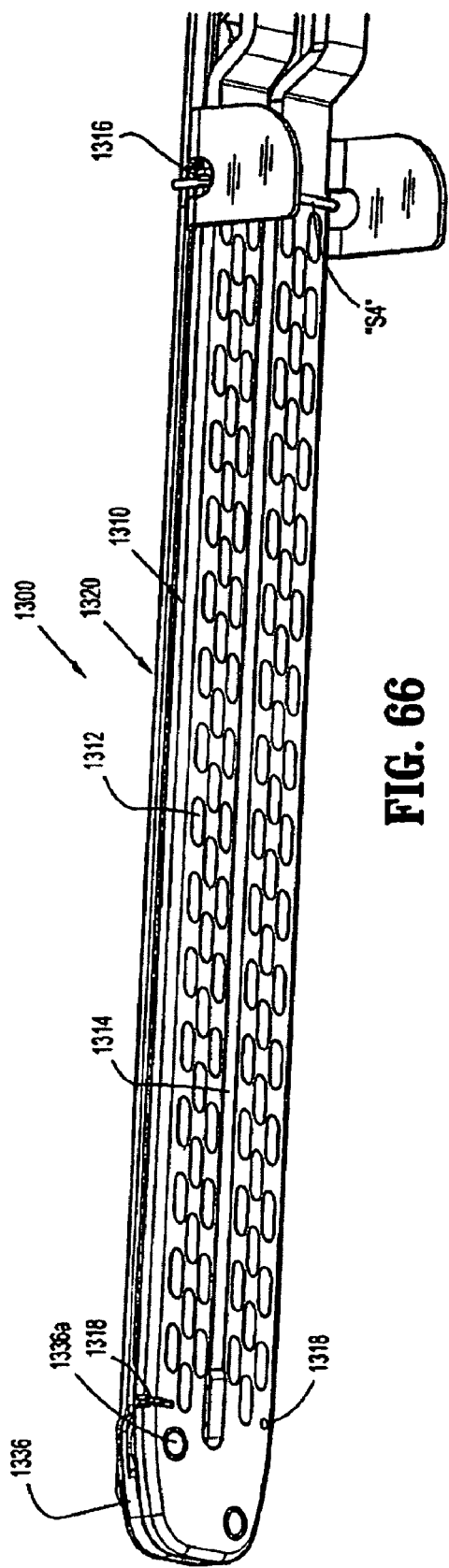
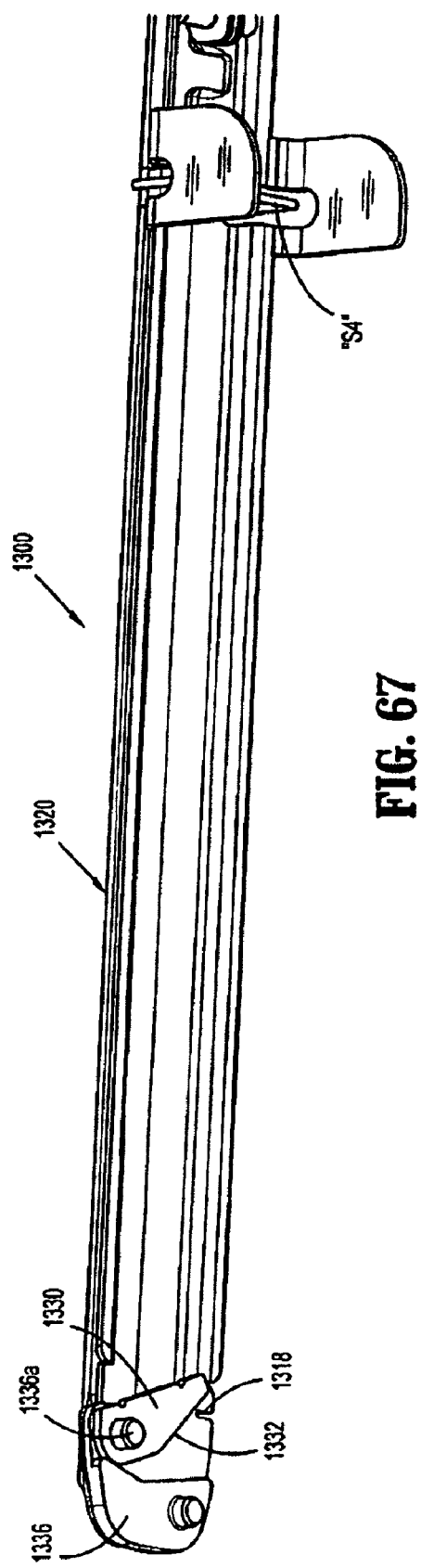
FIG. 66
FIG. 67

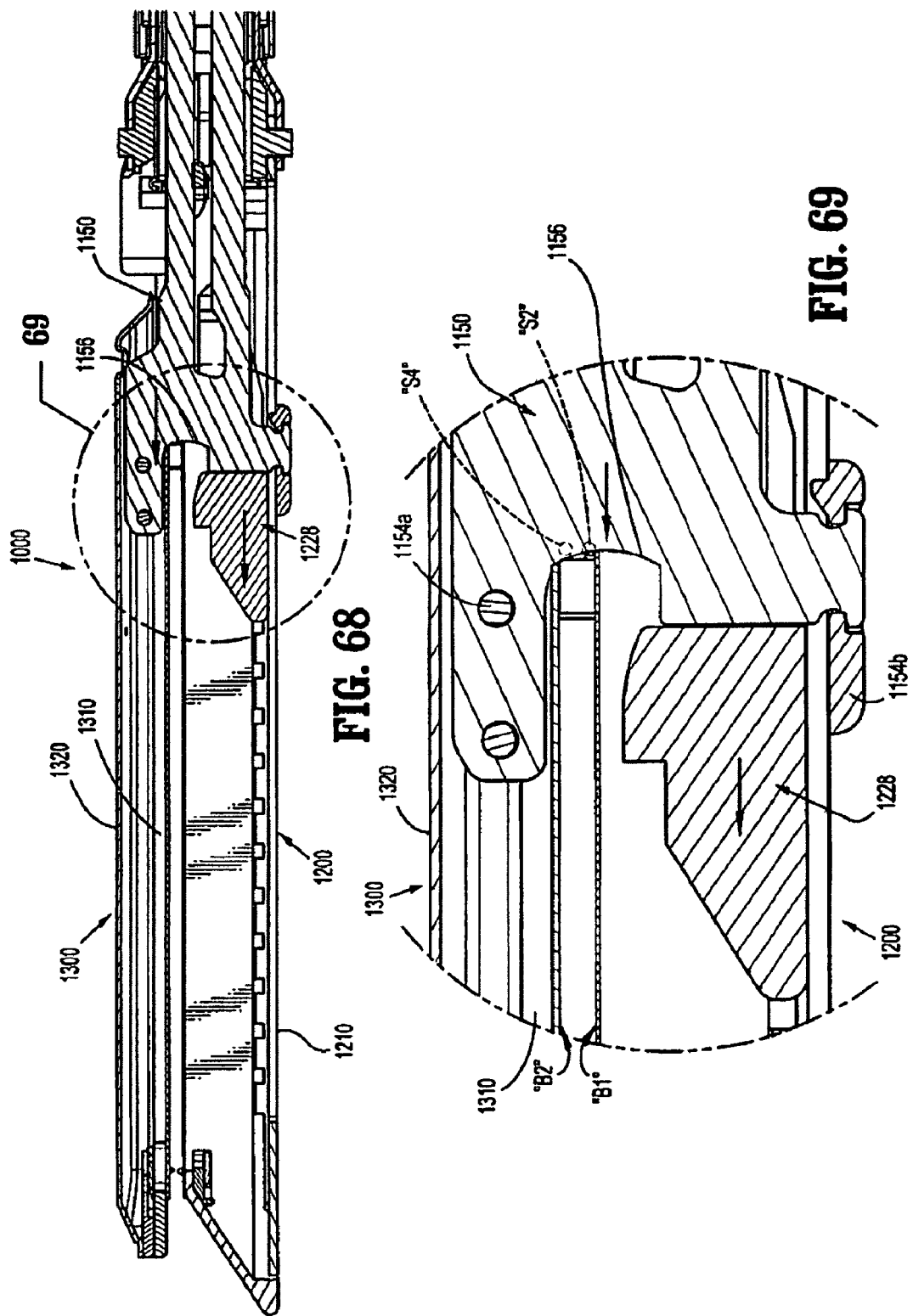

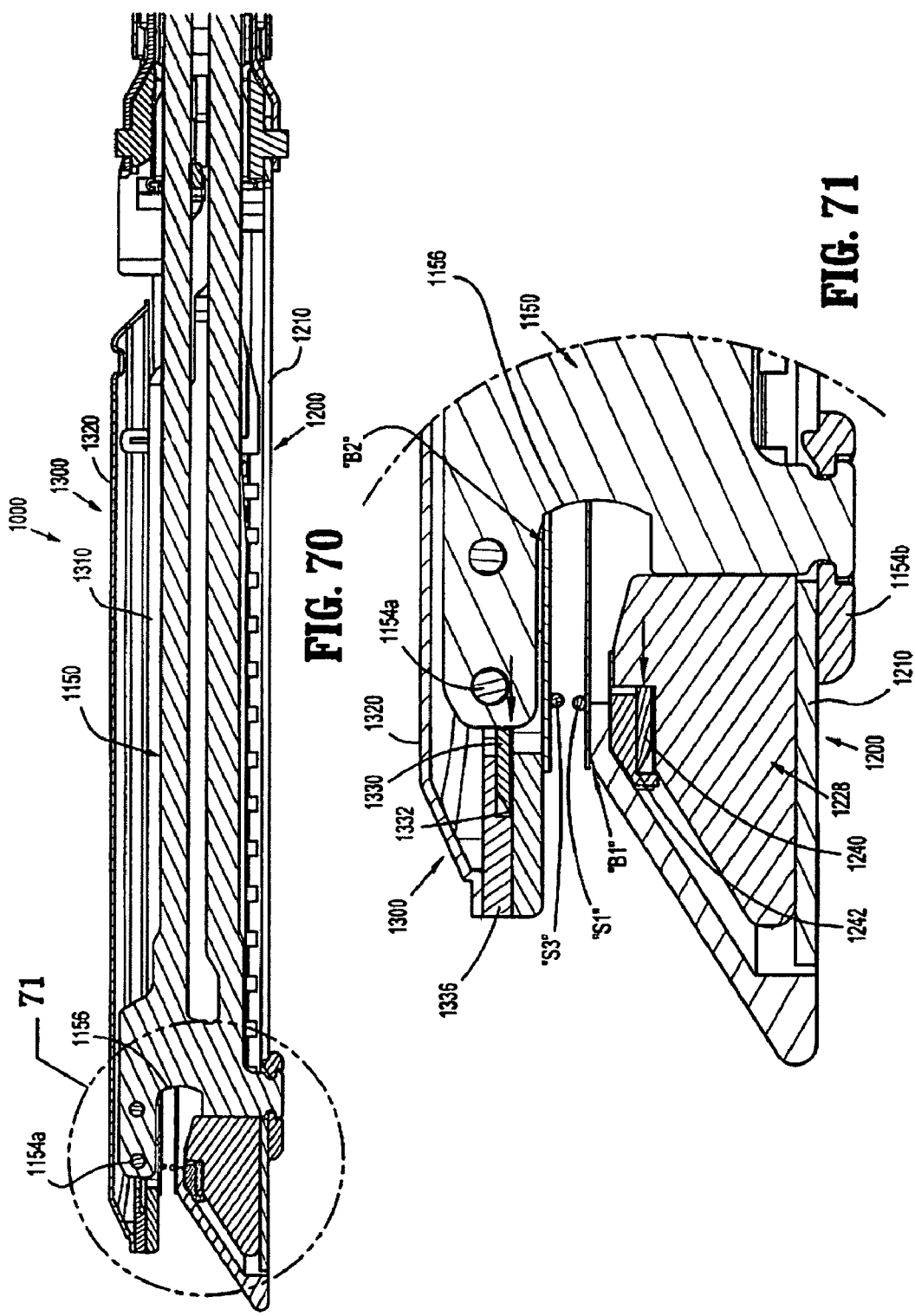

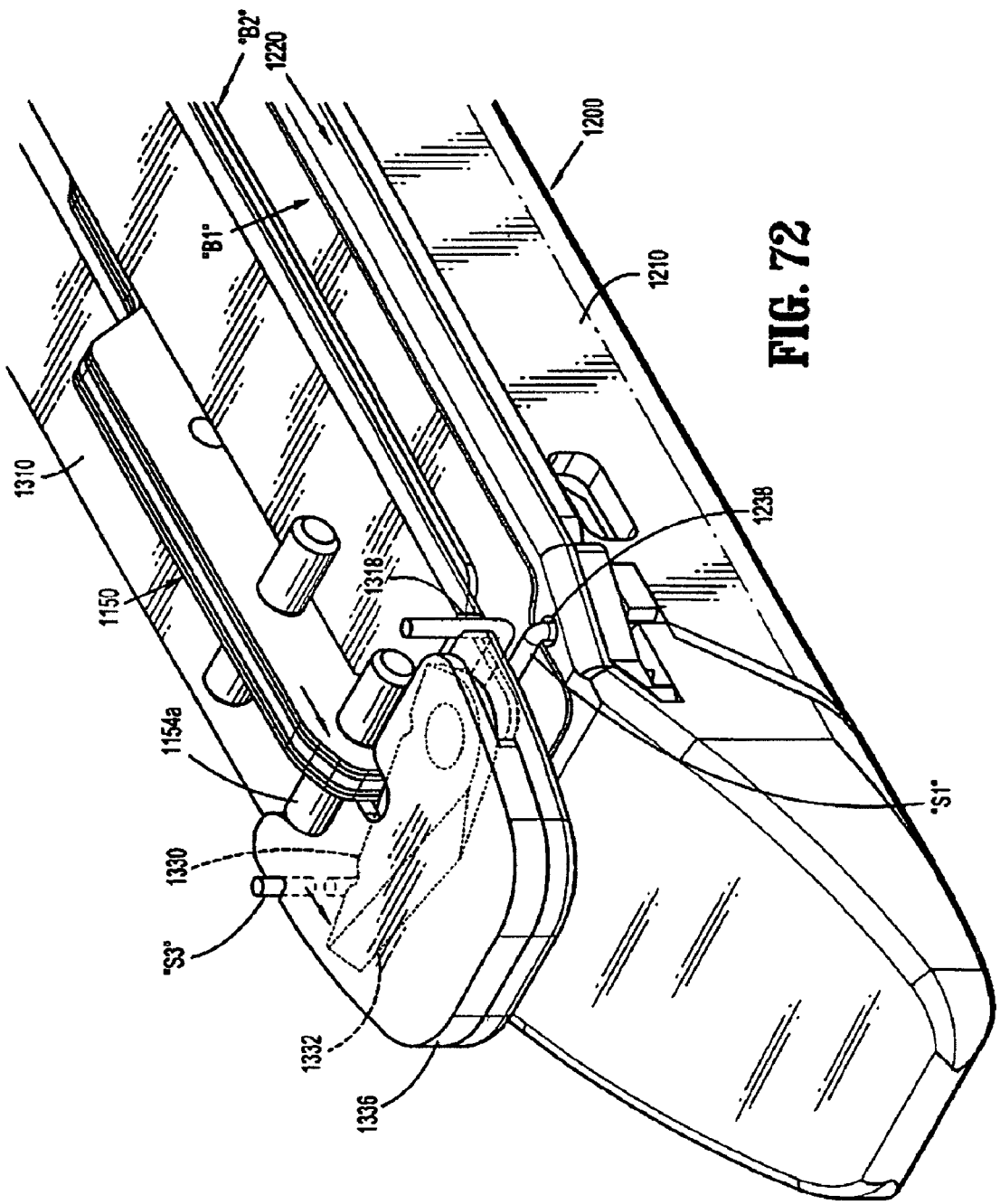

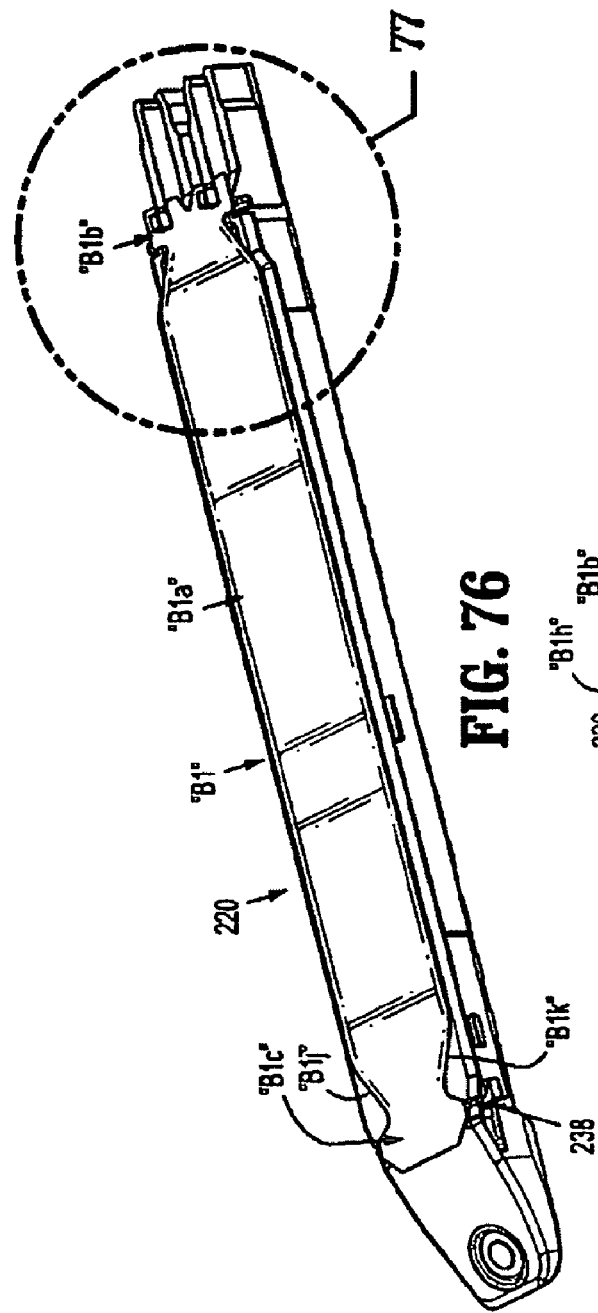
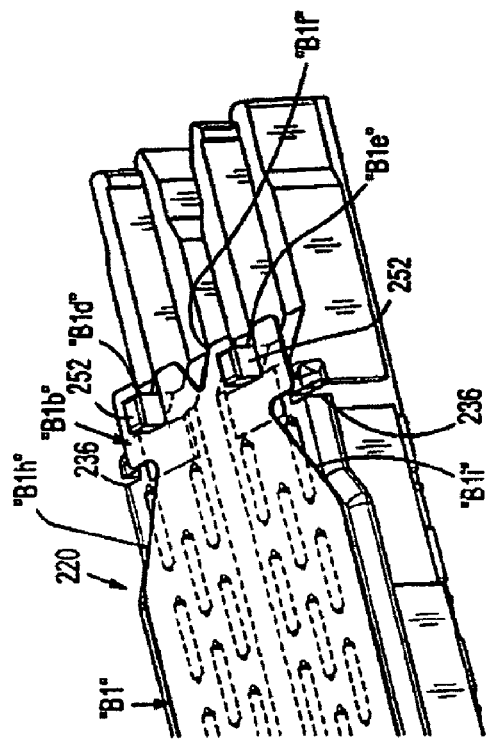
FIG. 76
FIG. 77

SURGICAL STAPLING APPARATUS

CROSS-REFERENCE TO RELATED APPLICATIONS

The present application is a continuation of U.S. application Ser. No. 12/342,400, filed Dec. 23, 2008 (now U.S. Pat. No. 8,011,555), which is a continuation-in-part of U.S. application Ser. No. 12/528,526, filed Aug. 25, 2009, which is a National Stage Application of PCT/US2008/002981 under 35USC §371(a) filed Mar. 5, 2008, which claims priority of U.S. Provisional Patent Application Ser. No. 60/905,566, filed Mar. 6, 2007, the disclosures of each of the above-identified applications are hereby incorporated by reference in their entirety.

BACKGROUND

1. Technical Field

The present disclosure relates to a surgical apparatus, e.g., a surgical stapling apparatus. More particularly, the present disclosure relates to a surgical stapling apparatus including a detachable surgical buttress and/or an endoscopic surgical stapling apparatus that includes a detachable surgical buttress for a loading unit, e.g., a single use loading unit ("SULU") or disposable loading unit ("DLU"). For simplicity, hereinafter, SULU or DLU will be referred to as "DLU", but it should be understood to include either or both a DLU or SULU.

2. Background of Related Art

Surgical devices wherein tissue is first grasped or clamped between opposing jaw structure and then joined by surgical fasteners are well known in the art. In some instruments a knife is provided to cut the tissue which has been joined by the fasteners. The fasteners are typically in the form of surgical staples but two part polymeric fasteners can also be utilized.

Instruments for this purpose can include two elongated jaw members which are respectively used to capture or clamp tissue. Typically, one of the jaw members carries a staple cartridge which houses a plurality of staples arranged in at least two lateral rows while the other jaw member has an anvil that defines a surface for forming the staple legs as the staples are driven from the staple cartridge. Generally, the stapling operation is effected by cam members that travel longitudinally through the staple cartridge, with the cam members acting upon staple pushers to sequentially eject the staples from the staple cartridge. A knife can travel between the staple rows to longitudinally cut and/or open the stapled tissue between the rows of staples. Such instruments are disclosed, for example, in U.S. Pat. No. 3,079,606 and U.S. Pat. No. 3,490,675.

A later stapler disclosed in U.S. Pat. No. 3,499,591 also applies a double row of staples on each side of the incision. This patent discloses a surgical stapler that has a disposable loading unit in which a cam member moves through an elongate guide path between two sets of staggered staple carrying grooves. Staple drive members are located within the grooves and are positioned in such a manner so as to be contacted by the longitudinally moving cam member to effect ejection of the staples from the staple cartridge of the disposable loading unit. Other examples of such staplers are disclosed in U.S. Pat. Nos. 4,429,695 and 5,065,929.

Each of the instruments described above is designed for use in conventional surgical procedures wherein surgeons have direct manual access to the operative site. However, in endoscopic or laparoscopic procedures, surgery is performed through a small incision or through a narrow cannula inserted through small entrance wounds in the skin. In order to address the specific needs of endoscopic and/or laparoscopic surgical procedures, endoscopic surgical stapling devices have been developed and are disclosed in, for example, U.S. Pat. No. 5,040,715 (Green, et al.); U.S. Pat. No. 5,307,976 (Olson, et al.); U.S. Pat. No. 5,312,023 (Green, et al.); U.S. Pat. No. 5,318,221 (Green, et al.); U.S. Pat. No. 5,326,013 (Green, et al.); U.S. Pat. No. 5,332,142 (Robinson, et al.); and U.S. Pat. No. 6,241,139 (Milliman et al.), the entire contents of each of which are incorporated herein by reference.

Tyco Healthcare Group, LP, the assignee of the present application, has manufactured and marketed endoscopic stapling instruments, such as the Multifire ENDO GIA™. 30 and Multifire ENDO GIA™. 60 instruments, for a number of years. These instruments include a surgical stapling apparatus and a DLU. Typically, the DLU is attached to the apparatus immediately prior to surgery. After use, the DLU can be removed from the apparatus and a new DLU can be fastened to the apparatus to perform additional stapling and/or cutting operations. These instruments have provided significant clinical benefits. Nonetheless, improvements to these instruments are still possible.

It would be desirable to provide a surgical buttress selectively connected to at least one of the tissue contacting surfaces of the cartridge half-section and the anvil half-section of the surgical stapling apparatus.

It would also be desirable to provide a system for removing the surgical buttress from the tissue contacting surface of the cartridge half-section and/or the tissue contacting surface of the anvil half-section during a firing of the surgical stapling apparatus.

Accordingly, it is an object of this disclosure to meet the aforementioned desires.

SUMMARY

In accordance with the present disclosure a surgical stapling apparatus is provided including a housing; a handle supported by the housing; an elongated body extending distally from the housing and having a distal end adapted to releasably engage a loading unit; and a loading unit supportable on a distal end of the housing. The loading unit includes a tool assembly having a cartridge assembly configured and adapted to releasably support a staple cartridge having a plurality of surgical fasteners therein, and an anvil assembly movably secured in relation to the cartridge assembly, wherein the anvil assembly is configured and adapted to support an anvil plate and, wherein each of the anvil plate and the staple cartridge define an elongate longitudinal slot. The loading unit further includes a surgical buttress releasably secured to a tissue contacting surface of at least one of the anvil plate and the staple cartridge, wherein each surgical buttress is secured to the at least one of the anvil assembly and the cartridge assembly by at least one anchor. The loading unit still further includes a drive assembly slidably supported in the tool assembly, the drive assembly including a knife blade slidably disposed within each elongate longitudinal slot, wherein movement of the drive assembly from a proximal position to a distal position results in the knife blade thereof cutting the at least one anchor and freeing each surgical buttress from the respective at least one anvil assembly and cartridge assembly.

The anvil assembly may include a proximal suture securing the surgical buttress thereto and/or a distal anchor securing the surgical buttress thereto. The cartridge assembly may include a proximal anchor securing the surgical buttress thereto and/or a distal anchor securing the surgical buttress thereto. Each anchor of the anvil assembly and the cartridge assembly may extend across the respective longitudinal slot of the anvil plate and the staple cartridge.

The anvil assembly may include a knife blade slidably or rotatably supported therein and defining a knife edge. The knife blade of the anvil assembly may cut at least one of the proximal and distal anchors of the anvil assembly upon actuation thereof. The knife blade of the anvil assembly may have a first position located substantially proximal of the distal anchor of the anvil assembly and a second position located substantially distal of the distal anchor of the anvil assembly, thereby cutting the distal anchor of the anvil assembly. The drive assembly may move the knife blade of the anvil assembly from the first position to the second position upon distal actuation of the drive assembly.

The cartridge assembly may include a knife blade slidably or rotatably supported therein and defining a knife edge, wherein the knife blade of the cartridge assembly cuts at least one of the proximal and distal anchors of the cartridge assembly upon actuation thereof. The knife blade of the cartridge assembly may have a first position located substantially proximal of the distal anchor of the cartridge assembly and a second position located substantially distal of the distal anchor of the cartridge assembly, thereby cutting the distal anchor of the cartridge assembly. The drive assembly may move the knife blade of the cartridge assembly from the first position to the second position upon distal actuation of the drive assembly.

According to another aspect of the present disclosure, a loading unit for use with a surgical stapling apparatus is provided. The loading unit includes a tool assembly having a cartridge assembly configured and adapted to releasably support a staple cartridge having a plurality of surgical fasteners therein, and an anvil assembly movably secured in relation to the cartridge assembly, wherein the anvil assembly is configured and adapted to support an anvil plate and, wherein each of the anvil plate and the staple cartridge define an elongate longitudinal slot. The loading unit also includes a surgical buttress releasably secured to a tissue contacting surface of at least one of the anvil plate and the staple cartridge, wherein each surgical buttress is secured to the at least one of the anvil assembly and the cartridge assembly by at least one anchor. The loading unit further includes a drive assembly slidably supported in the tool assembly, the drive assembly including a knife blade slidably disposed within each elongate longitudinal slot, wherein movement of the drive assembly from a proximal position to a distal position results in the knife blade thereof cutting the at least one anchor and freeing each surgical buttress from the respective at least one anvil assembly and cartridge assembly.

According to yet another aspect of the present disclosure, a loading unit for selective use with a surgical stapling apparatus is provided. The loading unit includes a tool assembly having a cartridge assembly configured and adapted to releasably support a staple cartridge having a plurality of surgical fasteners therein, and an anvil assembly movably secured in relation to the cartridge assembly, wherein the anvil assembly is configured and adapted to support an anvil plate and, wherein each of the anvil plate and the staple cartridge define an elongate longitudinal slot. The loading unit further includes a surgical buttress releasably secured to a tissue contacting surface of each of the anvil plate and the staple cartridge; and anchors securing the surgical buttress to each of the anvil plate and the staple cartridge, wherein an anchor is located near a proximal end and a distal end of each of the anvil assembly and the cartridge assembly. The loading unit also includes a knife blade operatively disposed in the anvil assembly, wherein the knife blade of the anvil assembly has a first position located proximal of a distal anchor of the anvil assembly and a second position located distal of the distal anchor of the anvil assembly, thereby cutting the distal anchor of the anvil assembly. The loading unit still further includes a knife blade operatively disposed in the cartridge assembly, wherein the knife blade of the cartridge assembly has a first position located proximal of a distal anchor of the cartridge assembly and a second position located distal of the distal anchor of the cartridge assembly, thereby cutting the distal anchor of the cartridge assembly. The loading unit also includes a drive assembly slidably supported in the tool assembly, the drive assembly including a knife blade slidably disposed within each elongate longitudinal slot, wherein movement of the drive assembly from a proximal position to a distal position results in the knife blade thereof cutting a proximal anchor of each of the anvil assembly and the cartridge assembly and freeing a proximal end of each surgical buttress from the respective at least one anvil assembly and cartridge assembly, and wherein movement of the drive assembly from the proximal position to the distal position moves the knife blade of the anvil assembly and the knife blade of the cartridge assembly from their respective first positions to their respective second positions, thereby cutting a respective distal anchor of the anvil assembly and the cartridge assembly and freeing a distal end of each surgical buttress from the respective at least one anvil assembly and cartridge assembly.

According to a further aspect of the present disclosure, a surgical stapling apparatus is provided. The surgical stapling apparatus includes a cartridge assembly defining a tissue contacting surface; an anvil assembly defining a tissue contacting surface; and a surgical buttress releasably secured to at least one of the tissue contacting surface of the cartridge assembly and the tissue contacting surface of the anvil assembly by at least one anchor.

An anchor may be placed near at least one of a proximal end and a distal end of each surgical buttress. Each anchor may extend transverse to a longitudinal axis of a respective one of the cartridge assembly and the anvil assembly.

The anchor may be selected from the group consisting of sutures, threads, tethers, straps, bands, lines, wires, cables, tacks, anchors, and fasteners.

At least a proximal anchor may extend across a respective longitudinal knife slot formed in each of the cartridge assembly and the anvil assembly and/or at least a distal anchor may extend across a respective longitudinal knife slot formed in each of the cartridge assembly and the anvil assembly.

The anchor may release a respective surgical buttress upon firing of the surgical stapling apparatus. Each anchor may be severed to release the surgical buttress upon a firing of the surgical stapling apparatus.

The surgical stapling apparatus may include a knife blade configured and dimensioned for slidable reciprocation through a respective longitudinal knife slot formed in each of the cartridge assembly and the anvil assembly, wherein the knife blade severs an anchor upon distal advancement thereof.

The surgical stapling apparatus may further include a drive assembly slidably supported for axial displacement along the cartridge assembly and the anvil assembly, wherein movement of the drive assembly from a proximal position to a distal position results in the separation of the surgical buttress from a respective one of the cartridge assembly and the anvil assembly.

An anchor may be placed near at least one of a proximal end and a distal end of each surgical buttress. The drive assembly may either directly cut each anchor or may cause each anchor to be cut in order to release the surgical buttress from the respective cartridge assembly and anvil assembly.

According to a further embodiment of the present disclosure, a surgical stapling apparatus is provided and includes a cartridge assembly defining a tissue contacting surface and a longitudinally extending elongate slot; an anvil assembly defining a tissue contacting surface and a longitudinally extending elongate slot; and a surgical buttress releasably secured to at least one of the tissue contacting surface of the cartridge assembly and the tissue contacting surface of the anvil assembly by at least one anchor, wherein each buttress defines a notch formed in a proximal edge thereof and substantially aligned with the longitudinally extending elongate slot of a respective cartridge assembly and anvil assembly.

The surgical stapling apparatus may further include a central knife blade slidably disposable in the longitudinal extending elongate slot of the cartridge assembly and the anvil assembly, wherein the central knife blade is received in the notch of each surgical buttress upon an advancement of the central knife blade through the longitudinal extending elongate slot.

Each of the cartridge assembly and the anvil assembly may include a distal pair of constricting slots formed in a respective side edge thereof; and a proximal pair of constricting slots formed in a respective side edge thereof. A suture may extend across respective distal and proximal pairs of constricting slots of the cartridge assembly and the anvil assembly for securing a respective surgical buttress thereto.

Each surgical buttress may include a notch formed in a side edge thereof in registration with each constricting slot.

The surgical stapling apparatus may further include a knife blade supported in a distal end portion of at least one of the cartridge assembly and the anvil assembly. The distal knife blade may be actuatable by the central knife blade upon an actuation of the central knife blade.

The surgical stapling apparatus may still further include a knife blade supported in a distal end portion of at least one of the cartridge assembly and the anvil assembly, wherein the central knife blade is supported on a drive bar, and wherein the distal knife blade is actuatable by at least one of the central knife blade and the drive bar upon an actuation of the drive bar.

According to yet another embodiment of the present disclosure, a surgical stapling apparatus is provided and includes a cartridge assembly defining a tissue contacting surface; an anvil assembly defining a tissue contacting surface, wherein the tissue contacting surface of at least one of the cartridge assembly and the anvil assembly includes a grip enhancing feature formed thereon; and a surgical buttress releasably secured to at least one of the tissue contacting surface of the cartridge assembly and the tissue contacting surface of the anvil assembly by at least one anchor, wherein a position of the surgical buttress relative to a respective cartridge assembly and anvil assembly is better maintained as compared to a cartridge assembly and a anvil assembly devoid of the grip enhancing feature.

The tissue contacting surface of at least one of the cartridge assembly and the anvil assembly may include at least one of a distal grip enhancing feature and a proximal grip enhancing feature.

Each of the cartridge assembly and the anvil assembly may define a longitudinally extending elongate slot, and wherein the tissue contacting surface of at least one of the cartridge assembly and the anvil assembly includes at least one of a distal grip enhancing feature disposed distal of the longitudinally extending elongate slot and a proximal grip enhancing feature disposed on opposed sides of the longitudinally extending elongate slot.

Each grip enhancing feature may be a projection extending from the tissue contacting surface.

According to still a further embodiment of the present disclosure, a surgical stapling apparatus is provided and includes a cartridge assembly defining a tissue contacting surface and a longitudinally extending elongate slot; an anvil assembly defining a tissue contacting surface and a longitudinally extending elongate slot; a surgical buttress releasably secured to at least one of the tissue contacting surface of the cartridge assembly and the tissue contacting surface of the anvil assembly by at least one anchor; a central knife blade slidably disposable in the longitudinal extending elongate slot of the cartridge assembly and the anvil assembly; and a knife blade supported in a distal end portion of at least one of the cartridge assembly and the anvil assembly, wherein the distal knife blade is actuatable by the central knife blade upon an actuation of the central knife blade.

At least one of the distal knife blades may be biased to a proximal position by a biasing member. The biasing member may be at least one of a leaf spring and a coil spring.

The cartridge assembly and the anvil assembly may include a distal suture for securing a distal end of a respective surgical buttress to a tissue contacting surface thereof. Each distal knife blade may sever a respective distal suture upon a firing of the surgical stapling apparatus. Each distal knife blade may have at least a first position disposed proximal of the respective distal suture and at least a second position disposed distal of the respective distal suture. Each distal knife blade may be roatably supported in the respective cartridge assembly and anvil assembly.

At least one distal knife blade may define a concave distal knife edge. At least one distal knife blade may define a double-beveled knife edge. The distal knife edge may be concave.

At least one distal knife blade may define a distally extending tooth projecting therefrom. At least one distal knife blade may define an aperture for pivotal support on a hub, wherein the aperture of the distal knife blade and the hub each define complementary planar surface for maintaining a relative position of the distal knife blade with respect to the at least one anchor prior to a firing of the surgical stapling apparatus.

Additional advantages will become apparent from the description which follows, taken in conjunction with the accompanying drawings.

BRIEF DESCRIPTION OF THE DRAWINGS

The present disclosure will be further described with reference to the accompanying drawings, wherein like reference numerals refer to like parts in the several views, and wherein:

FIG. 60 is a perspective view, with parts separated, of the distal end of the cartridge assembly of FIG. 56;

FIG. 61 is a bottom, perspective view of a knife blade assembly of the cartridge assembly of FIG. 56;

FIG. 62 is a top, perspective view of a knife blade assembly of the cartridge assembly of FIG. 56;

FIG. 66 is a bottom, perspective view of the anvil assembly of FIG. 65, with a buttress removed therefrom;

FIG. 67 is a bottom, perspective view of the anvil assembly of FIG. 65, with a buttress and an anvil plate removed therefrom;

FIG. 68 is a longitudinal cross-sectional elevation view of the DLU, as taken through 53-53 of FIG. 47, illustrating an initial actuation of a drive assembly thereof;

FIG. 69 is an enlarged view of the indicated area of detail of FIG. 68;

FIG. 70 is a longitudinal cross-sectional elevation view of the DLU, as taken through 53-53 of FIG. 47, illustrating a final actuation of the drive assembly thereof;

FIG. 71 is an enlarged view of the indicated area of detail of FIG. 70;

FIG. 72 is an enlarged distal perspective view of the DLU of FIGS. 70 and 71, following an actuation thereof;

FIG. 76 is a perspective view of a cartridge assembly of a DLU according to another embodiment of the present disclosure, including a surgical cartridge buttress according to another embodiment of the present disclosure;

FIG. 77 is an enlarged view of the indicated area of detail of FIG. 76;

DETAILED DESCRIPTION OF EMBODIMENTS

Figure 1:
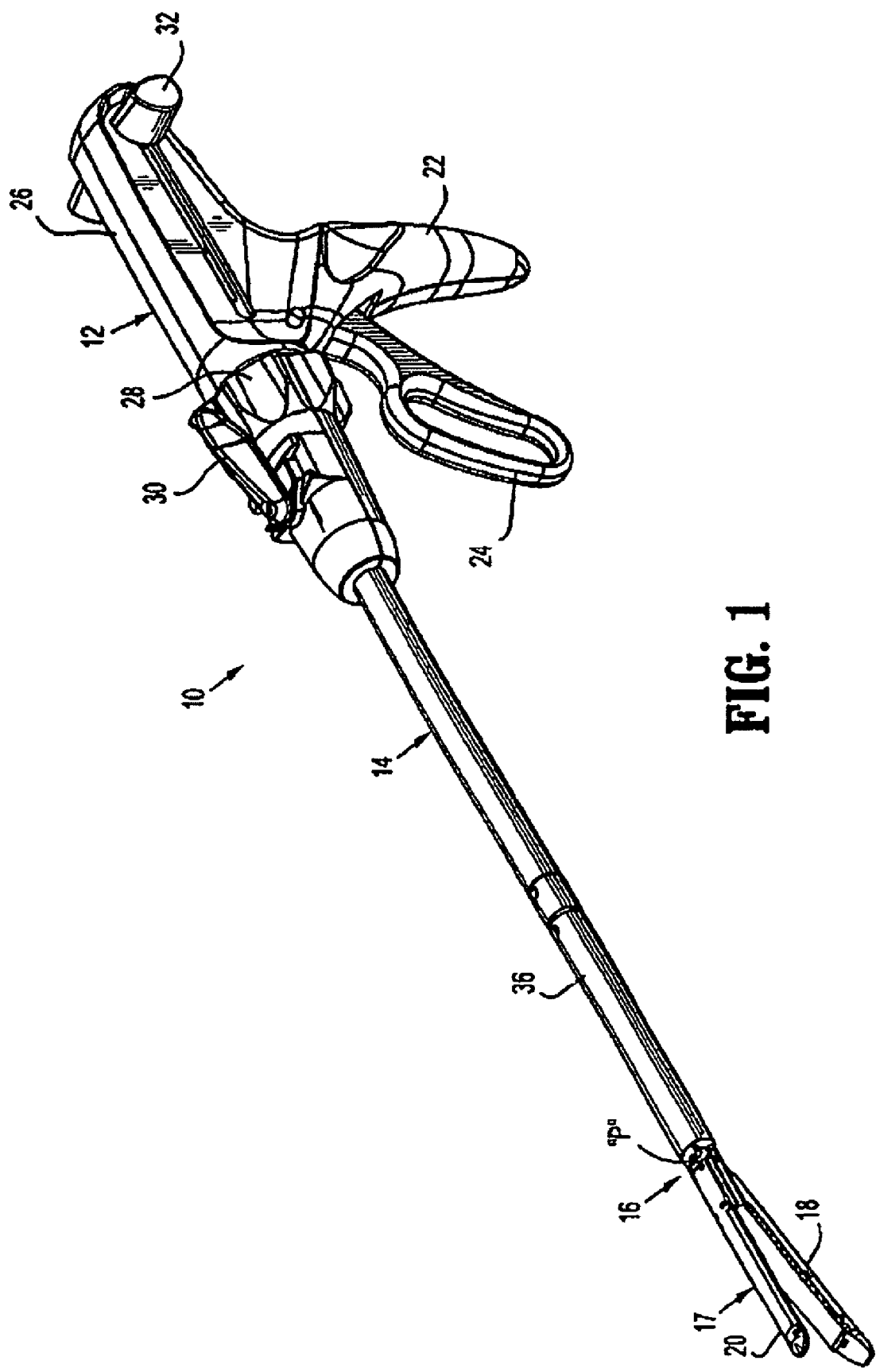
FIG. 1 is a perspective view of a surgical stapling apparatus according to an embodiment of the present disclosure.

Embodiments of the presently disclosed surgical stapling apparatus and DLU will now be described in detail with reference to the drawings, in which like reference numerals designate identical or corresponding elements in each of the several views.

In the drawings and in the description that follows, the term "proximal", as is traditional, will refer to the end of the stapling apparatus which is closest to the operator, while the term "distal" will refer to the end of the apparatus which is furthest from the operator.

FIG. 1 shows a surgical apparatus, e.g., surgical stapling apparatus, generally referred to as 10. In the interest of brevity, this disclosure will focus primarily on systems, methods and structures for loading, engaging, coupling or connecting a disposable loading unit ("DLU") 16 to surgical stapling apparatus 10. A detailed discussion of the remaining components and method of use of surgical stapling apparatus 10 is disclosed in U.S. Pat. No. 6,241,139.

Surgical stapling apparatus 10 is an endoscopic apparatus and includes a handle assembly 12 and an elongated body 14 extending from handle assembly 12. A DLU 16 is releasably secured to the distal end of elongated body 14. While this disclosure relates to the use of a DLU with surgical stapling apparatus 10, it is understood and within the scope of the present disclosure that a single use loading unit (SULU) or other end effector and/or tool assembly can equally be used in cooperation with surgical stapling apparatus 10.

DLU 16 includes a tool assembly 17 having a cartridge assembly 18 housing a plurality of surgical fasteners or staples 84 (see FIG. 2) and an anvil assembly 20 movably secured in relation to cartridge assembly 18. As shown herein, DLU 16 is configured to apply six (6) linear rows of staples, in DLUs measuring from about 30 mm to about 60 mm in length. DLUs for applying any number of rows of staples, having staple pockets arranged in various patterns and/or DLUs and end effectors having any other lengths, e.g., 45 mm, are also envisioned. Handle assembly 12 includes a stationary handle member 22, a movable handle member 24, and a barrel portion 26.

A rotatable member 28 is mounted on the forward end of barrel portion 26 to facilitate rotation of elongated body 14 and attached DLU 16 with respect to handle assembly 12. An articulation lever 30 is also mounted on the forward end of barrel portion 26 adjacent rotatable member 28 to facilitate articulation of tool assembly 17. Preferably, a pair of knobs 32 are movably positioned along barrel portion 26. Knobs 32 are advanced distally to approximate or close cartridge and/or anvil assembly 18, 20, and retracted proximally to unapproximate or open cartridge and/or anvil assembly 18, 20.

DLU 16 is desirably selectively removably couplable to elongated body 14. DLU 16 includes a housing portion 36 having a proximal end adapted to releasably engage the distal end of elongated body 14. A mounting assembly 38 is pivotally secured at "P" to the distal end of housing portion 36, and is configured to receive the proximal end of tool assembly 17 such that pivotal movement of tool assembly 17 about an axis at "P", perpendicular to the longitudinal axis of housing portion 36, effects articulation of tool assembly 17.

With general reference to FIGS. 2-8, DLU 16 includes a mounting assembly 40. Mounting assembly 40 includes an upper and a lower mounting portion 40a, 40b, respectively. A centrally located pivot member 42 extends from each of upper and lower mounting portions 40a, 40b.

Figure 2:
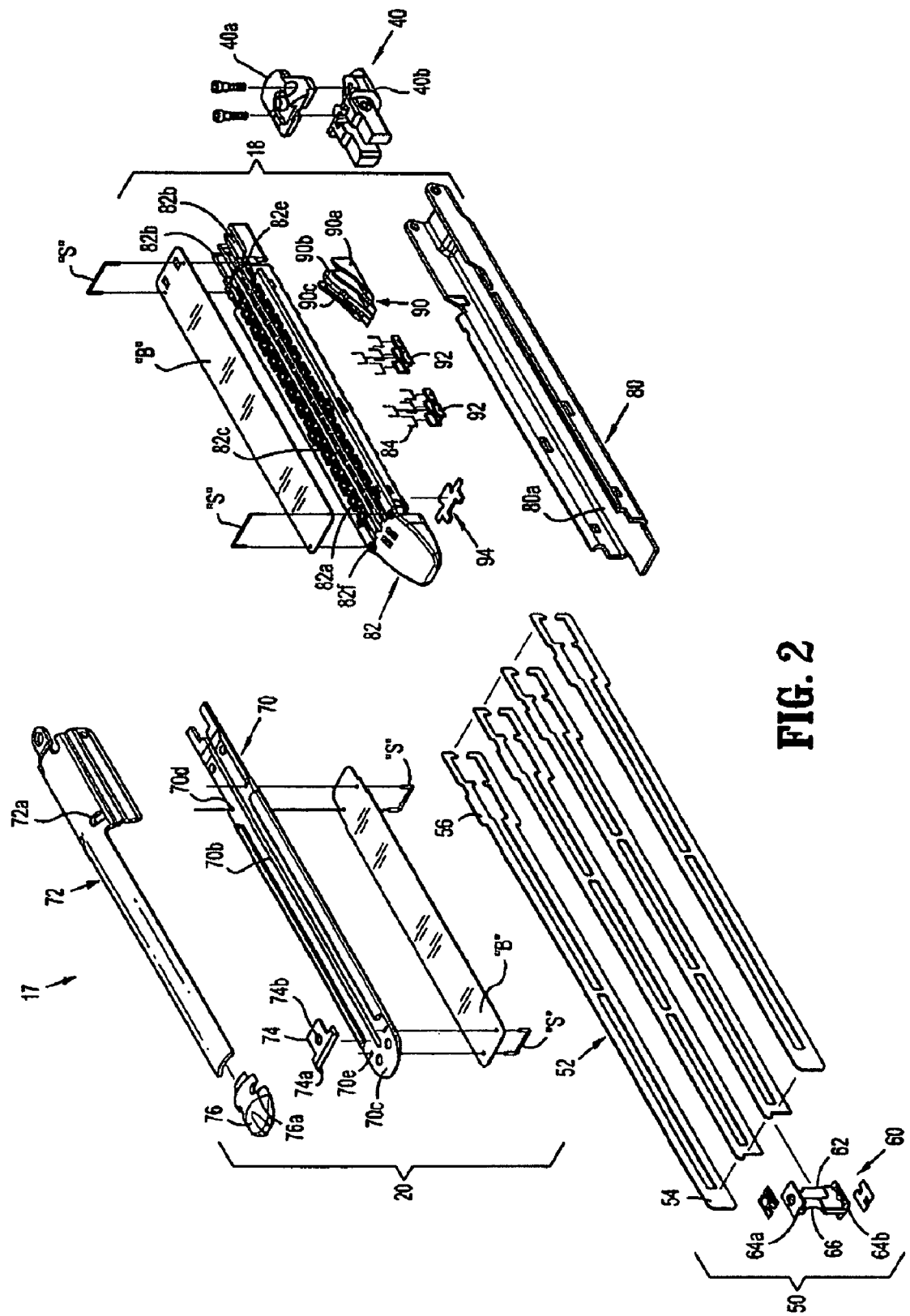
FIG. 2 is a top, exploded perspective view of a distal end of a DLU of the surgical stapling apparatus of FIG. 1.
Figure 3:
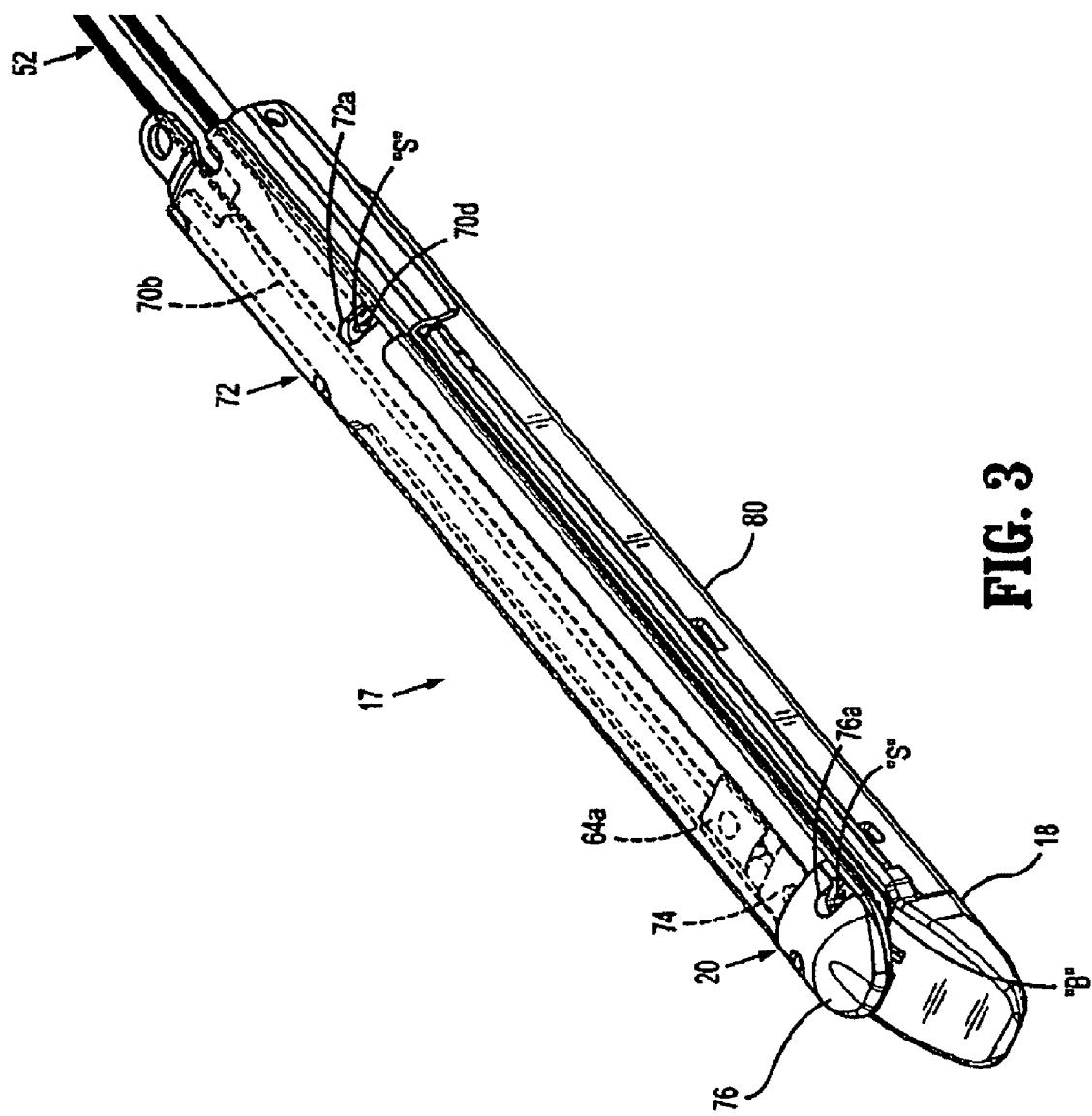
FIG. 3 is a top, perspective view of the DLU of FIG. 2, shown in an assembled condition.
Figure 4:
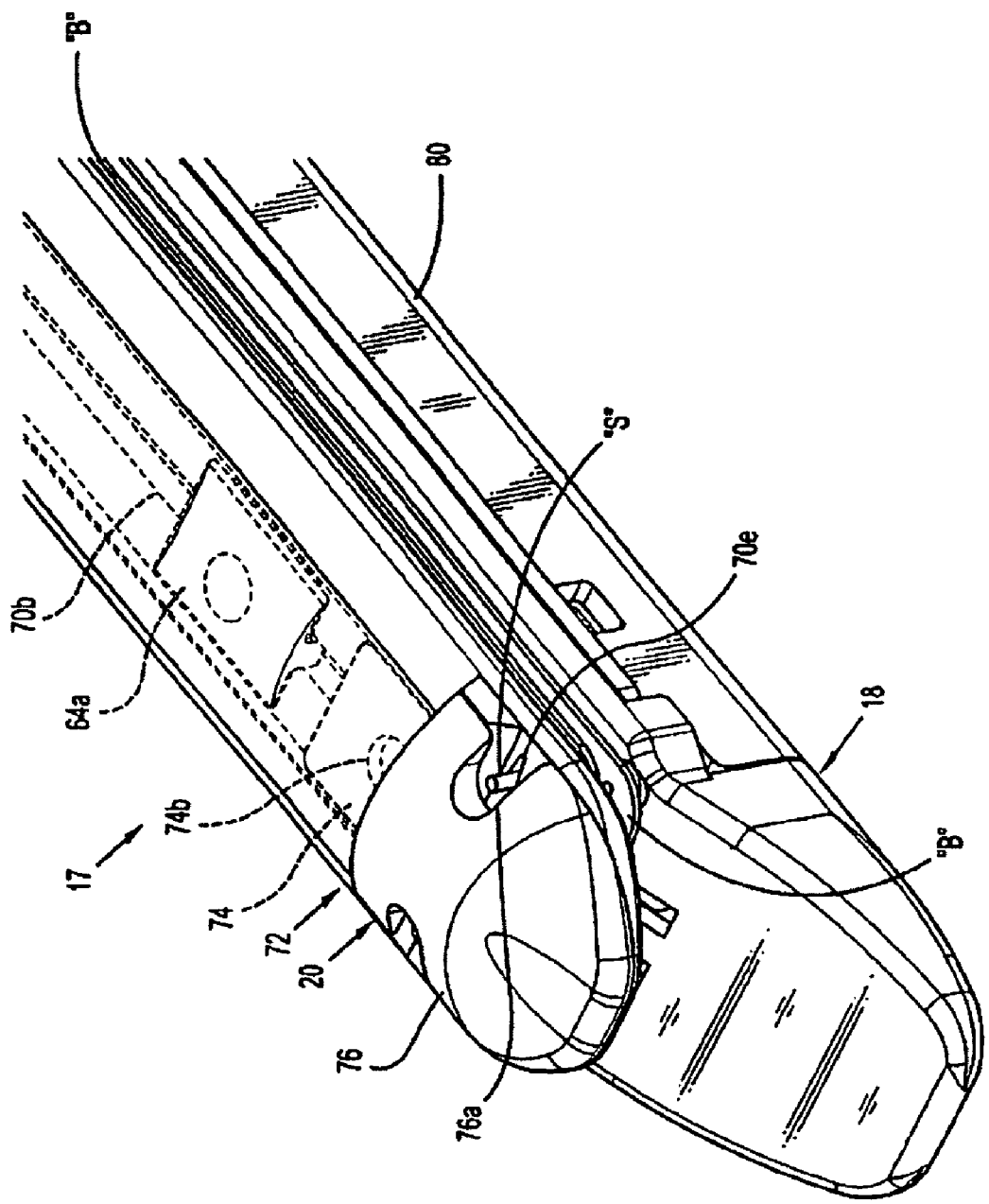
FIG. 4 is a top, perspective view of a distal end of the DLU of FIG. 2.
Figure 5:
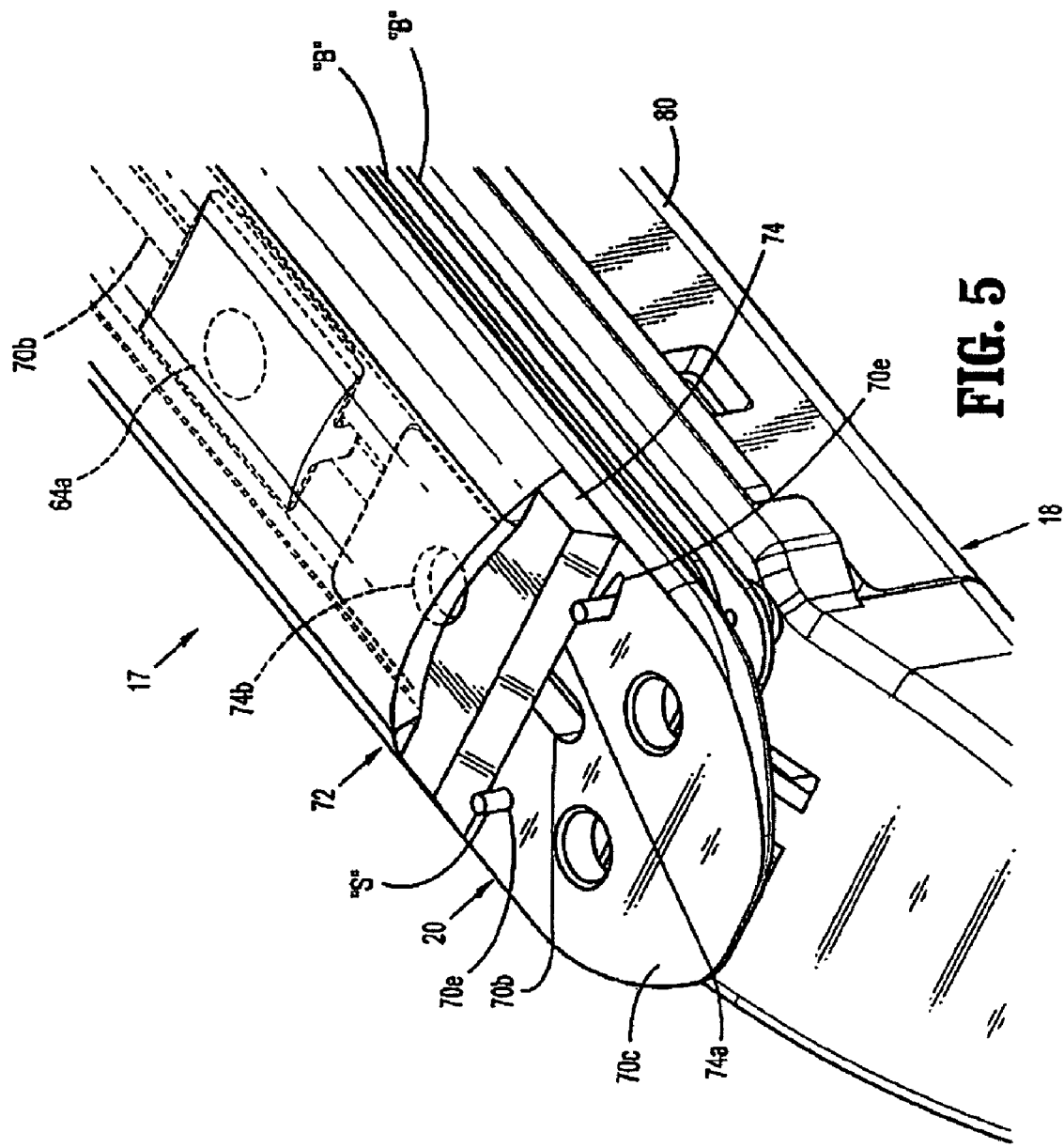
FIG. 5 is a further top, perspective view of the distal end of the DLU of FIGS. 2 and 4, having a top, front cover removed therefrom.
Figure 6:
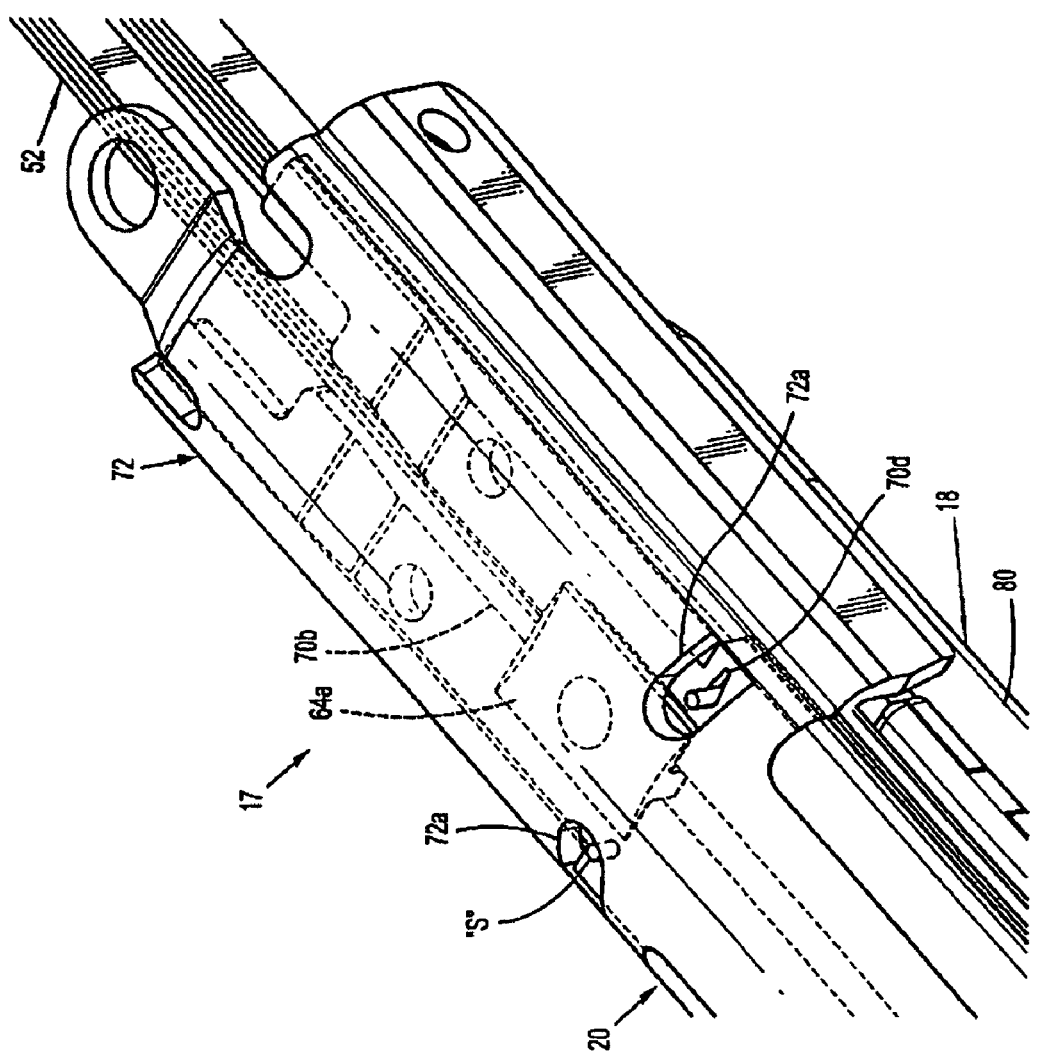
FIG. 6 is a top, perspective view of a proximal end of the DLU of FIGS. 2-5.
Figure 7:
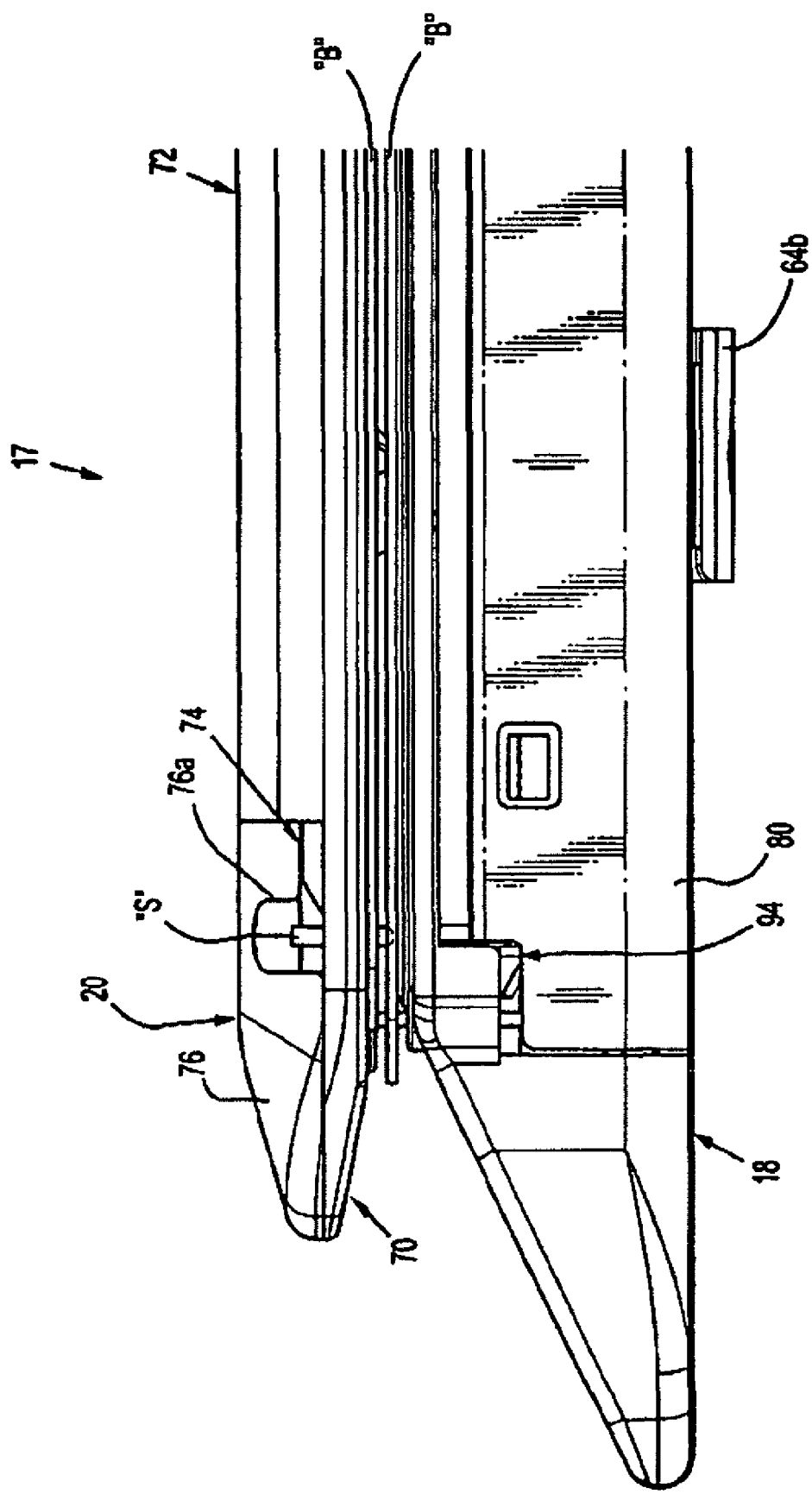
FIG. 7 is a side, elevational view of the distal end of the DLU of FIGS. 2-6.
Figure 8:
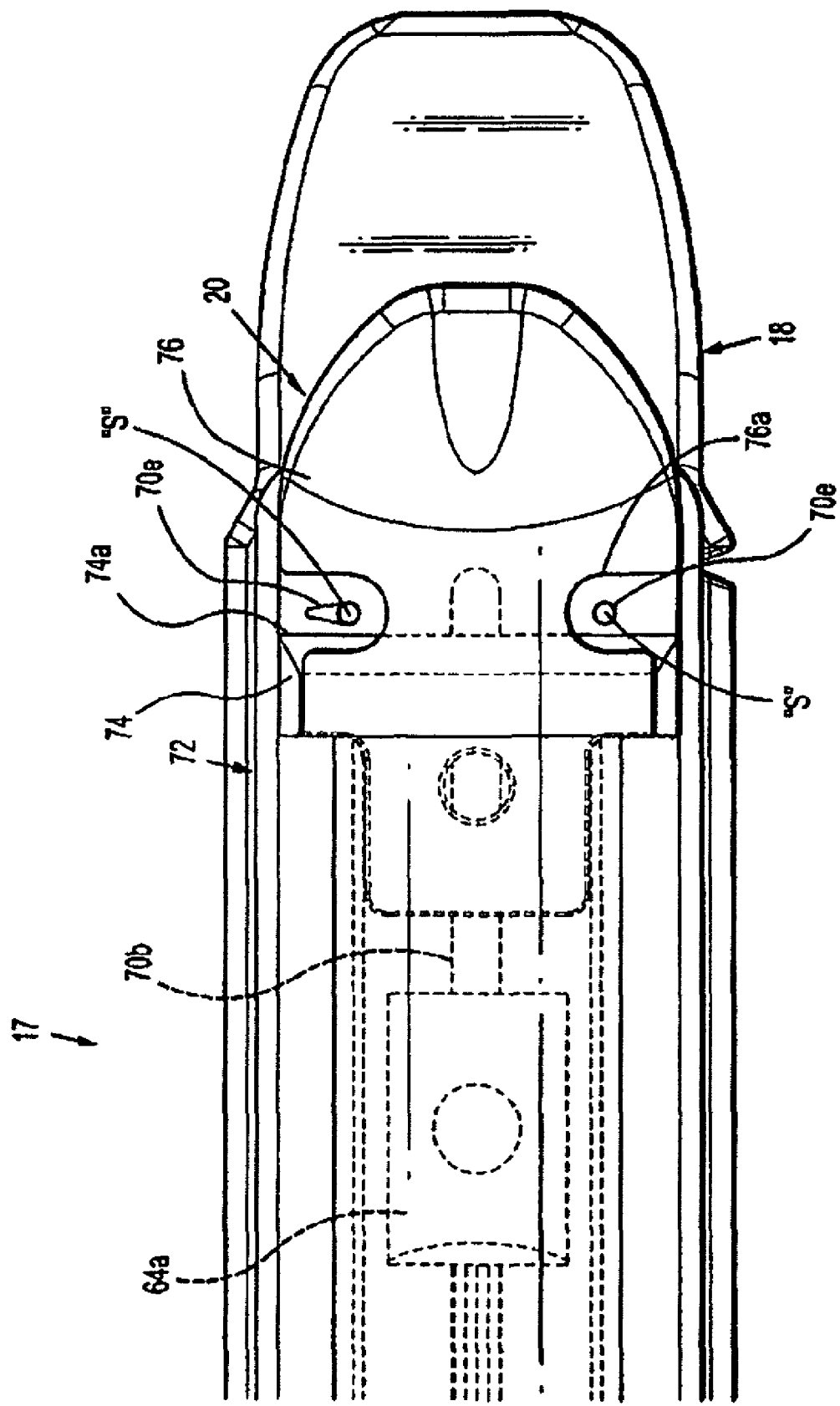
FIG. 8 is a top, plan view of the distal end of the DLU of FIGS. 2-7.
Figure 9:
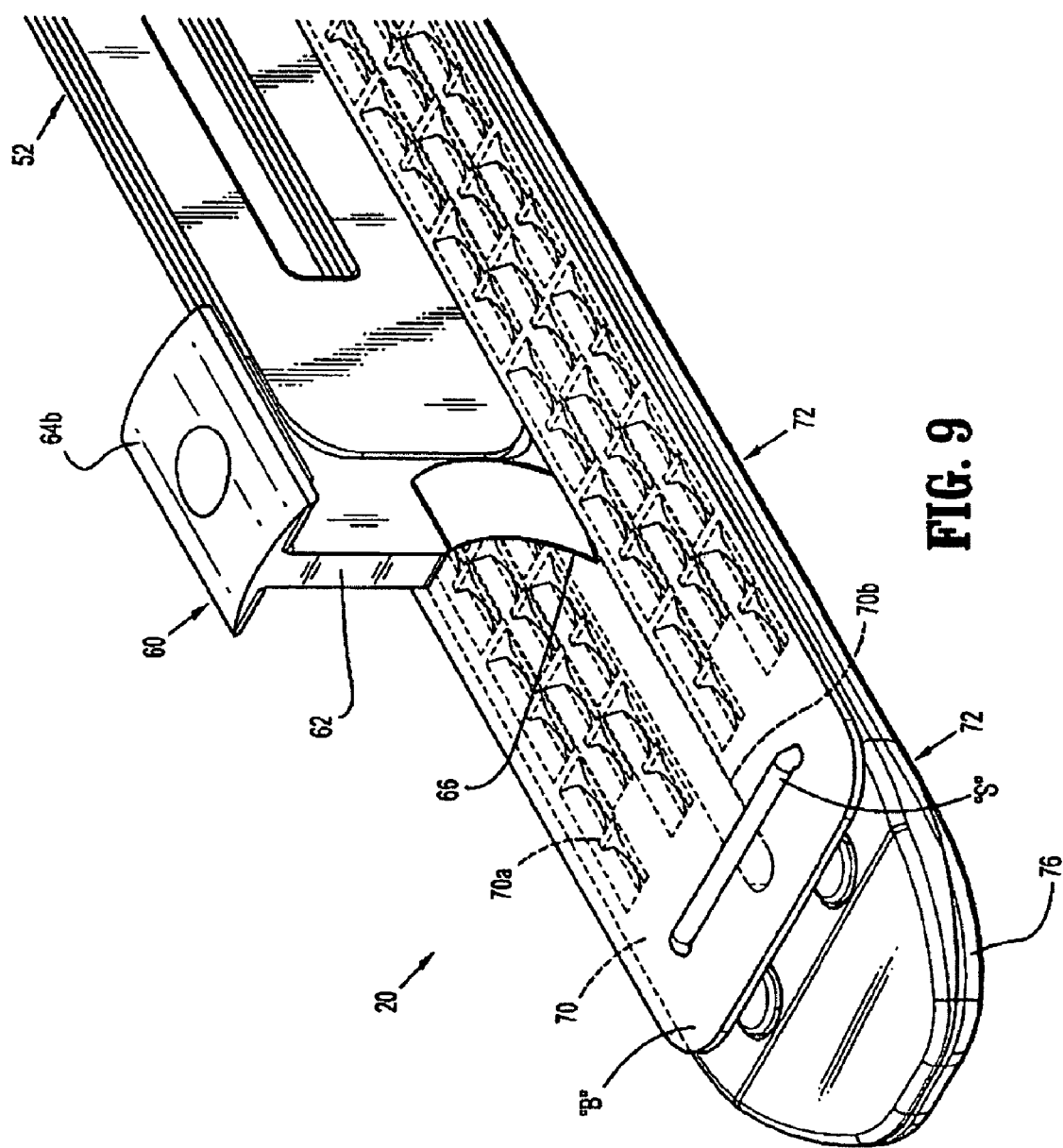
FIG. 9 is a bottom, perspective view of a distal end of an anvil half-section of the DLU of FIGS. 2-8, illustrating a knife assembly associated therewith.
Figure 10:
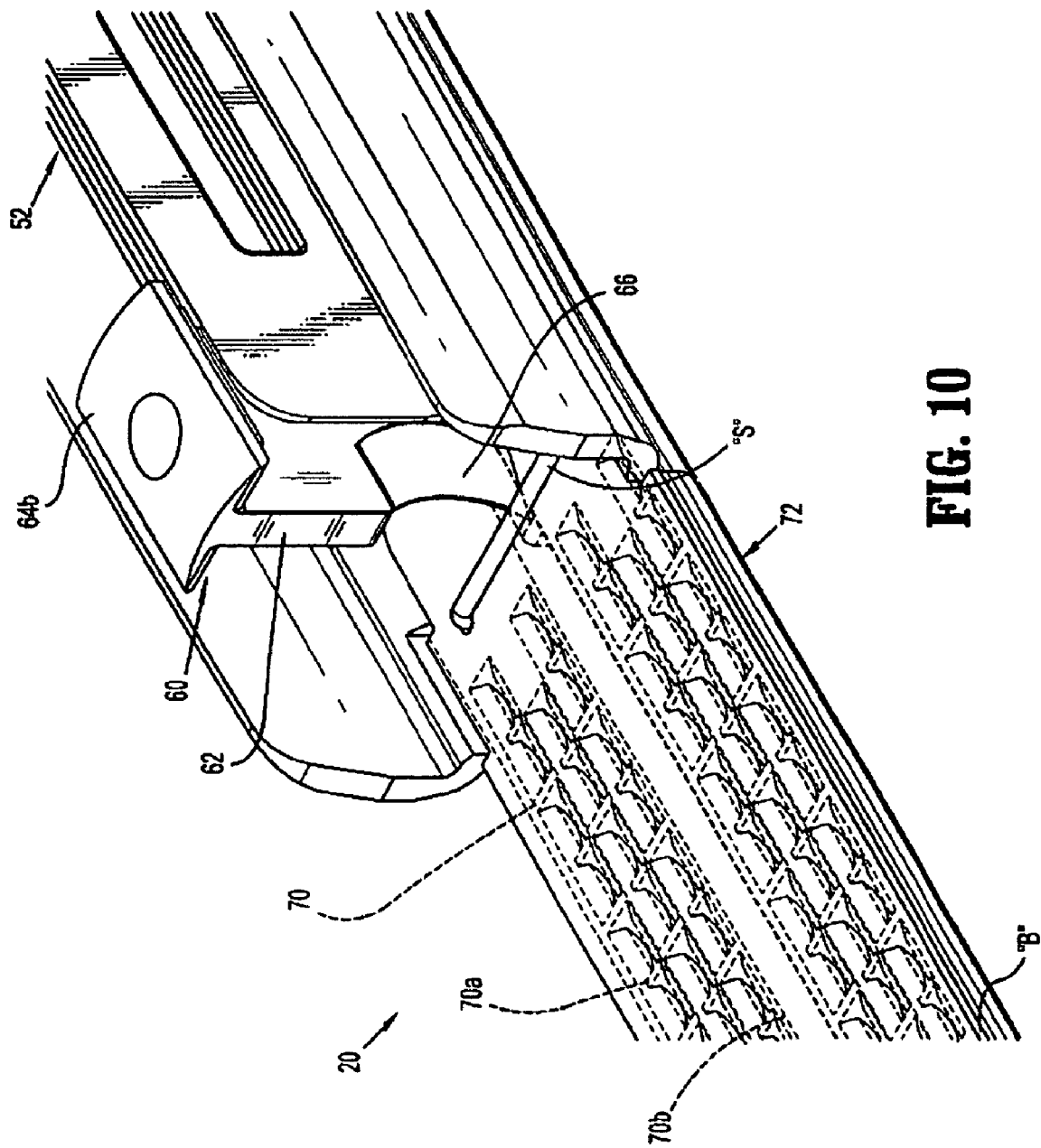
FIG. 10 is a bottom, perspective view of a proximal end of the anvil half-section of FIG. 9, illustrating the knife assembly associated therewith.
Figure 11:
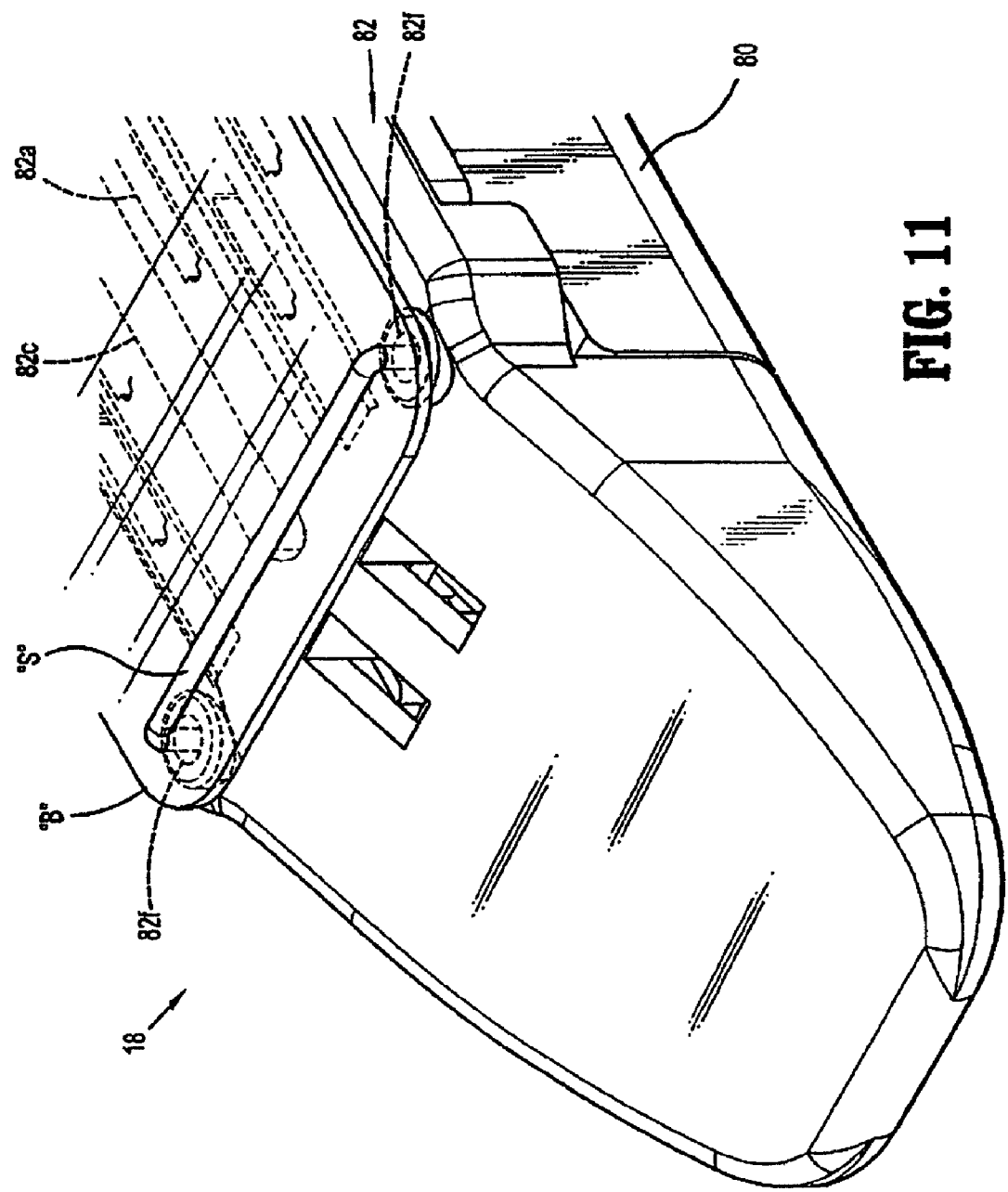
FIG. 11 is a top, perspective view of a distal end of a cartridge half-section of the DLU of FIG. 2.
Figure 12:
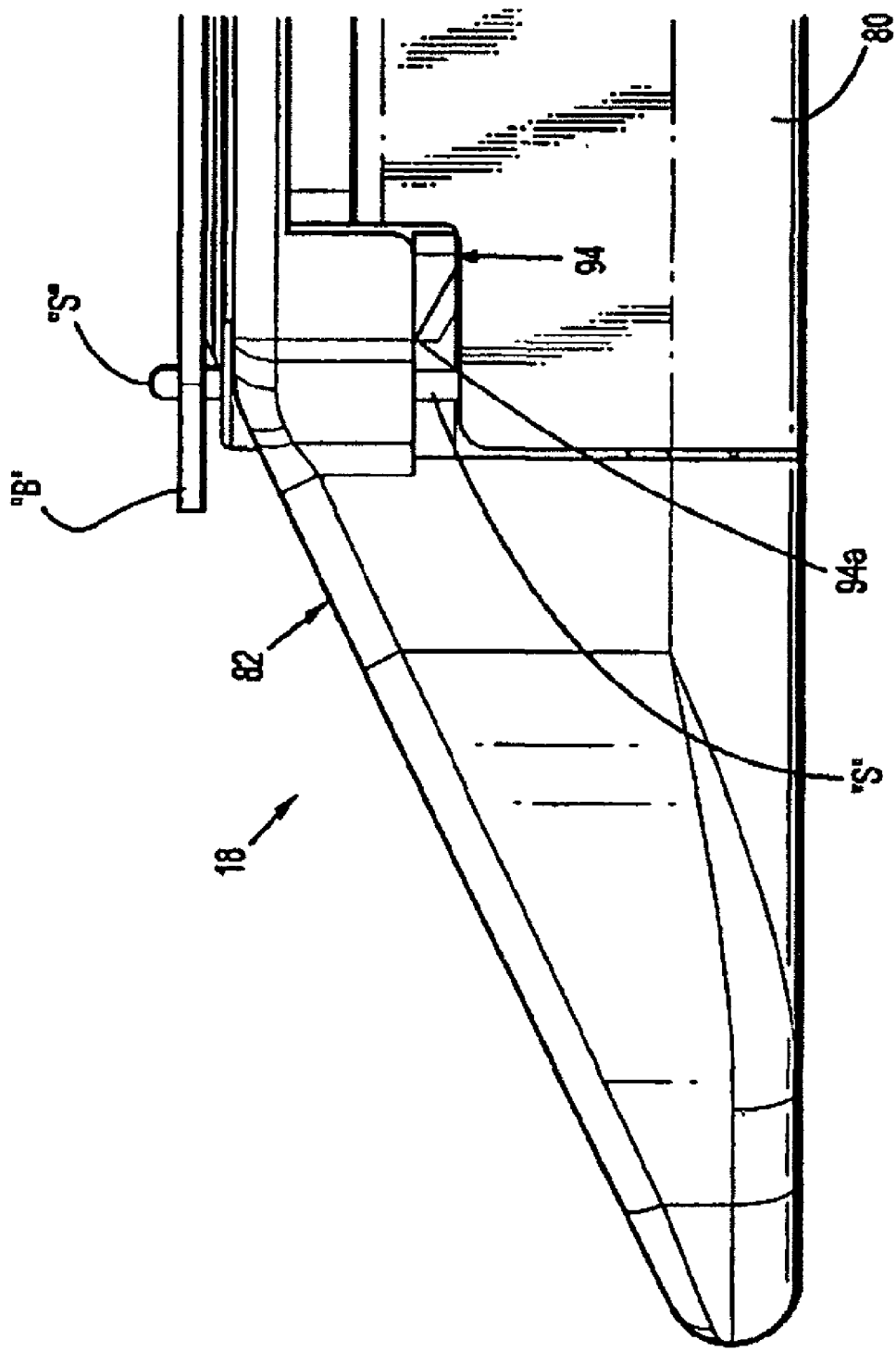
FIG. 12 is a side, elevational view of the distal end of the cartridge half-section of the DLU of FIGS. 2 and 11
Figure 13:
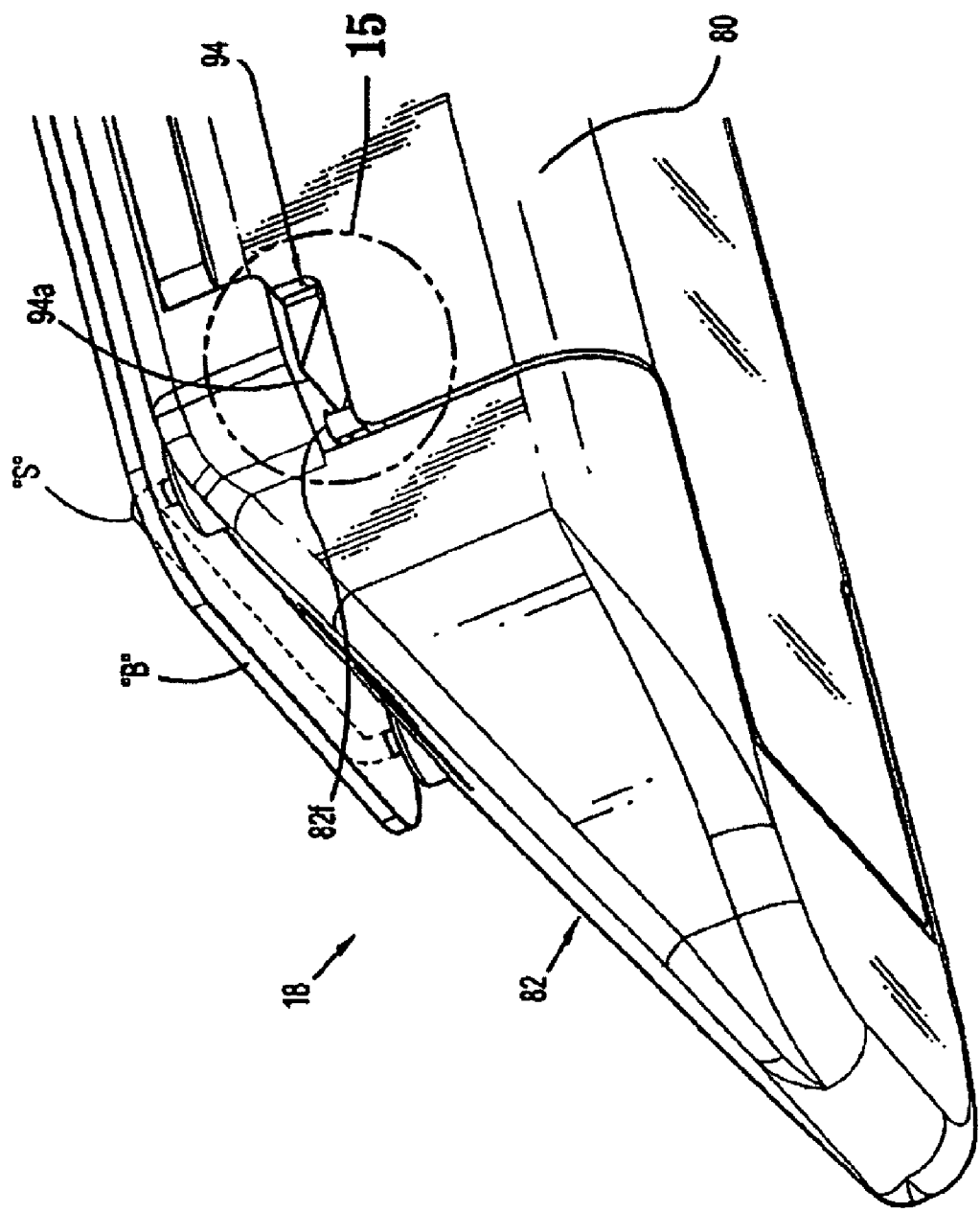
FIG. 13 is a bottom, perspective view of the distal end of the cartridge half-section of the DLU of FIGS. 2, 11 and 12.
Figure 14:
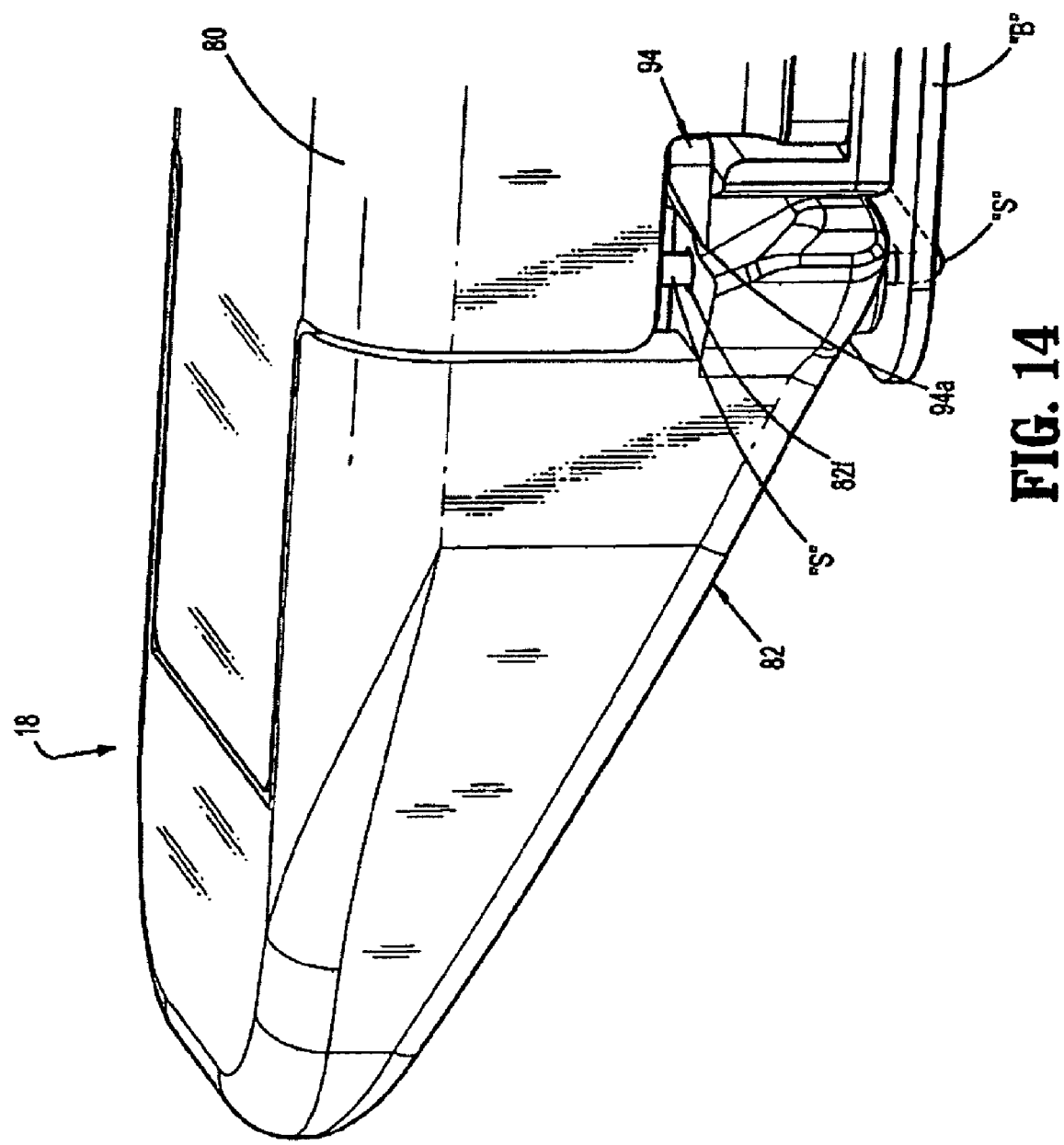
FIG. 14 is a further bottom, perspective view of the distal end of the cartridge half-section of the DLU of FIGS. 2 and 11-13.
Figure 15:
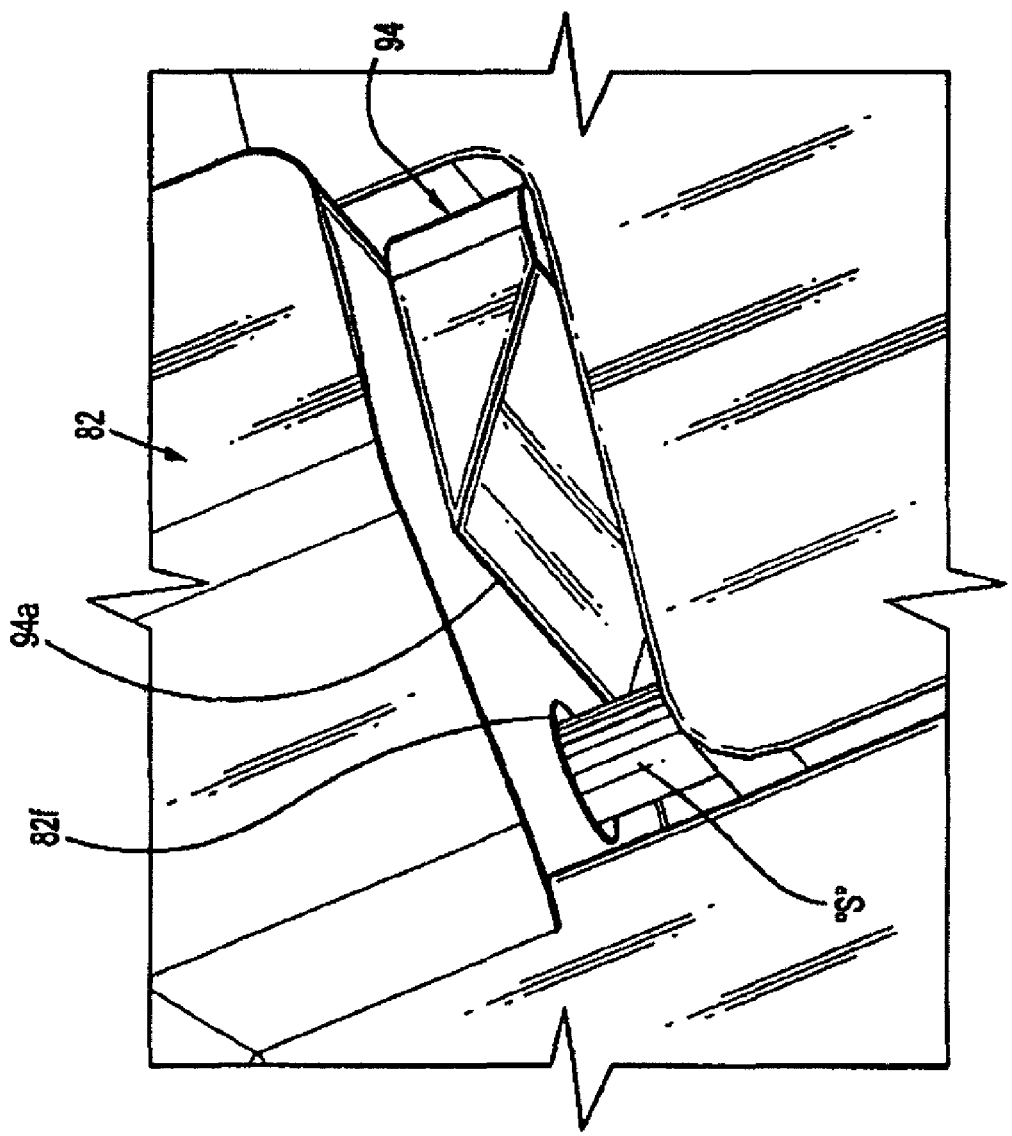
FIG. 15 is an enlarged, perspective view of the indicated area of detail of FIG. 13.
Figure 16:
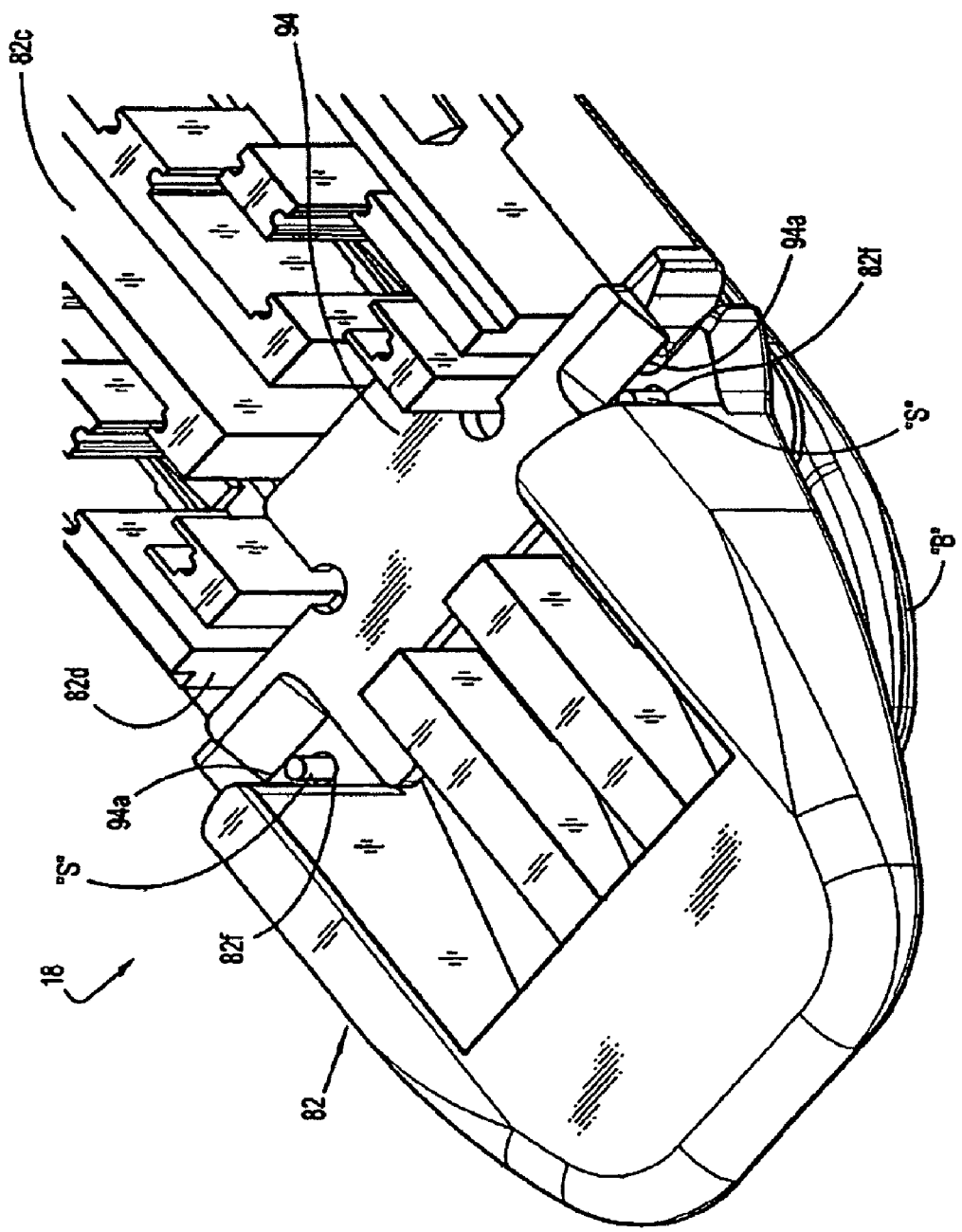
FIG. 16 is a bottom, enlarged, perspective view of the distal end of the cartridge half-section of the DLU of FIGS. 2 and 11-15.
Figure 17:
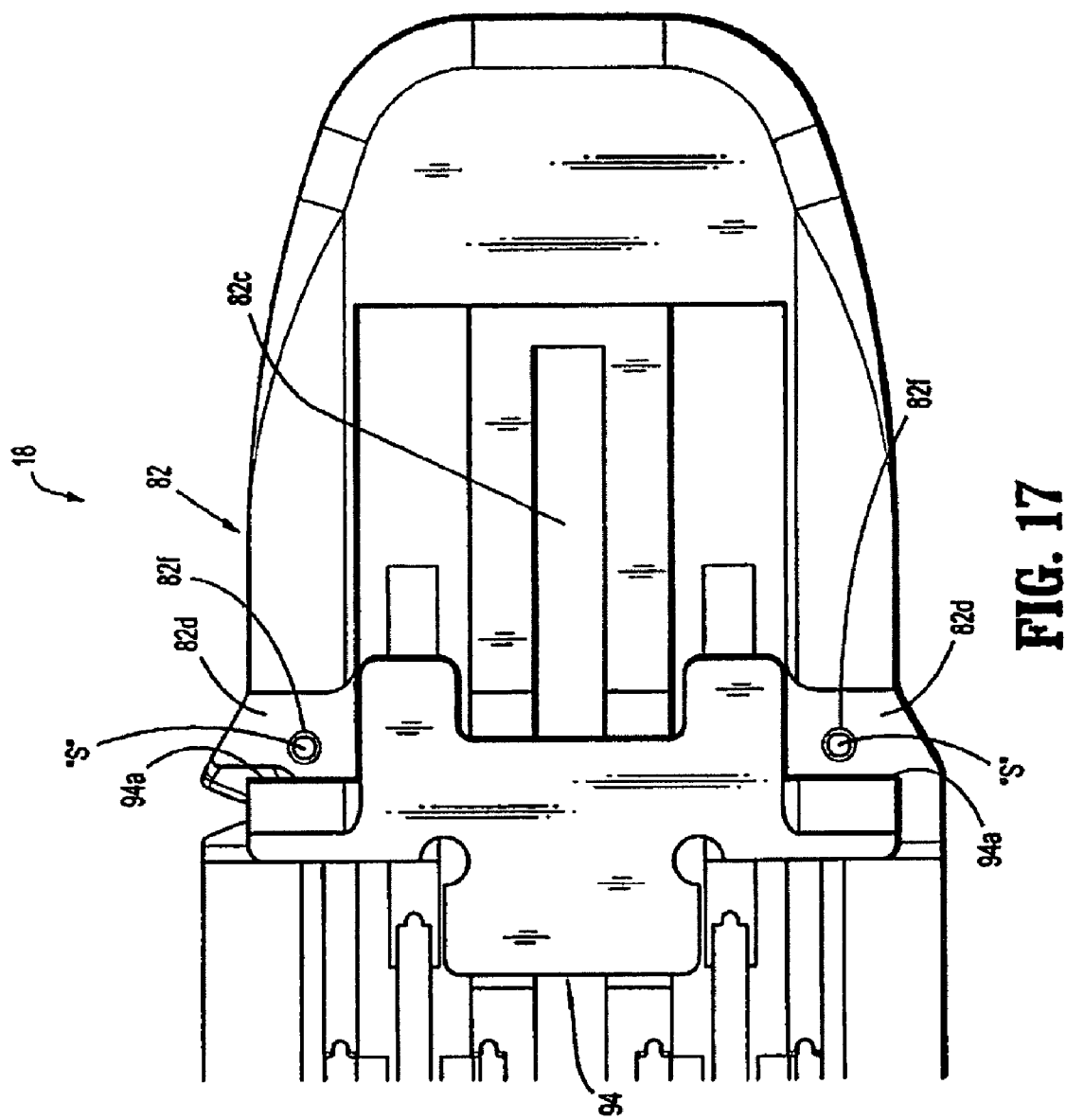
FIG. 17 is a bottom, plan view of the distal end of the cartridge half-section of the DLU of FIGS. 2 and 11-16.

An axial drive assembly 50 is operatively associated with and slidably disposed between cartridge and/or anvil assembly 18, 20. With reference to FIG. 2, axial drive assembly 50 includes an elongated drive beam 52 having a distal end 54 and a proximal end 56. Drive beam 52 may be constructed from a single sheet of material or, preferably, multiple stacked sheets.

Proximal end 56 of drive beam 52 of drive assembly 50 includes a pair of resilient engagement fingers which are dimensioned and configured to mountingly engage a drive member, e.g., a drive rod or control rod (not shown) when the proximal end of DLU 16 is engaged with elongated body 14 of surgical stapling apparatus 10. The control rod functions to impart axial movement of drive assembly 50 from handle assembly 12.

Distal end 54 of drive beam 52 of drive assembly 50 is configured and adapted to support an I-Beam 60. I-beam 60 includes a central wall portion 62 and an upper and lower rail portion 64a, 64b, respectively. A distal edge of central wall portion 62 defines a knife blade or the like 66.

As seen in FIGS. 2-10, anvil assembly 20 includes an anvil plate 70 having a plurality of staple deforming pockets/cavities 70a (see FIGS. 9 and 10) and a cover plate 72 secured to a top surface of anvil plate 70, wherein a cavity (not shown) is defined therebetween. The cavity defined between anvil plate 70 and cover plate 72 is dimensioned to slidably receive upper rail portion 64a of I-beam 60 therein. A longitudinal slot 70b extends through anvil plate 70 to facilitate passage of central wall portion 62 of I-beam 60 therethrough.

In operation, an upper surface of anvil plate 70 defines a camming surface 70c against which upper rail portion 64a of I-beam 60 engages to cam, urge and clamp anvil assembly 20 against the tissue as drive assembly 50 advances I-beam 60 through longitudinal slot 70b.

With continued reference to FIGS. 2-10, anvil plate 70 defines a proximal pair of recesses 70d formed near a proximal end of anvil plate 70 and disposed, one each, on opposed sides of longitudinal slot 70b. Anvil plate 70 defines a distal pair of recesses 70e formed near a distal end of anvil plate 70 and disposed, one each, on opposed sides of longitudinal slot 70b. In one embodiment, at least one of the recesses of each of the proximal pair of recesses 70d and the distal pair of recesses 70e is non-circular, preferably, constricting, so as to frictionally engage and/or pinch an anchor "S".

As used herein the term anchor is understood to include and is not limited to suture, thread, tether, strap, band, line, wire, cable, fastener, tack, anchor or any other material suitable for the intended purpose disclosed herein.

Anvil assembly 20 further includes a knife blade 74 defining a distally oriented knife edge 74a and being operatively interposed within the cavity defined between anvil plate 70 and cover plate 72. Knife blade 74 has an initial or first condition positioned proximal of the distal pair of recesses 70e and a final or second condition positioned distal of the distal pair of recesses 70e. Knife blade 74 includes an engaging element 74b, e.g., a recess, formed in a surface thereof for selectively engaging a complementary engaging element, e.g., nub, (not shown) projecting from a surface of cover plate 72, or a distal cap 76 of anvil assembly 20. The engaging elements inter-engage with one another to maintain or hold knife blade 74 stationary and in the initial or first condition.

In an embodiment distal cap 76 includes a pair of opposed recesses 76a formed in opposed side edges thereof which align with the distal pair of recesses 70e formed in anvil plate 70 when cover plate 72 is assembled with anvil plate 70. Additionally, cover plate 72 defines a pair of opposed recesses 72a formed therein which align with the proximal pair of recesses 70d formed in anvil plate 70 when cover plate 72 is assembled with anvil plate 70.

Anvil assembly 20 further includes a surgical buttress "B", pledget or the like operatively secured to a lower surface of anvil plate 70, by anchor "S", to overlie at least some of anvil pockets 70a and/or at least a portion of a length of longitudinal slot 70b. In particular, an anchor "S" is threaded through a distal portion of the anvil buttress "B" and each of the distal pair of recesses 70e, and an anchor "S" is threaded through a proximal portion of anvil buttress "B" and each of the proximal pair of recesses 70d.

In one particular embodiment, a first end of a anchor "S" includes a knot, stop or the like (not shown) sized so as to not pass through one recess of the proximal pair of recesses 70d while a second end of anchor "S" passes through, and transversely across, anvil buttress "B", at least once, and back through the other recess of the proximal pair of recesses 70d. For example, the second end of anchor "S" may be pinched or cinched in the other recess of the proximal pair of recesses 70d so as to anchor the second end of the anchor "S" and secure the anvil buttress "B" against the lower surface of anvil plate 70. Similarly, an anchor "S" is used to extend transversely across anvil buttress "B" and into engagement with the distal pair of recesses 70e.

In operation, as will be discussed in greater detail below, with anvil buttress "B" secured against the lower surface of anvil plate 70, during firing of surgical stapling apparatus 10, as drive assembly 50 is advanced (i.e., moved from a proximal-most position to a distal-most position), knife blade 66 slices through a central section of the proximal anchor "S", thereby freeing the proximal end of the anvil buttress "B" from anvil assembly 20. As drive assembly 50 approaches the distal end of anvil plate 70, upper rail 64a of I-beam 60 abuts against and urges knife blade 74 distally. As knife blade 74 is moved distally, from the initial or first condition positioned proximal of the distal pair of recesses 70e to the final or second condition positioned distal of the distal pair of recesses 70e, knife edge 74a thereof slices or cuts through distal anchor "S", thereby freeing the distal end of the anvil buttress "B" from anvil assembly 20. Knife blade 74 cuts through the distal anchor "S" extending through both recesses of the distal pair of recesses 70e.

As seen in FIGS. 2-8 and 11-19, cartridge assembly 18 includes a carrier 80 defining an elongated support channel 80a. Elongated support channel 80a of carrier 80 is dimensioned and configured to selectively receive a staple cartridge 82 therein. Corresponding tabs and slots formed along staple cartridge 82 and carrier 80 function to retain staple cartridge 82 within carrier 80. A pair of support struts formed on and extending from staple cartridge 82 are positioned to rest on side walls of carrier 80 to further stabilize staple cartridge 82 within support channel 80a of carrier 80. Staple cartridge 82 includes retention slots 82a formed therein for receiving a plurality of fasteners 84 and pushers 86. A plurality of spaced apart longitudinal slots 82b extend through staple cartridge 82 to accommodate upstanding cam wedges 90a of actuation sled 90. Actuation sled 90 includes a central upstanding wedge or wall 90b. Central wall 90b defines a distal notch or shoulder 90c formed therein.

A central longitudinal slot 82c is formed in and extends along the length of staple cartridge 82 to facilitate passage of central wall portion 62 of I-beam 60 therethrough. During operation of surgical stapler 10, actuation sled 90 translates through longitudinal slots 82b of staple cartridge 82 to advance cam wedges 90a into sequential contact with pushers 92, to cause pushers 92 to translate vertically within retention slots 82a and urge fasteners 84 (e.g., staples) from slots 82a into the staple forming cavities 70a of anvil plate 70 of anvil assembly 20.

With continued reference to FIGS. 2 and 11-19, staple cartridge 82 defines a proximal pair of recesses 82e formed near a proximal end thereof and disposed, one each, on opposed sides of longitudinal slot 82c. Staple cartridge 82 further defines a distal pair of recesses 82f formed near a distal end thereof and disposed, one each, on opposed sides of longitudinal slot 82c. In one embodiment, at least one of the recesses of each of the proximal pair of recesses 82e and the distal pair of recesses 82f is non-circular, preferably, constricting, so as to frictionally engage and/or pinch an anchor "S".

Cartridge assembly 18 further includes a knife blade 94 defining a distally oriented knife edge 94a (see FIGS. 12-17 and 19) and being operatively disposed within a cavity 82d (see FIGS. 16, 17 and 19) defined near a distal end of staple cartridge 82. Knife blade 94 may include a right side and a left side knife edge 94a. Knife blade 94 has an initial or first condition positioned proximal of a distal pair of recesses 82e formed in staple cartridge 82 and a final or second condition positioned distal of the distal pair of recesses 82e.

Knife blade 94 may include an engaging element (not shown) formed in a surface thereof for selectively engaging a complementary engaging element (not shown) projecting from a surface of staple cartridge 82 of cartridge assembly 18. The engaging elements inter-engage with one another to maintain or hold knife blade 94 stationary and in the initial or first condition.

Cartridge assembly 18 further includes a surgical buttress "B", pledget or the like operatively secured to an upper surface of staple cartridge 82, by anchors "S", to overlie at least some of staple pockets 82a and/or at least a portion of a length of longitudinal slot 82c. In particular, an anchor "S" is threaded through a distal portion of the cartridge buttress "B" and each of the distal pair of recesses 82f, and an anchor "S" is threaded through a proximal portion of cartridge buttress "B" and each of the proximal pair of recesses 82e.

In one particular embodiment, a first end of each anchor "S" includes a knot, stop or the like (not shown) sized so as to not pass through one recess of the proximal pair of recesses 82e and a second end of each anchor "S" passes through, and transversely across, cartridge buttress "B", at least once, and back through the other recess of the proximal pair of recesses 82e. For example, the second end of each anchor "S" may be pinched or cinched in the other recess of the proximal pair of recesses 82e so as to anchor the second end of the anchor "S" and secure the cartridge buttress "B" against the tissue contacting surface of staple cartridge 82. Similarly, an anchor "S" is used to extend transversely across cartridge buttress "B" and into engagement with the distal pair of recesses 82f.

Figure 18:
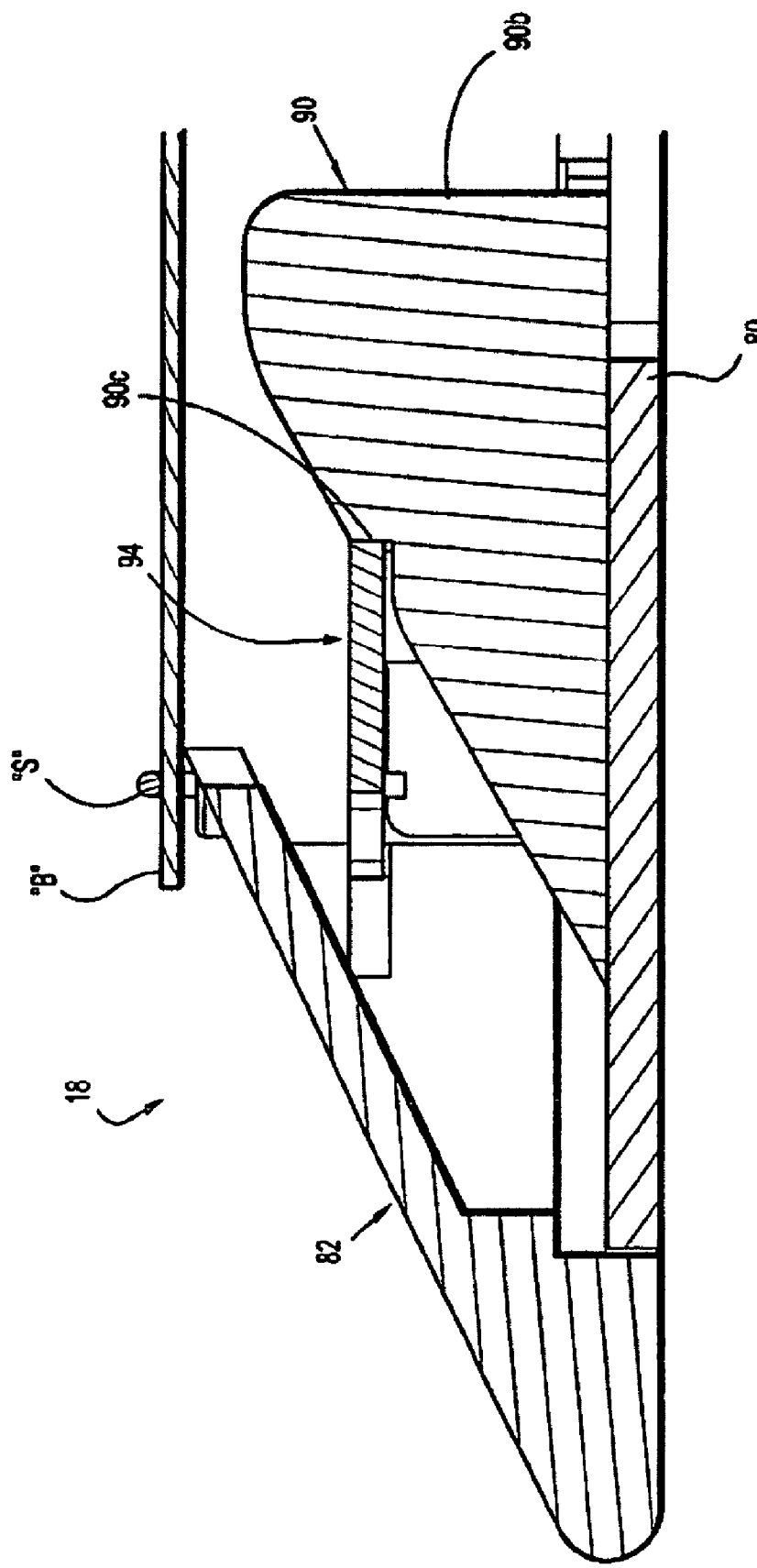
FIG. 18 is a longitudinal, cross-sectional view of the distal end of the cartridge half-section of the DLU of FIGS. 2 and 11-17.
Figure 19:
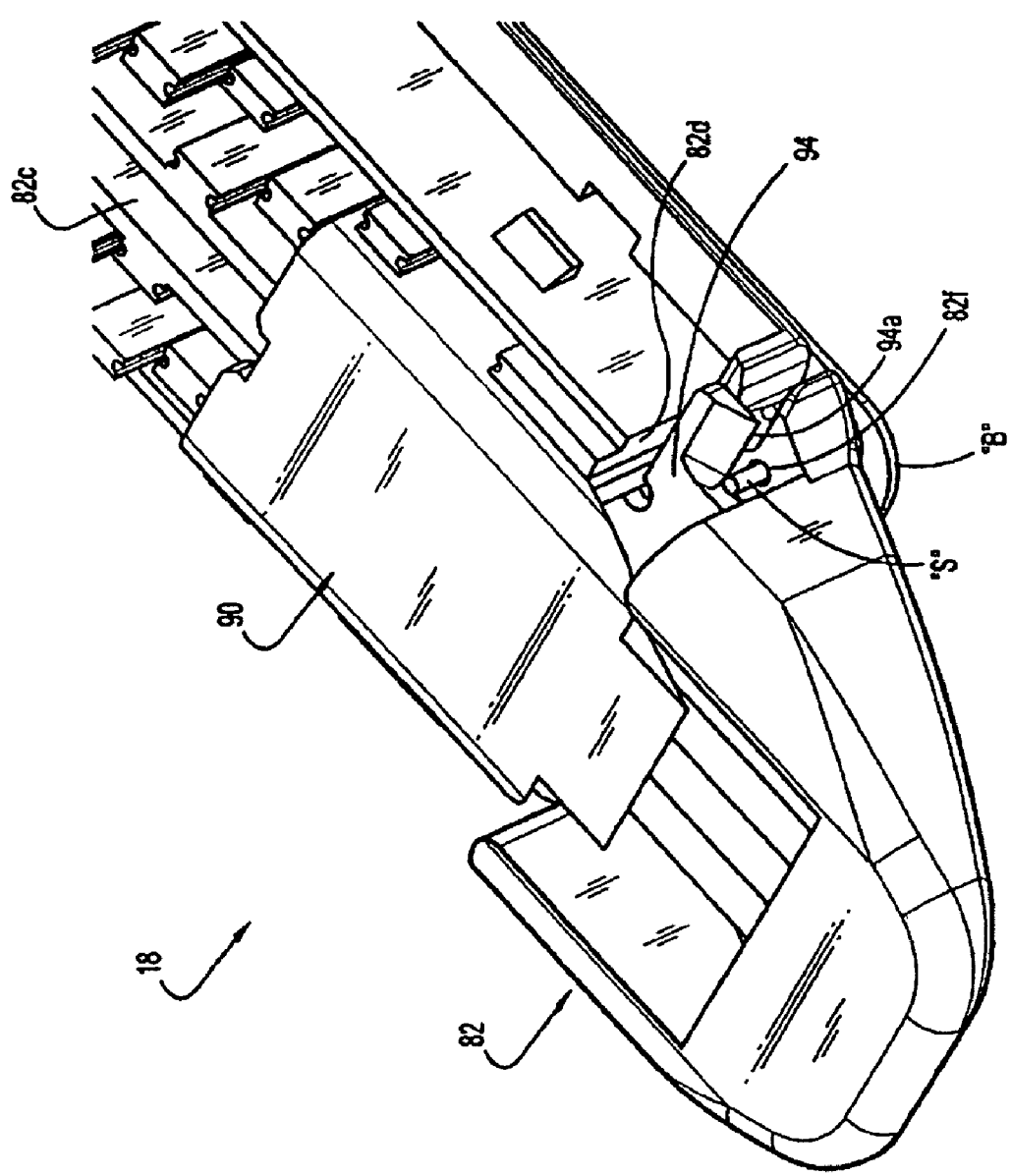
FIG. 19 is a bottom, perspective view of the distal end of the cartridge half-section of the DLU of FIGS. 2 and 11-18.

In operation, as will be discussed in greater detail below, with cartridge buttress "B" secured against the tissue contacting surface of staple cartridge 82, during firing of surgical stapling apparatus 10, as drive assembly 50 is advanced (i.e., moved from a proximal-most position to a distal-most position), knife blade 66 slices through a central section of the proximal anchor "S", thereby freeing the proximal end of the cartridge buttress "B" from cartridge assembly 18. As seen in FIG. 18, as drive assembly 50 approaches the distal end of staple cartridge 82, shoulder 90c of central upstanding wedge or wall 90b of actuation sled 90 abuts against and urges knife blade 94 distally. As knife blade 94 is moved distally, from the initial or first condition positioned proximal of the distal pair of recesses 82f to the final or second condition positioned distal of the distal pair of recesses 82f, knife edges 94a thereof slice or cut through distal anchor "S", thereby freeing the distal end of the cartridge buttress "B" from cartridge assembly 18. Knife blade 94 cuts through the distal anchor "S" extending through both recesses of the distal pair of recesses 82f.

As drive assembly 50 is advanced from a proximal-most position to a distal-most position, knife blade 66 thereof slices or cuts longitudinally through both anvil buttress "B" and cartridge buttress "B", thereby dividing the buttresses "B" substantially in half. Additionally, as drive assembly 50 is advanced from a proximal-most position to a distal-most position, upstanding cam wedges 90a of actuation sled 90 actuates pushers 92, to cause pushers 92 to translate vertically within retention slots 82a and urge fasteners 84 from slots 82a. As fasteners 84 (e.g., staples) are urged from slots 82a of staple cartridge 82, legs of fasteners 84 penetrate and pass through both anvil buttress "B" and cartridge buttress "B", through any tissue (not shown) interposed between anvil buttress "B" and cartridge buttress "B", and are formed against or within staple forming cavities 70a of anvil plate 70 of anvil assembly 20.

According to the present disclosure, anvil buttress "B" and/or cartridge buttress "B" is pre-loaded (i.e., from the manufacturer) onto anvil assembly 20 or cartridge assembly 18, respectively, of DLU 17. Additional or replacement buttresses "B" for anvil assembly 20 and/or cartridge assembly 18 may be secured to either anvil assembly 20 or cartridge assembly 18 as needed or desired.

In operation, with DLU 17 coupled to a distal end of elongated body 14 of surgical stapling apparatus 10, and with anvil buttress "B" and cartridge buttress "B" pre-loaded onto anvil assembly 20 and cartridge assembly 18, respectively, surgical stapling apparatus 10 is used in accordance with methods known by those skilled in the art. Once anvil assembly 20 and cartridge assembly 18 are clamped onto tissue, surgical stapling apparatus 10 is fired. In firing surgical stapling apparatus 10, drive assembly 50 is advanced from a proximal-most position to a distal-most position. In so doing, knife blade 66 of drive assembly 50 substantially simultaneously slices or cuts through a central section of the proximal anchor "S" of anvil assembly 20 and cartridge assembly 18, thereby respectively freeing the proximal end of anvil buttress "B" and cartridge buttress "B" therefrom.

As drive assembly 50 approaches the distal-most position, upper rail 64a of I-beam 60 abuts against and urges knife blade 74 distally while, substantially simultaneously or concomitantly therewith, shoulder 90c of central upstanding wedge or wall 90b of actuation sled 90 abuts against and urges knife blade 94 distally. As knife blade 74 is moved distally, from the initial position to the final position, knife edge 74a thereof slices or cuts through distal anchor "S" of anvil assembly 20, thereby freeing the distal end of the anvil buttress "B" from anvil assembly 20. As knife blade 94 is moved distally, from the initial position to the final position, knife edges 94a thereof slice or cut through distal anchor "S" of cartridge assembly 18, thereby freeing the distal end of the cartridge buttress "B" from cartridge assembly 18.

Also, knife blade 66 of drive assembly 50 substantially simultaneously slices or cuts longitudinally through both anvil buttress "B" and cartridge buttress "B", thereby dividing the buttresses "B" substantially in half.

Turning now to FIGS. 20-32, a DLU according to another embodiment of the present disclosure, for surgical stapling apparatus 10, is generally designated as 116. DLU 116 is substantially similar to DLU 16 and will only be discussed in detail herein to the extent necessary to identify differences in construction and operation.

Figure 22:
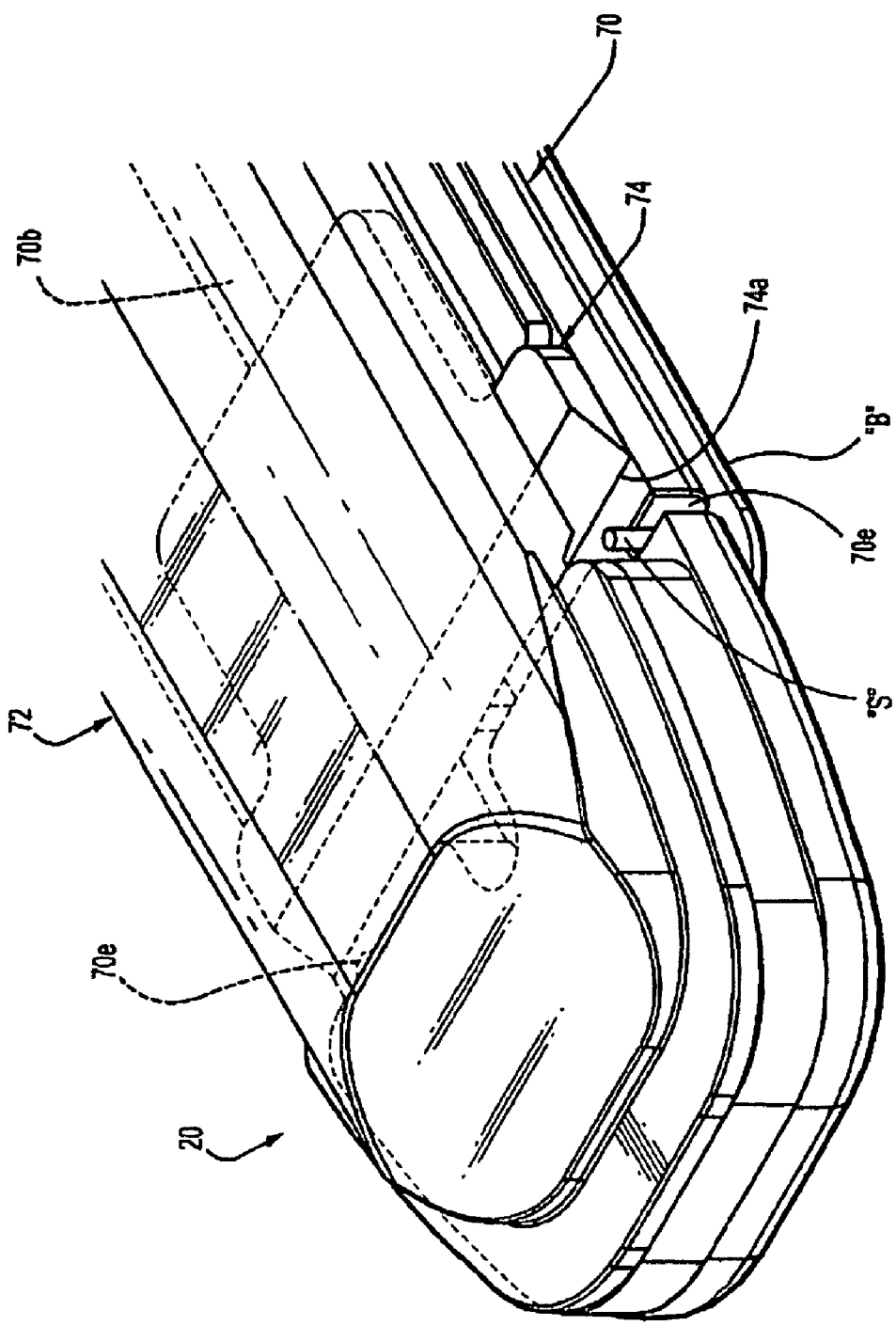
FIG. 22 is a top, perspective view of a distal end of an anvil half-section of the DLU of FIGS. 20 and 21.
Figure 23:
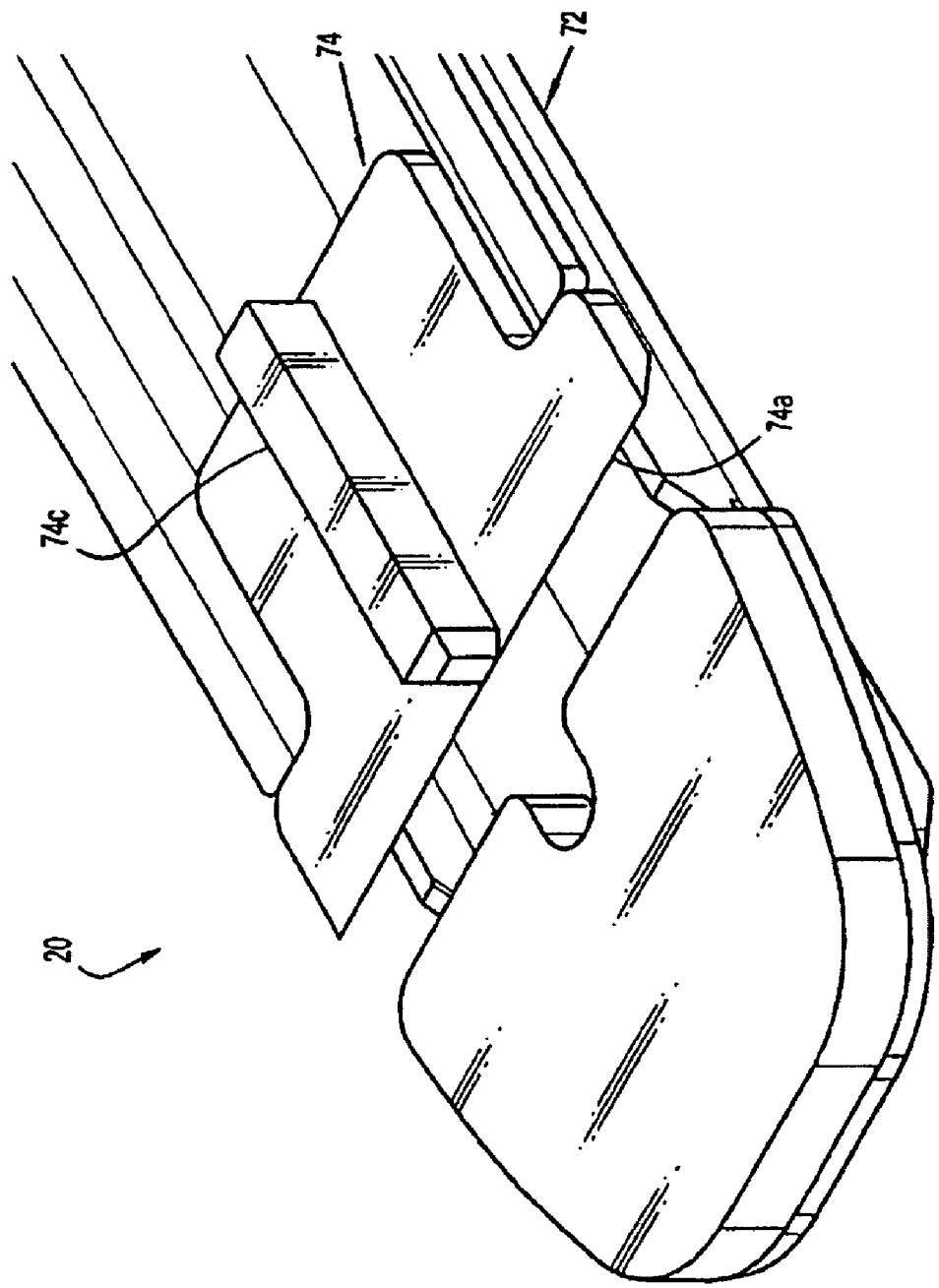
FIG. 23 is a bottom, perspective view of the distal end of the anvil half-section of FIG. 22, having an anvil plate removed therefrom.
Figure 24:
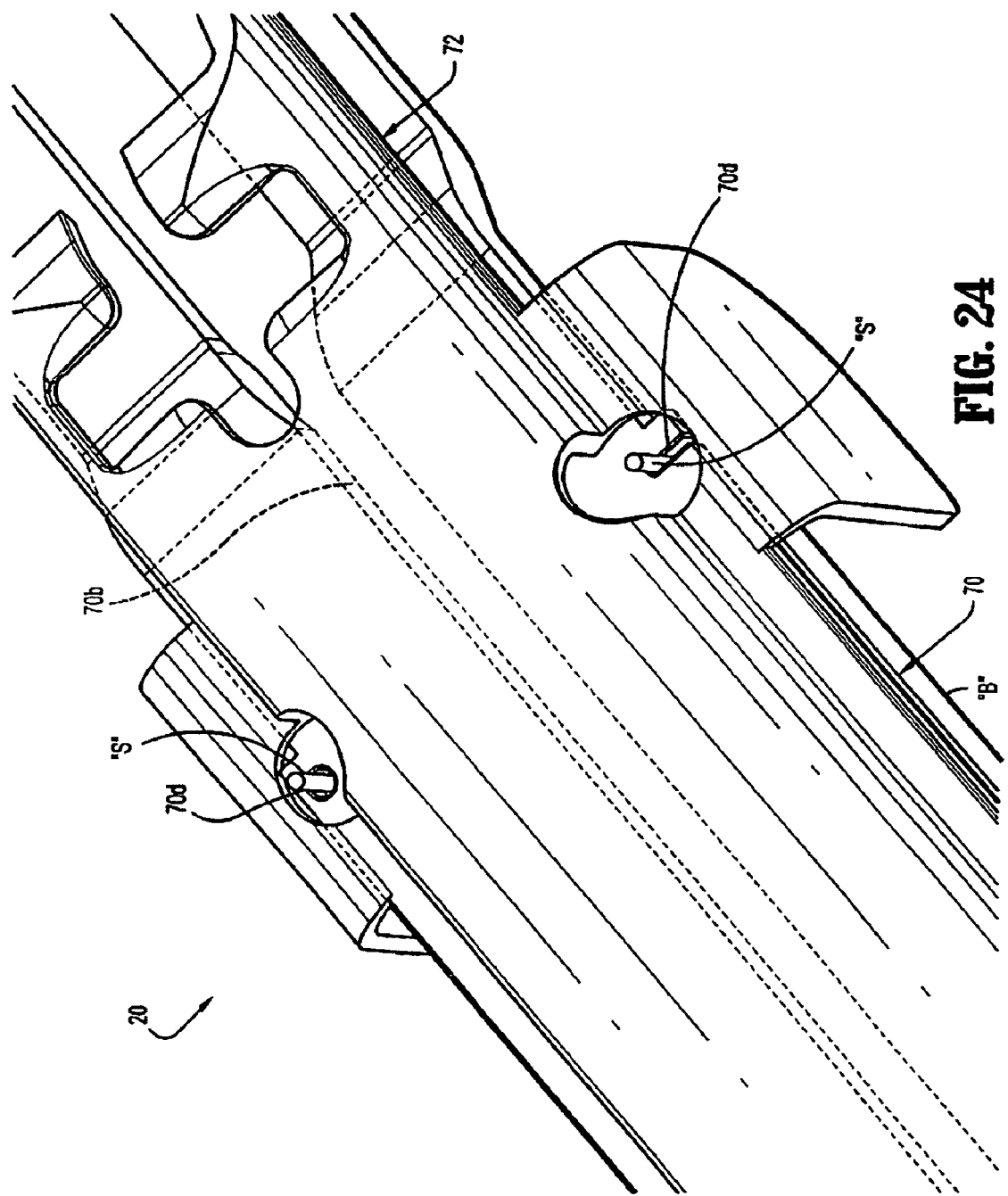
FIG. 24 is a top, perspective view of a proximal end of the anvil half-section of the DLU of FIGS. 20 and 21.
Figure 25:
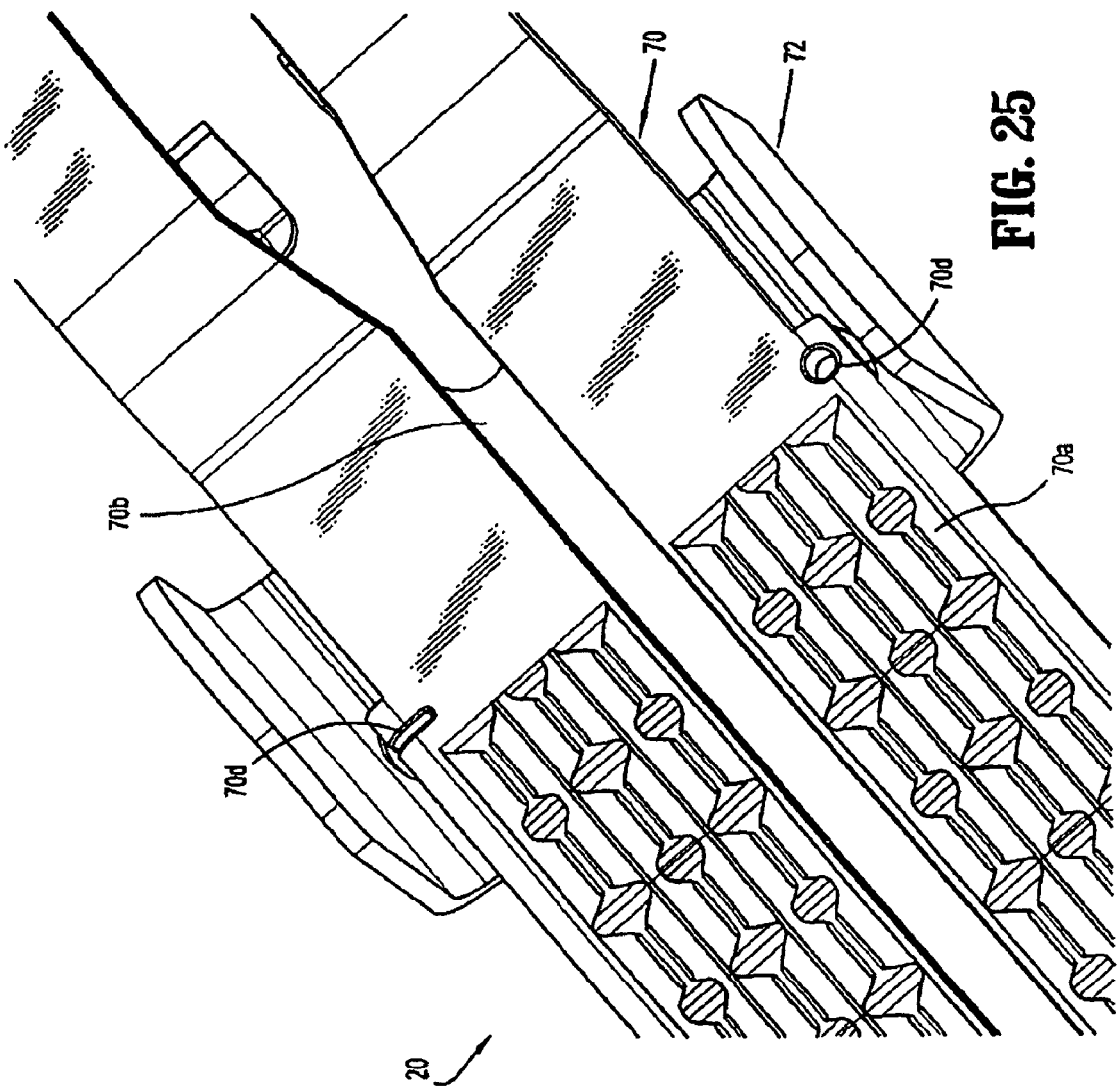
FIG. 25 is a bottom, perspective view of the proximal end of the anvil half-section of FIG. 24.

As seen in FIGS. 20-25, anvil assembly 20 of DLU 116 defines a proximal pair of recesses 70d formed near a proximal end of anvil plate 70 and disposed, one each, on opposed sides of longitudinal slot 70b; and a distal pair of recesses 70e formed near a distal end of anvil plate 70 and disposed, one each, on opposed sides of longitudinal slot 70b. As best seen in FIGS. 22, 24 and 25, at least one recess of each of the proximal pair of recesses 70d and the distal pair of recesses 70e is in the form of a notch having a constricting configuration so as to frictionally cinch, receive and secure a suture, thread or the like therein.

As seen in FIG. 23, knife blade 74 includes an orientation member 74c, in the form of a fin or tab, extending from an underside thereof and configured and adapted for slidable engagement in longitudinal slot 70b of anvil plate 70. Orientation member 74c functions to help maintain a proper or desired orientation of knife blade 74. For example, orientation member 74c of knife blade 74 may aid in maintaining knife edge 74a at a substantially orthogonal orientation with respect to longitudinal slot 70b.

As seen in FIGS. 20, 21 and 26-32, staple cartridge 82 of cartridge assembly 18 of DLU 116 defines a proximal pair of recesses 82e formed near a proximal end thereof and disposed, one each, on opposed sides of longitudinal slot 82c; and a distal pair of recesses 82f formed near a distal end thereof and disposed, one each, on opposed sides of longitudinal slot 82c.

Figure 20:
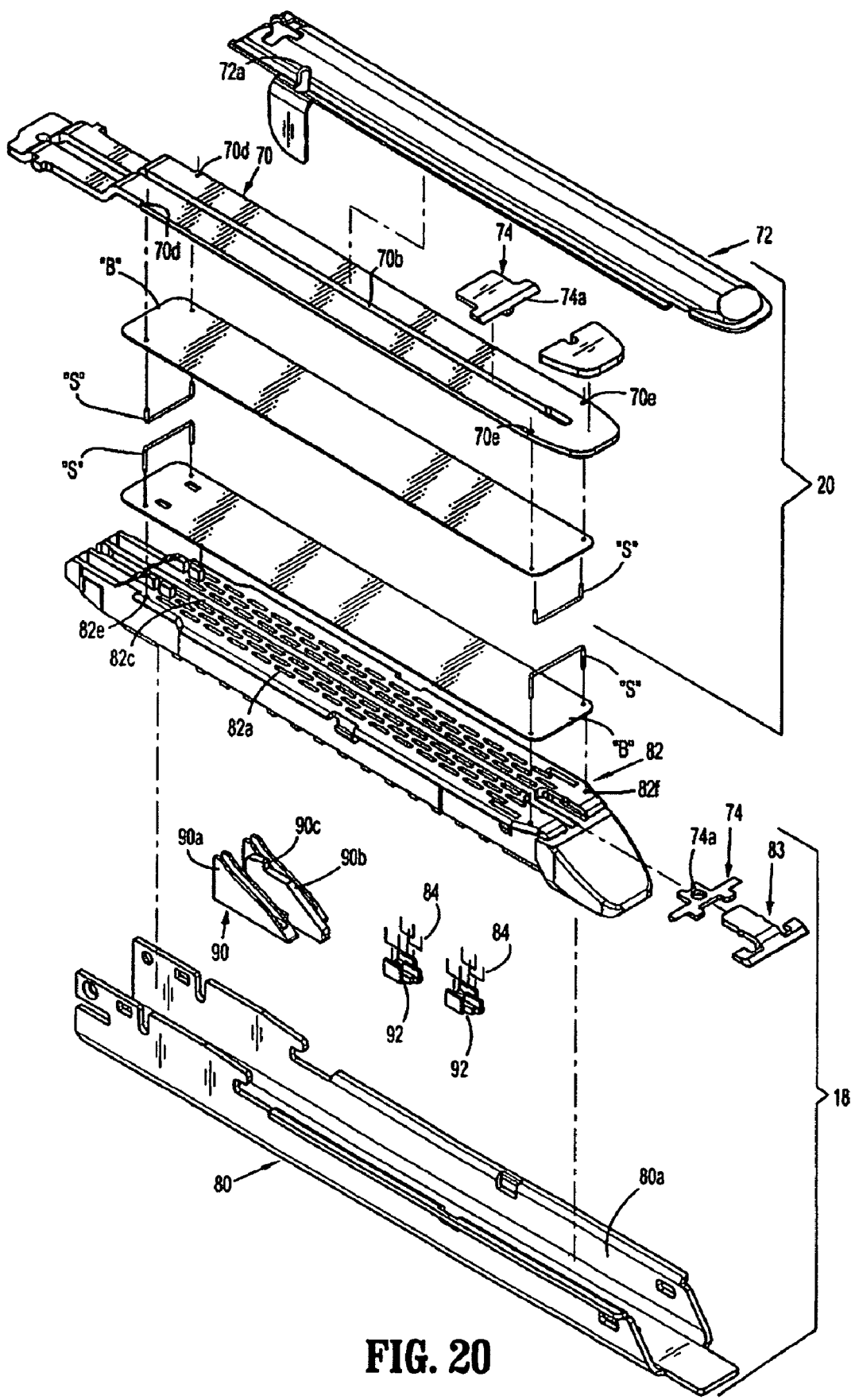
FIG. 20 is an exploded, perspective view of a distal end of a DLU of the surgical stapling apparatus of FIG. 1, according to another embodiment of the present disclosure.
Figure 21:
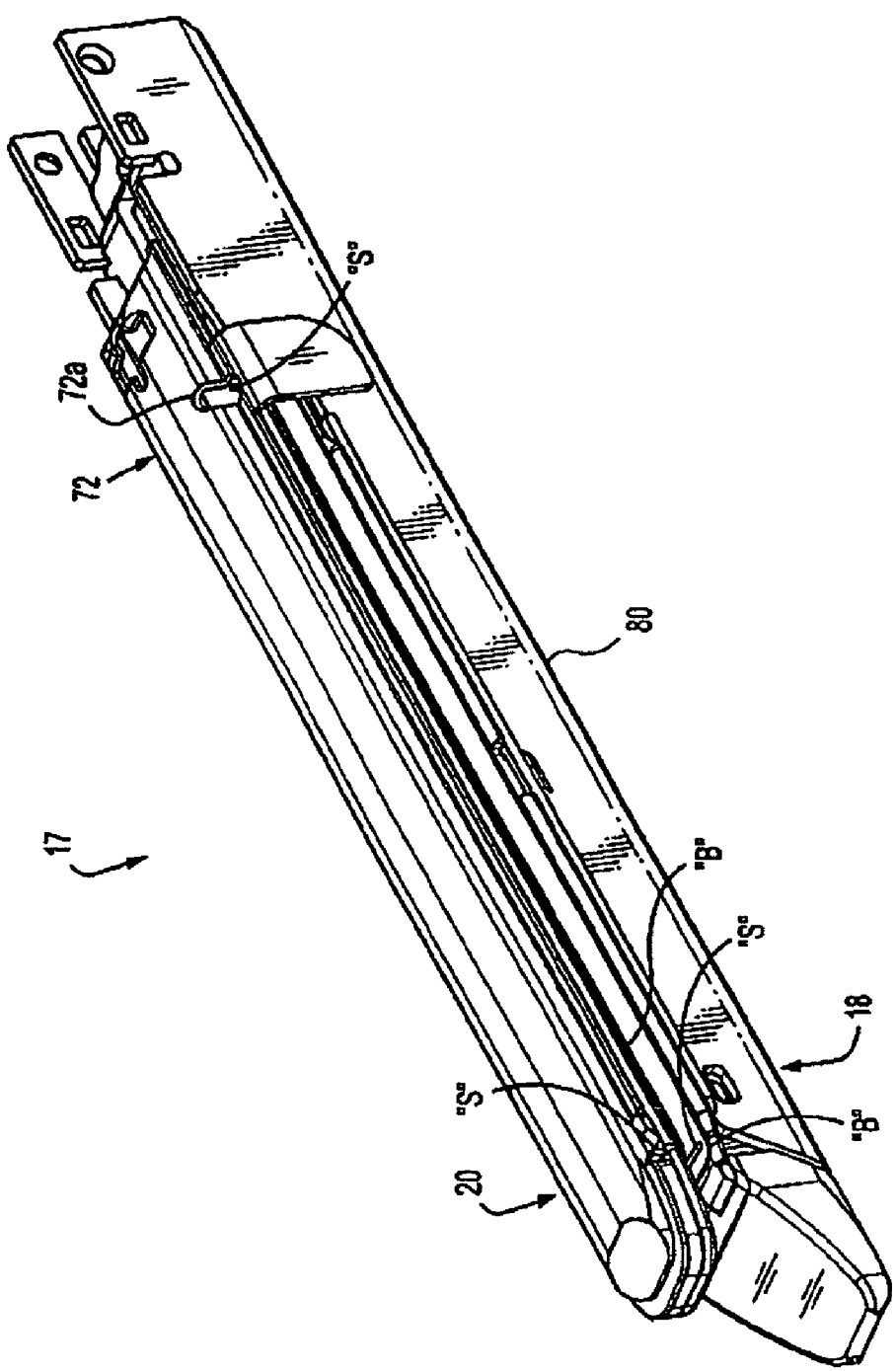
FIG. 21 is perspective view of the distal end of the DLU of FIG. 20.
Figure 26:
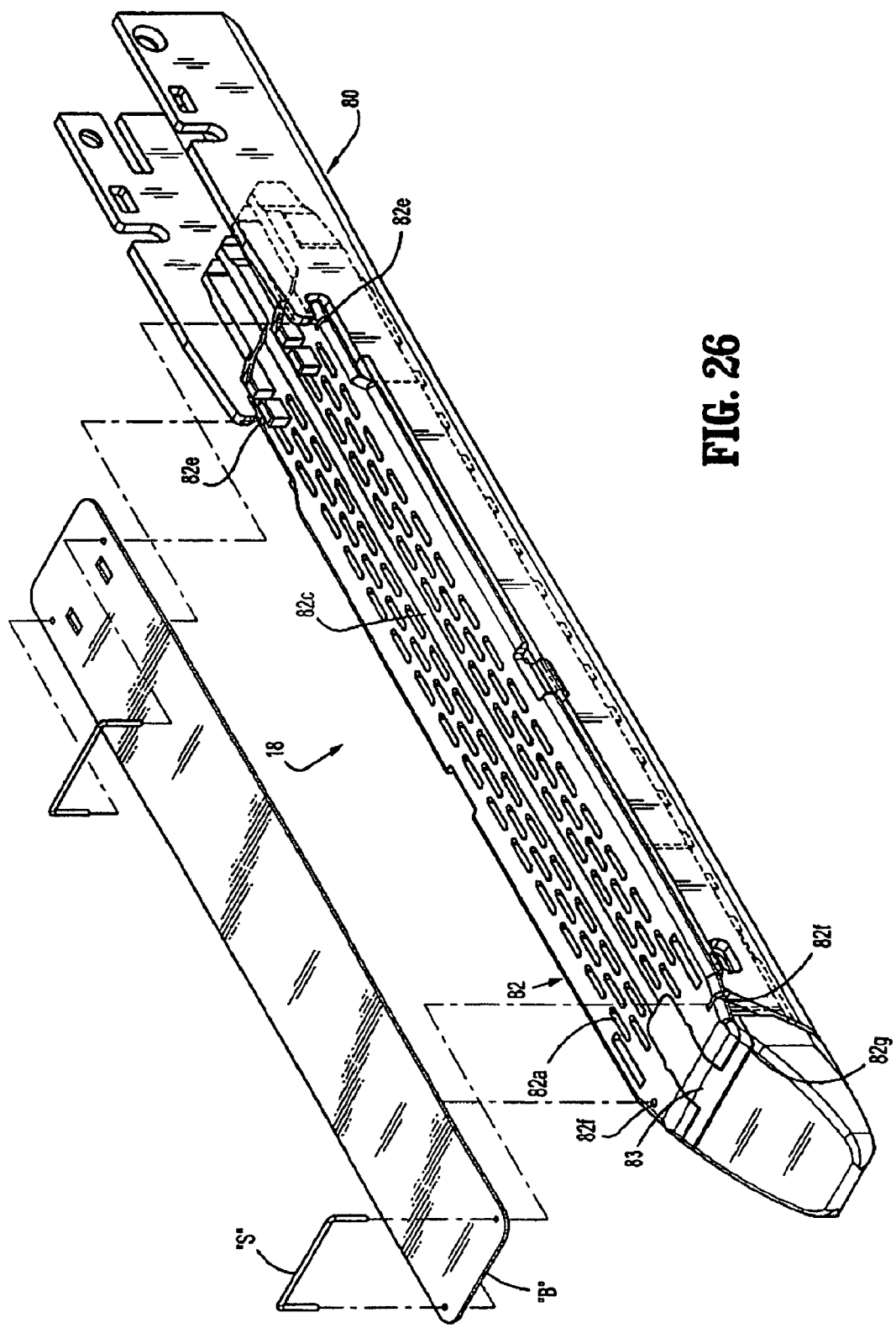
FIG. 26 is a top, perspective view of a cartridge half-section of the DLU of FIGS. 20 and 21.
Figure 27:
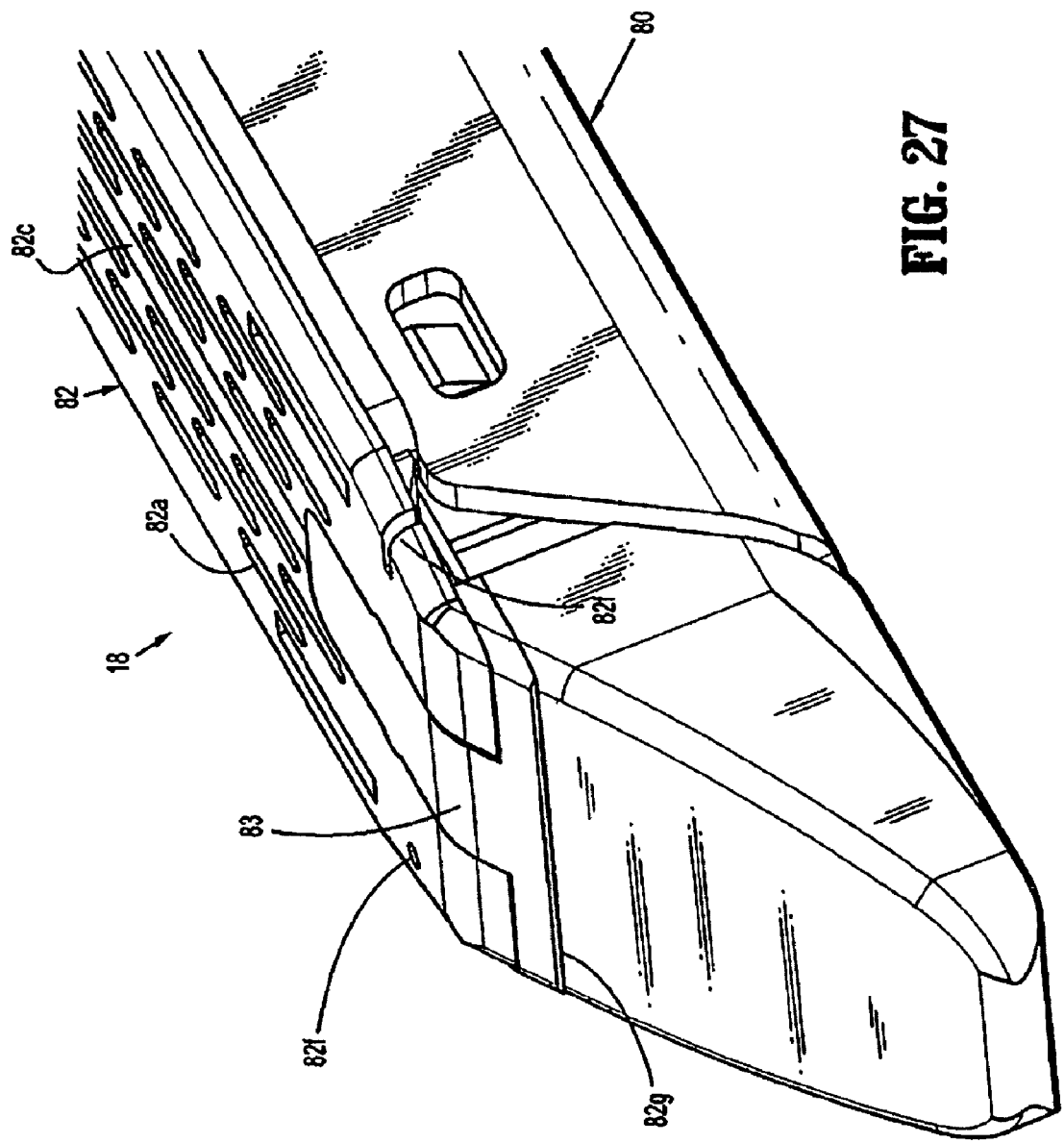
FIG. 27 is a top, perspective view of a distal end of the cartridge half-section of FIG. 26.
Figure 28:
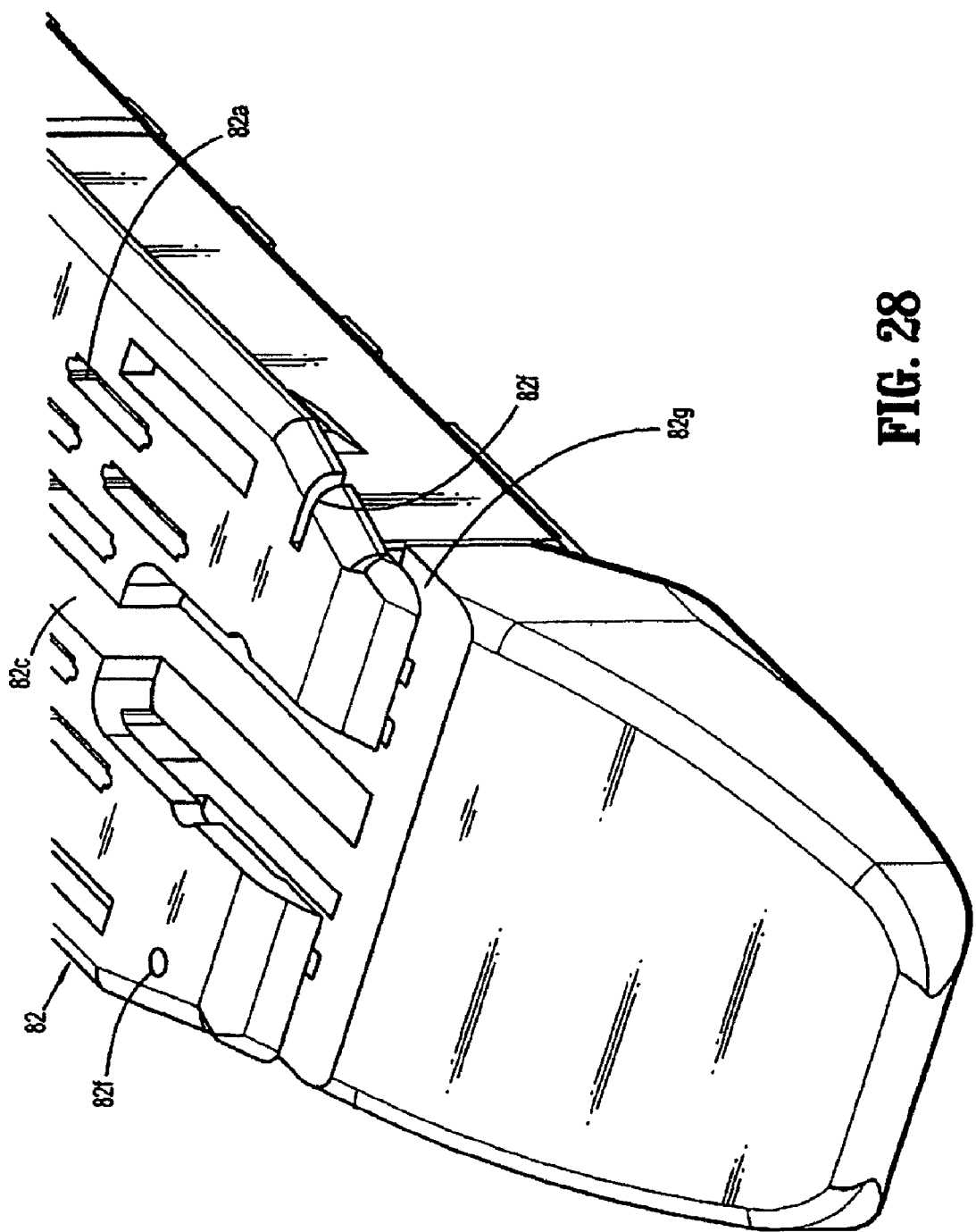
FIG. 28 is a top, perspective view of the distal end of the cartridge half-section of FIG. 27, having a blade stop insert removed therefrom.
Figure 29:
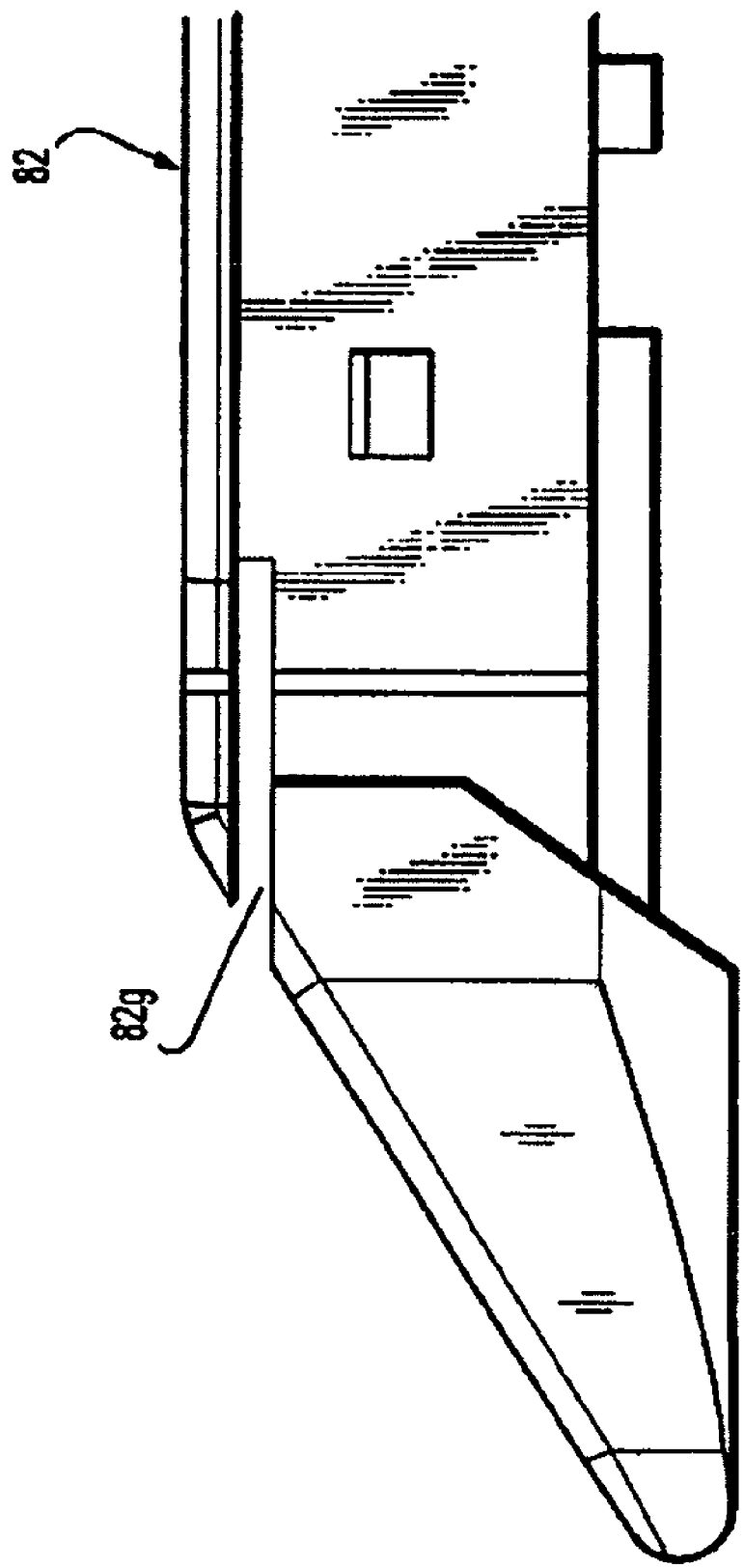
FIG. 29 is a side elevational view of the distal end of the cartridge half-section of FIG. 28.
Figure 30:
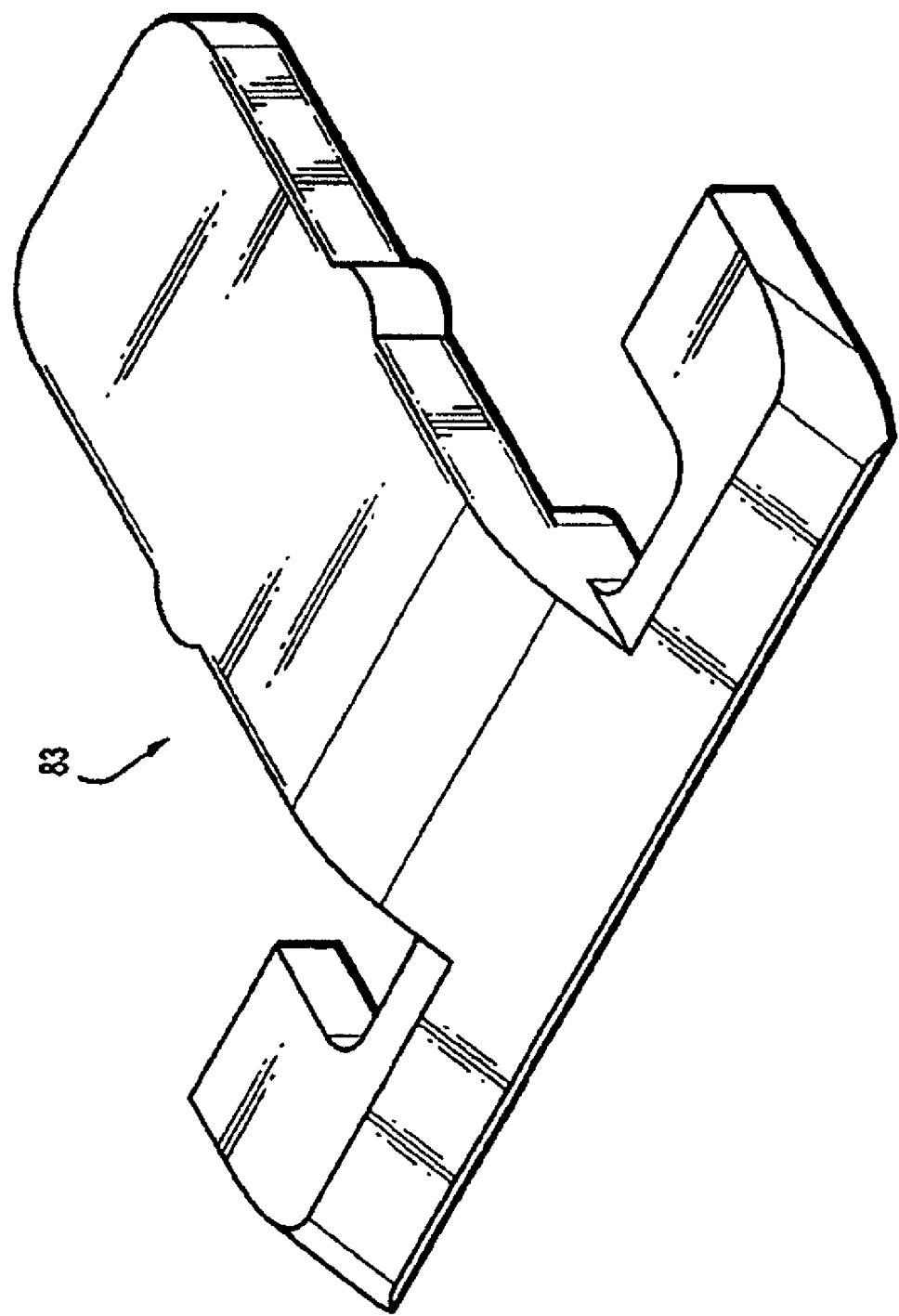
FIG. 30 is a top, perspective view of the blade stop insert of the cartridge half-section of FIGS. 26 and 27.

In an embodiment, as seen in FIGS. 20 and 26, it is contemplated that staple cartridge 82 may include at least one post extending from an upper surface thereof, and the surgical buttress "B" that is to overlie staple cartridge 82 may include a respective complementary aperture formed therein. In this manner, when surgical buttress "B" is placed on staple cartridge 82, the aperture(s) thereof and the post(s) of staple cartridge 82 cooperate with one another to substantially orient and align the surgical buttress "B" over staple cartridge 82.

Staple cartridge 82 defines a distal recess 82g formed therein for selectively receiving a knife blade insert 83 therein. As seen in FIGS. 20, 21 and 26-32, distal recess 82g of staple cartridge 82 defines a plane that is substantially parallel to a tissue contacting surface thereof and includes an extension that is substantially aligned with longitudinal slot 82c.

Figure 31:
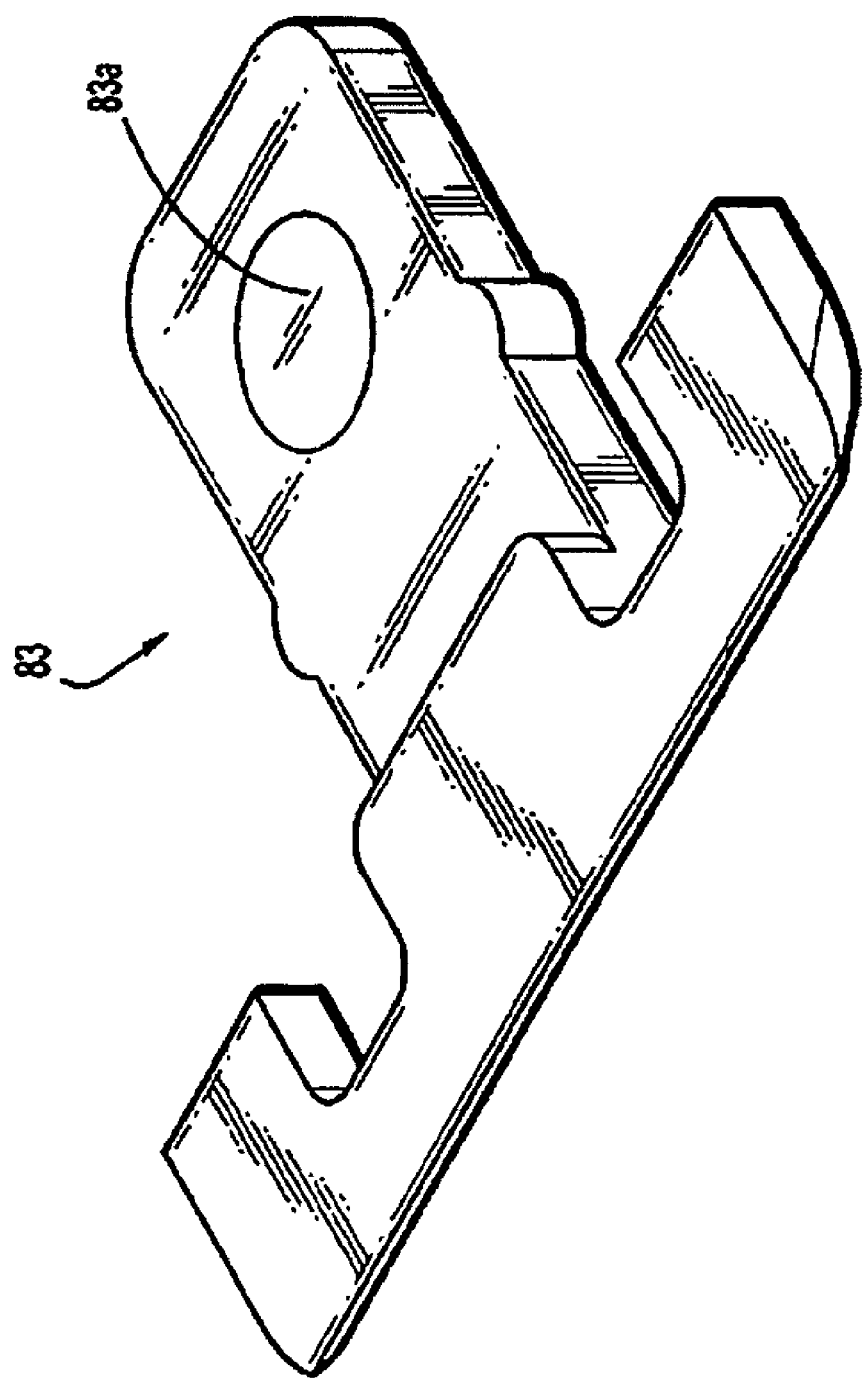
FIG. 31 is a bottom, perspective view of the blade stop insert of the cartridge half-section of FIGS. 26 and 27.

As seen in FIG. 31, knife blade insert 83 includes a projection 83a, in the form of a nub or the like, for snap-fit engaging a complementary receiving structure 74a (see FIG. 20) formed in knife blade 74 of cartridge assembly 18 (see FIG. 2). While a knife blade insert 83 having a projection 83a is shown, it is envisioned that knife blade insert 83 may include a recess or depression formed therein that is configured and adapted for snap-fit engagement with a complementary projection extending from knife blade 74.

Figure 32:
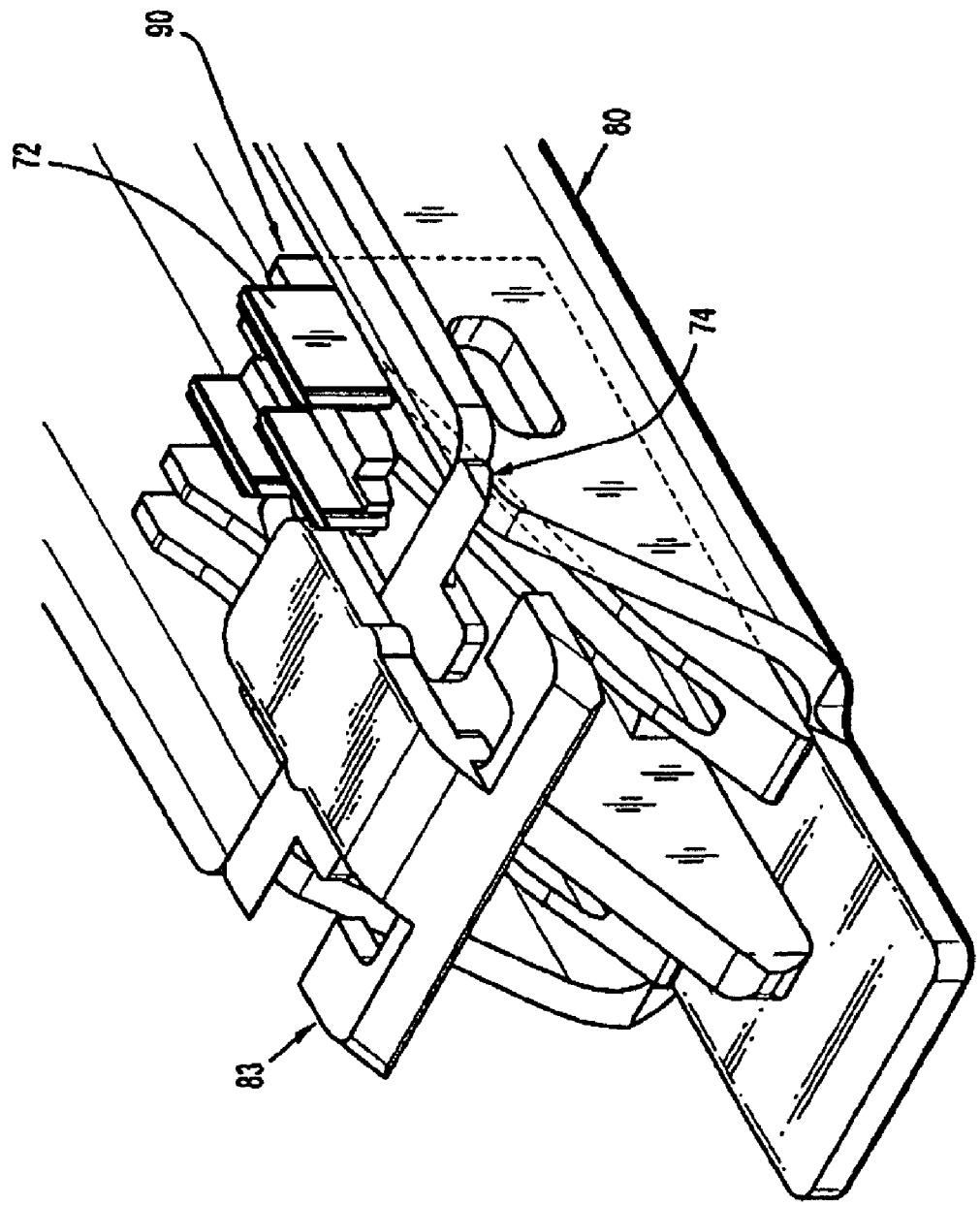
FIG. 32 is a perspective view of the distal end of the cartridge half-section of FIGS. 26 and 27, having a distal nose cap removed therefrom.

As seen in FIG. 32, knife blade insert 83 functions to maintain knife blade 74 in the first condition, i.e., located proximal of the distal pair of recesses 82f of staple cartridge 82, until actuated by drive assembly 50.

Figure 33:
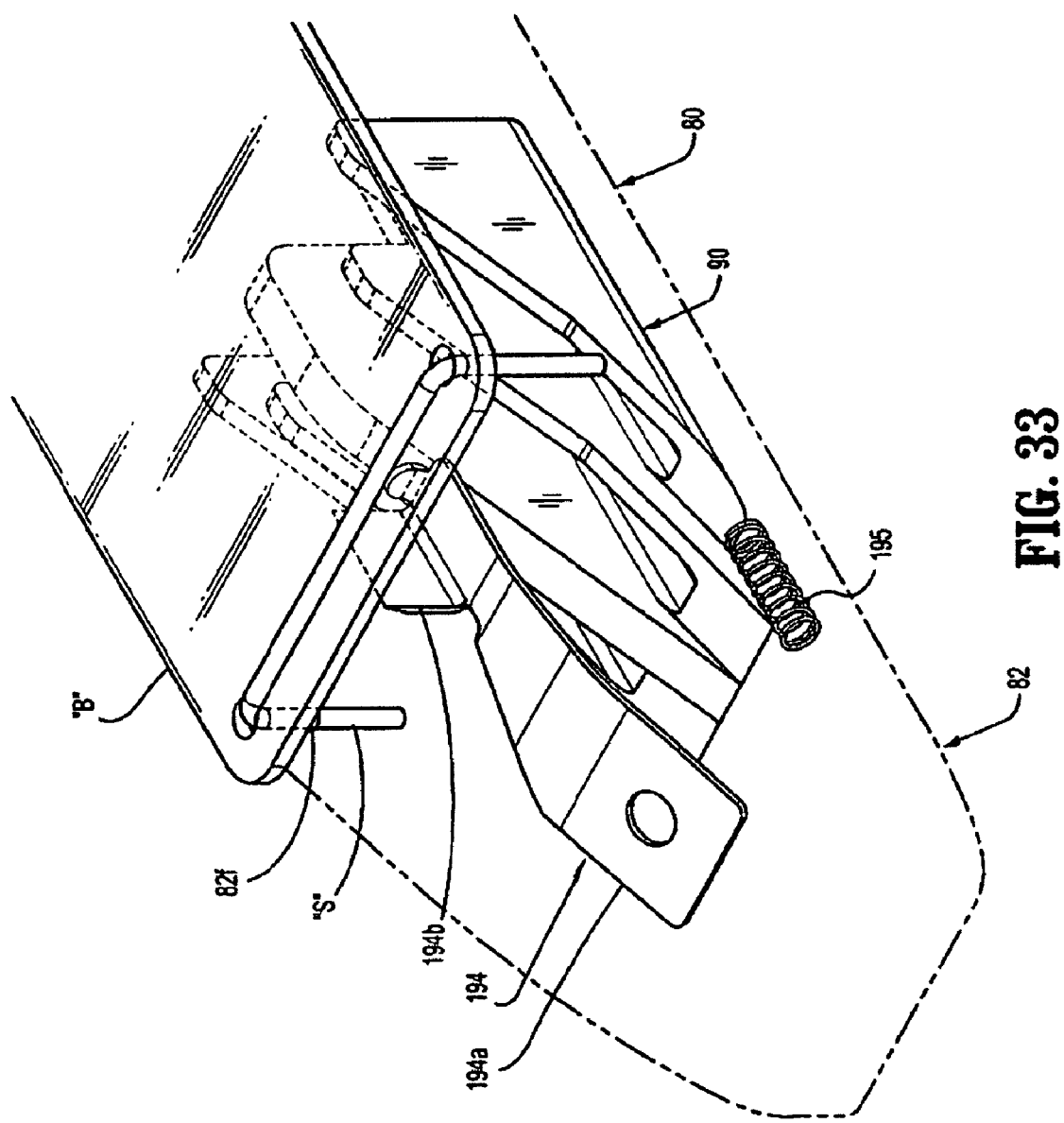
FIG. 33 is a perspective view of a distal end of a cartridge assembly, according to another embodiment of the present disclosure, of a DLU of a surgical stapling apparatus.

Turning now to FIG. 33, a distal end of a cartridge assembly 18, in accordance with another embodiment of the present disclosure, is generally designated as 118. Cartridge assembly 118 is substantially similar to cartridge assembly 18 and will only be discussed in detail herein to the extent necessary to identify differences in construction and operation.

As best seen in FIGS. 22, 24 and 25, at least one recess of each of the proximal pair of recesses 70d and the distal pair of recesses 70e is in the form of a notch having a constricting configuration so as to frictionally cinch, receive and secure a suture, thread or the like therein. As seen in FIG. 33, cartridge assembly 18 includes a knife blade 194 operatively secured in a distal end of carrier 80 or staple cartridge 82. If knife blade 194 is supported in staple cartridge 82, knife blade 194 is replaced when staple cartridge 82 is replaced.

Knife blade 194 includes an arm 194a having a distal end secured near a distal end of carrier 80 or staple cartridge 82, and a proximal end extending substantially toward handle assembly 12 of surgical stapling apparatus 10. Knife blade 194 includes a knife edge 194b extending from proximal end of arm 194a in a direction substantially parallel with longitudinal slot 82c of staple cartridge 82. Knife edge 194b of knife blade 194 is substantially aligned between the distal pair of recesses 82f of staple cartridge 82, such that knife edge 194b is in juxtaposed alignment with an anchor "S" extending between the distal pair of recesses 82f of staple cartridge 82. Arm 194a of knife blade 194 has an initial condition wherein knife edge 194b is spaced away from anchor "S" extending between the distal pair of recesses 82f of staple cartridge 82.

In operation, as drive assembly 50 is advanced distally, actuation sled 90 (e.g., central upstanding wedge 90b) engages against the proximal end of arm 194a of knife blade 194 thereby biasing and camming the proximal end of arm 194a of knife blade 194 towards anchor "S" extending between the distal pair of recesses 82f of staple cartridge 82 such that knife edge 194b thereof severs or otherwise cuts through anchor "S" to free surgical buttress "B" from staple cartridge 82.

Knife edge 194b is retracted into staple cartridge 82 as a result of the spring force created by arm 194a in returning to the un-biased or initial condition. Alternatively, as seen in FIG. 33, a biasing member 195, in the form of a compression spring or the like, may be interposed between or operatively associated with carrier 80 and actuation sled 90. In this manner, upon a completion of a firing stroke, actuation sled 90 compresses biasing member 195, and upon a removal of the force required to complete the firing stroke, biasing member 195 extends and thus urges actuation sled 90 in a proximal direction thereby allowing knife edge 194b to retract into staple cartridge 82.

Exemplary surgical buttresses "B" for use with the surgical stapling devices disclosed herein are shown and described in commonly assigned U.S. Pat. Nos. 5,542,594; 5,908,427; 5,964,774; and 6,045,560, and commonly assigned U.S. Application Serial Nos. 2006/0085034, filed on Apr. 20, 2006; and 2006/0135992, filed on Jun. 22, 2006, the entire contents of each of which is incorporated herein by reference.

As seen throughout the figures, and in particular FIGS. 2, 9-11, 13, 14, 20 and 26, each surgical buttress "B" may be provided with a pair of proximal and/or a pair of distal, spaced apart holes formed therein, wherein the proximal and/or distal holes of the surgical buttress "B" align with and/or are in juxtaposed relation to respective proximal and/or distal recesses of the anvil plate and/or staple cartridge. The holes of the surgical buttress "B" allow for more efficient and easier attachment of surgical buttress "B" to the anvil plate and/or staple cartridge by anchors "S".

Figure 34:
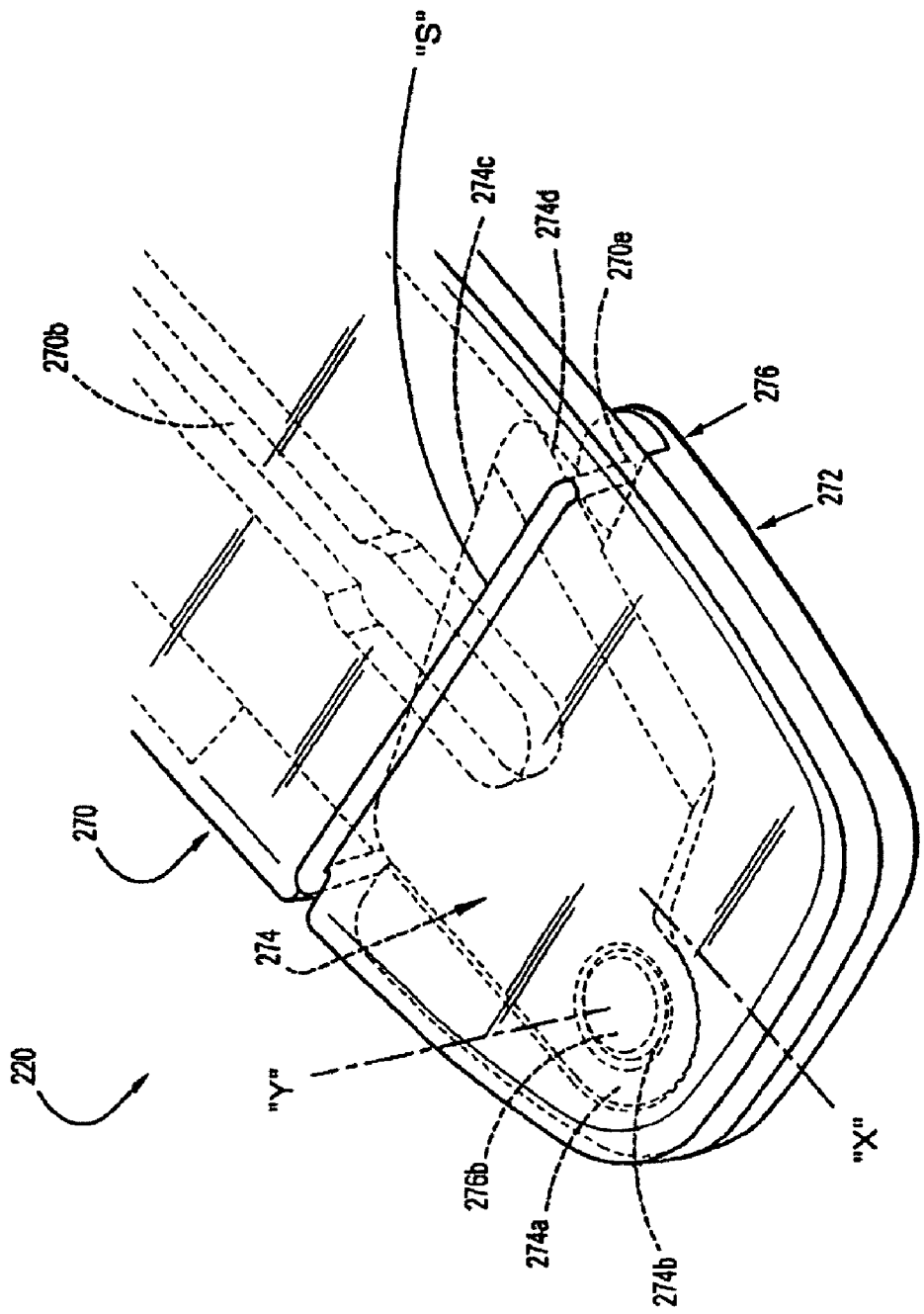
FIG. 34 is a perspective view of a distal end of an anvil assembly, according to another embodiment of the present disclosure, of a DLU of a surgical stapling apparatus.
Figure 35:
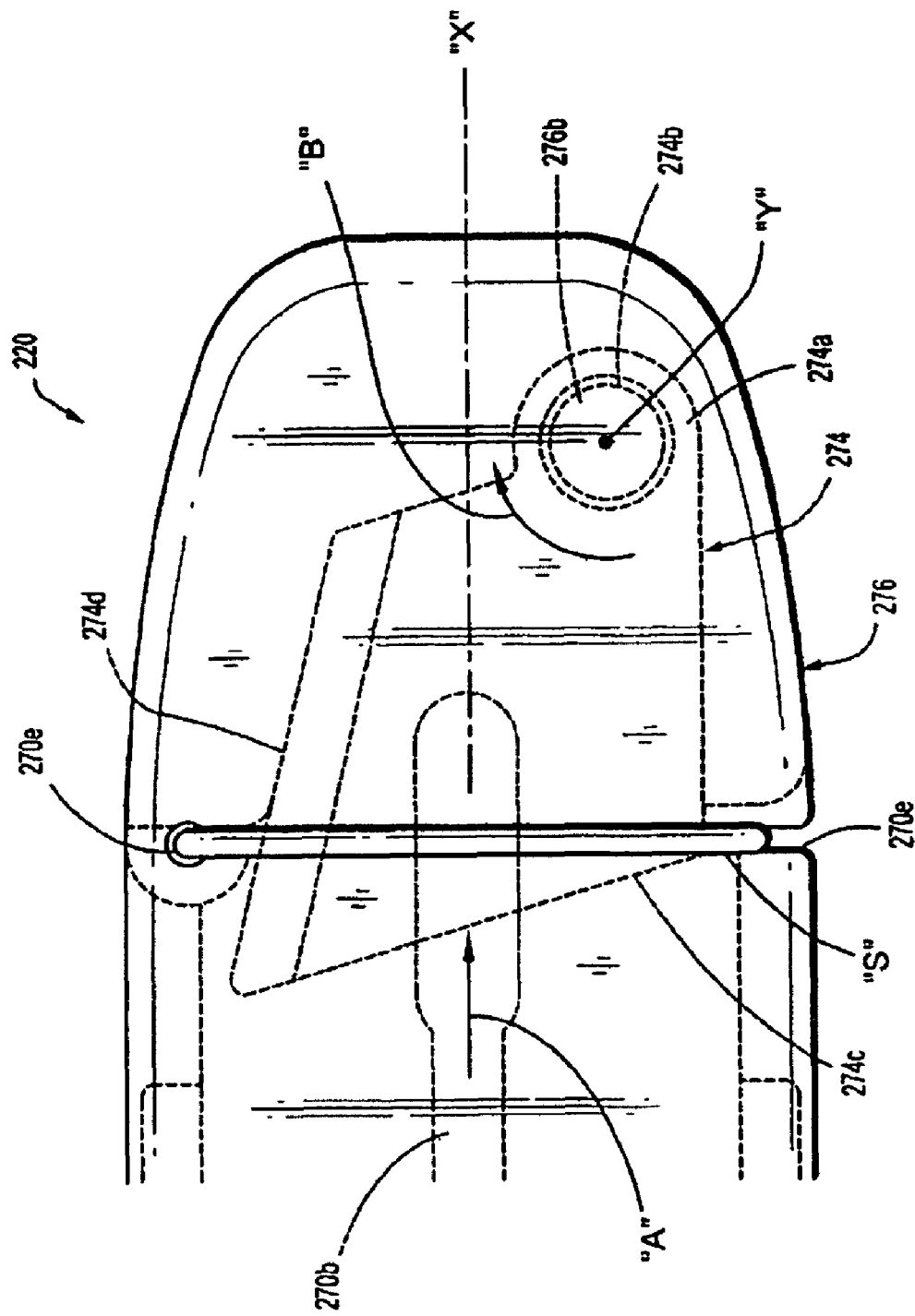
FIG. 35 is a top, plan view of the distal end of the anvil assembly of FIG. 34, illustrating a knife blade thereof in a first position.
Figure 36:
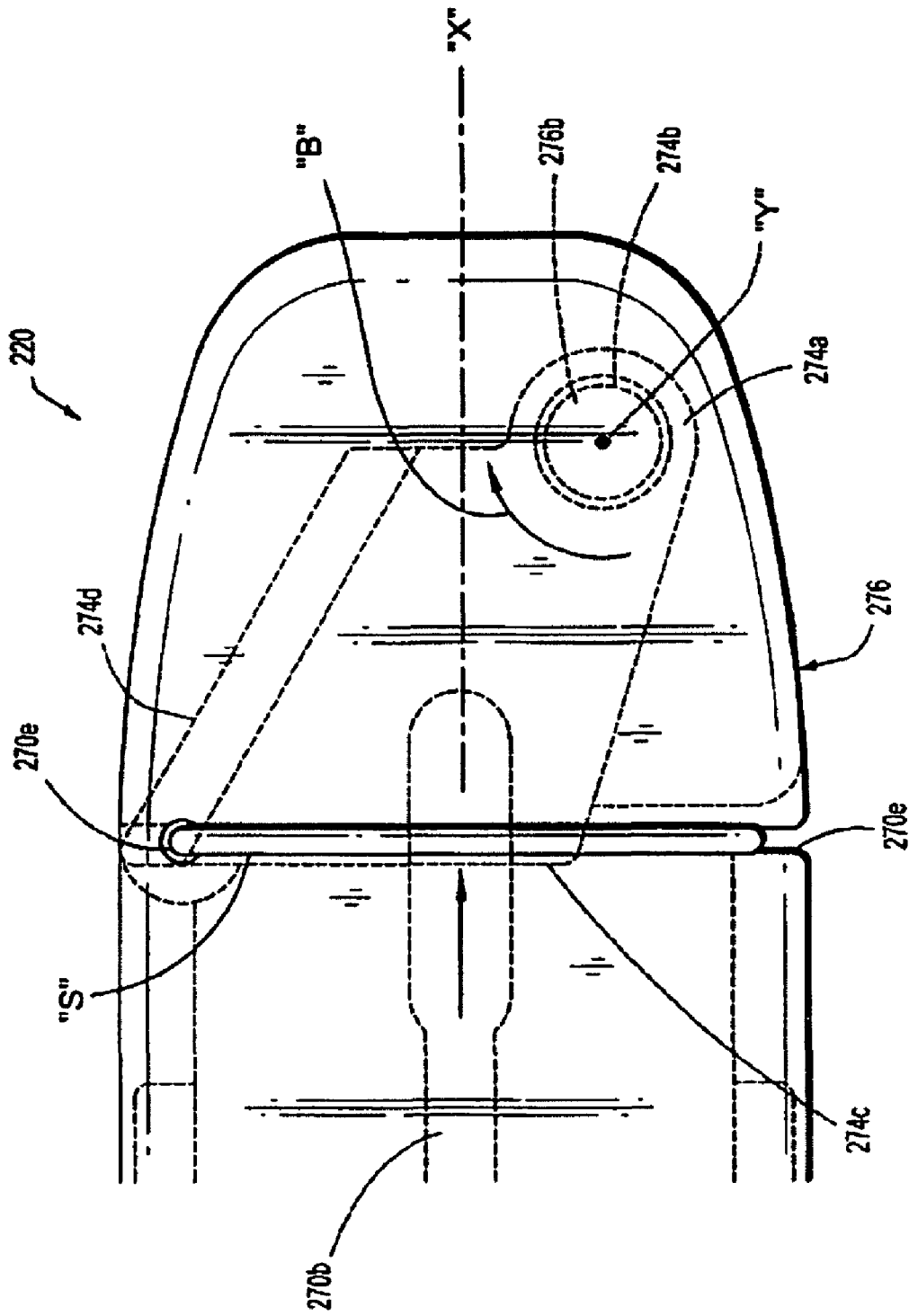
FIG. 36 is a top, plan view of the distal end of the anvil assembly of FIGS. 34 and 35, illustrating the knife blade thereof in a second position.

Turning now to FIGS. 34-36, an anvil assembly according to another embodiment of the present disclosure, for use in a DLU of a surgical stapling apparatus, is generally designated as 220. Anvil assembly 220 is substantially similar to anvil assemblies 20 and thus will only be discussed herein to the extent necessary to identify differences in construction and operation thereof.

As seen in FIGS. 34-36, anvil assembly 220 includes a knife blade 274 pivotally secured thereto, in particular, near a distal end thereof. Knife blade 274 is positioned so as to rotate about a pivot point to sever anchor "S" as drive assembly 50 (see FIG. 2) is advanced to a distal-most position in anvil assembly 220.

In particular, with continued reference to FIGS. 34-36, anvil assembly 220 includes a pivot point 276b formed in distal cap 276, in cover plate 272 and/or in anvil plate 270 for pivotally engaging or supporting knife blade 274. Knife blade 274 includes a lobe 274a defining a pivot window 274b configured and dimensioned to pivotally engage pivot point 276b. Pivot point 276b and pivot window 274b define a pivot axis "Y" that is spaced a distance from a longitudinal axis "X" of longitudinal slot 270b of anvil plate 270.

Knife blade 274 defines a camming edge 274c extending across longitudinal slot 270b of anvil plate 270, and a knife edge 274d extending transverse to camming edge 274c. Knife blade 274 is configured and dimensioned such that a portion of camming edge 274c and/or a portion of knife edge 274d extend across anchor "S".

As seen in FIGS. 34 and 35, knife blade 274 has a first position in which knife edge 274d does not extend across recesses 270e and is out of engagement with anchor "S". In particular, when in the first position, knife edge 274d of knife blade 274 includes a portion extending proximally of recesses 270e and a portion extending distally of recesses 270e. Additionally, when in the first position, knife edge 274d of knife blade 274 is disposed between recesses 270e. Also, when in the first position, camming edge 274c of knife blade 274 includes at least a portion extending proximally of recesses 270e.

As seen in FIG. 36, knife blade 274 has a second position in which knife edge 274d extends across a recess 270e and is in engagement with anchor "S". In particular, when in the second position, knife edge 274d of knife blade 274 includes a portion extending or disposed beyond recess 270e.

In operation, during firing of surgical stapling apparatus 10, as drive assembly 50 (see FIG. 2) is advanced (i.e., moved from a proximal-most position to a distal-most position), drive assembly 50 causes knife blade 274 to slice through anchor "S", thereby freeing the distal end of the anvil buttress (see FIG. 2). In particular, with knife blade 274 in the first position, as seen in FIG. 35, as drive assembly 50 is advanced distally, drive assembly 50 contacts or engages camming edge 274c of knife blade 274, as indicated by arrow "A". As drive assembly 50 is further advanced distally, drive assembly 50 creates a moment around pivot point 276b causing knife blade 274 to rotate thereabout, as indicated by arrow "B". In so doing, as seen in FIG. 36, knife edge 274d of knife blade 274 is advanced or rotated through anchor "S" thus severing anchor "S" and freeing the distal end of the anvil buttress (see FIG. 2).

Figure 37:
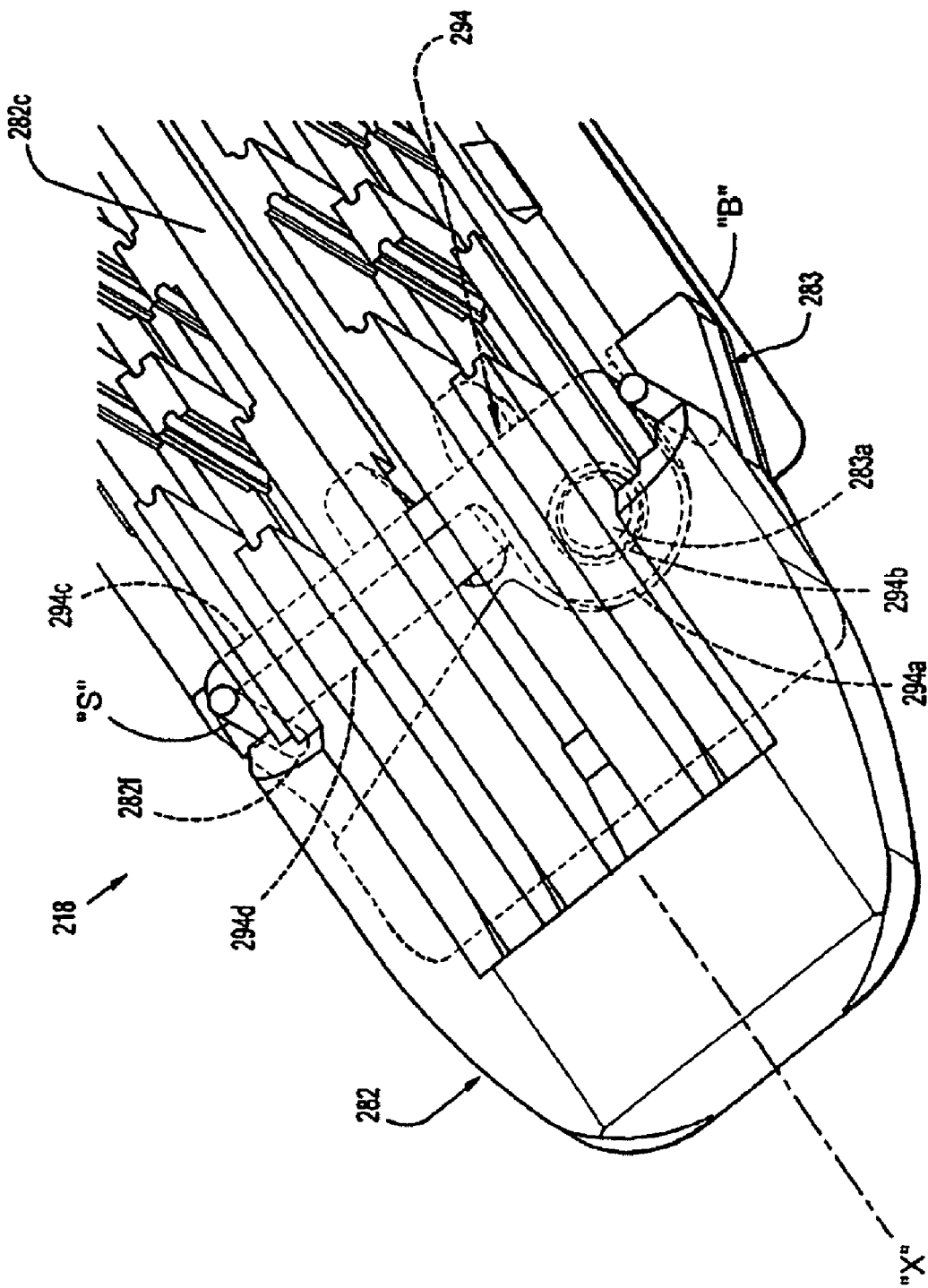
FIG. 37 is a perspective view of a distal end of a cartridge assembly, according to another embodiment of the present disclosure, of a DLU of a surgical stapling apparatus.
Figure 38:
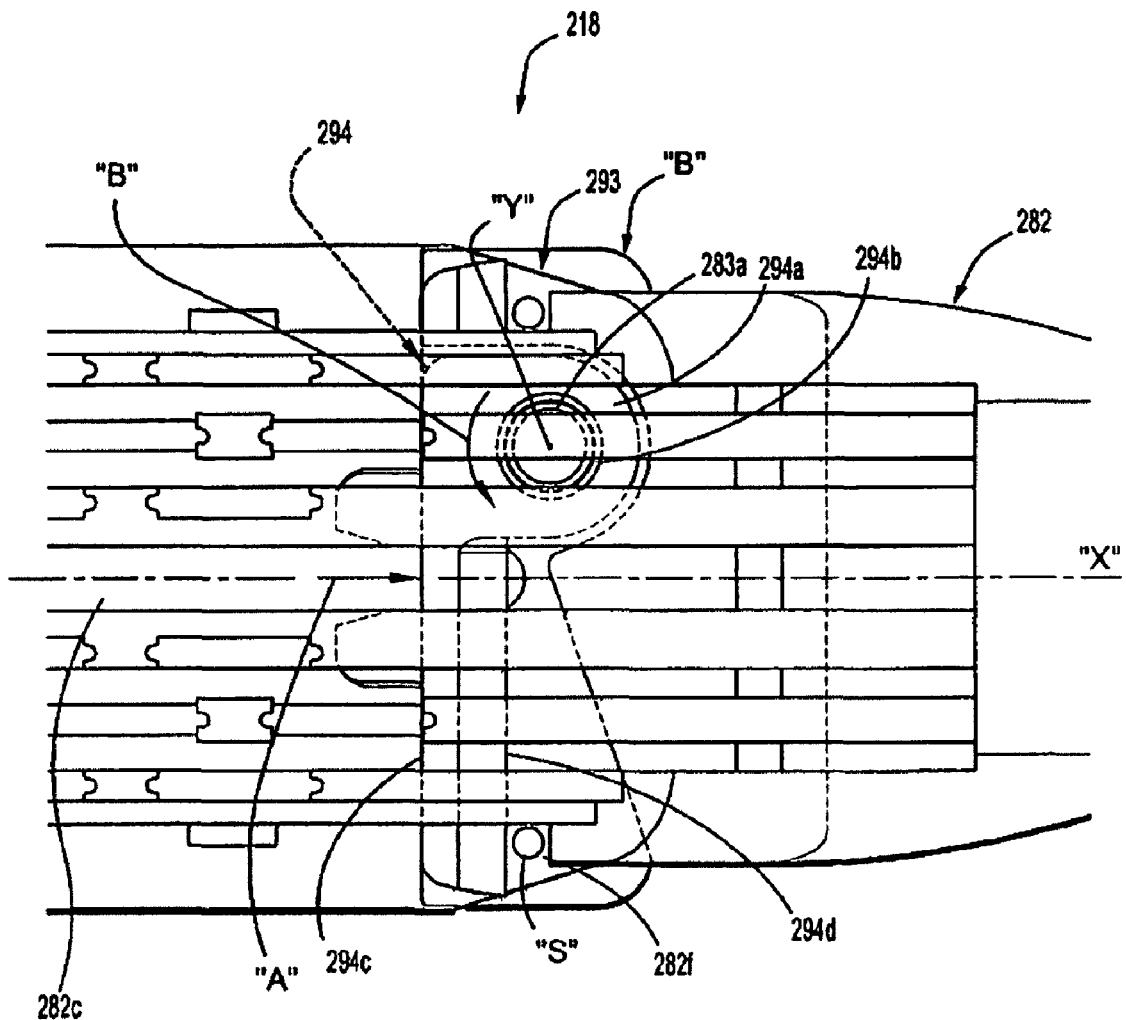
FIG. 38 is a top, plan view of the distal end of the cartridge assembly of FIG. 37, illustrating a knife blade thereof in a first position.
Figure 39:
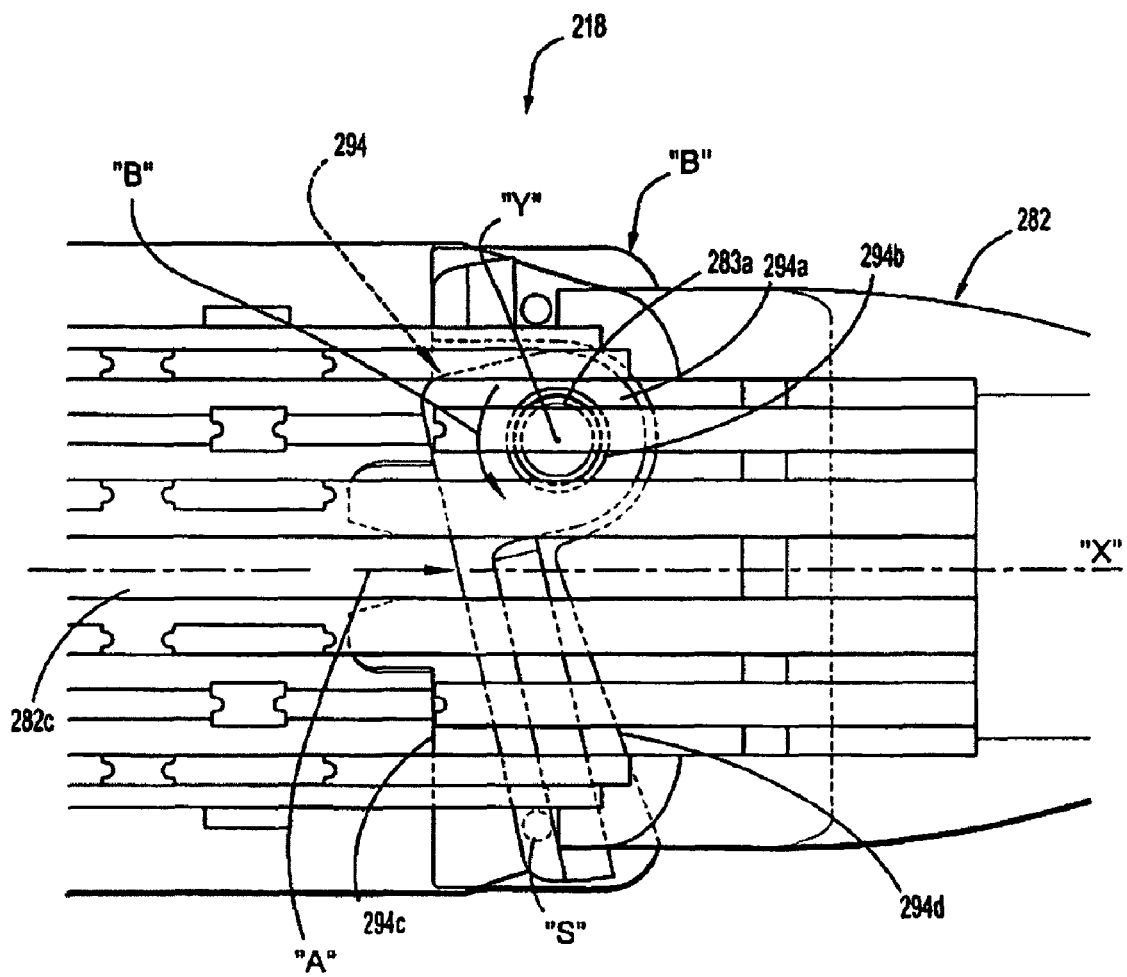
FIG. 39 is a top, plan view of the distal end of the cartridge assembly of FIGS. 37 and 38, illustrating the knife blade thereof in a second position.

Turning now to FIGS. 37-39, a cartridge assembly according to another embodiment of the present disclosure, for use in a DLU of a surgical stapling apparatus, is generally designated as 218. Cartridge assembly 218 is substantially similar to cartridge assemblies 18 and thus will only be discussed herein to the extent necessary to identify differences in construction and operation thereof.

As seen in FIGS. 37-39, cartridge assembly 218 includes a knife blade 294 pivotally secured thereto, in particular, near a distal end thereof. Knife blade 294 is positioned so as to rotate about a pivot point to sever anchor "S" as drive assembly 50 (see FIG. 2) is advanced to a distal-most position in cartridge assembly 218.

In particular, with continued reference to FIGS. 37-39, cartridge assembly 218 includes a pivot point 283a formed in knife blade insert 283 and/or staple cartridge 282 for pivotally engaging or supporting knife blade 294. Knife blade 294 includes a lobe 294a defining a pivot window 294b configured and dimensioned to pivotally engage pivot point 283a. Pivot point 283a and pivot window 294b define a pivot axis "Y" that is spaced a distance from a longitudinal axis "X" of longitudinal slot 282c of staple cartridge 282.

Knife blade 294 defines a back or camming edge 294c extending across longitudinal slot 282c of staple cartridge 282, and a knife edge 294d extending parallel to camming edge 294c. Knife blade 294 is configured and dimensioned such that camming edge 294c and knife edge 294d are located proximal of anchor "S".

As seen in FIGS. 37 and 38, knife blade 294 has a first position in which knife edge 294d does not extend across recesses 282f and is out of engagement with anchor "S". In particular, when in the first position, knife edge 294d of knife blade 294 is located proximal of recess 282f.

As seen in FIG. 39, knife blade 294 has a second position in which knife edge 294d extends across a recess 282f and is in engagement with anchor "S". In particular, when in the second position, knife edge 294d of knife blade 294 includes a portion extending or disposed beyond recess 282f.

In operation, during firing of surgical stapling apparatus 10, as drive assembly 50 (see FIG. 2) is advanced (i.e., moved from a proximal-most position to a distal-most position), drive assembly 50 causes knife blade 294 to slice through anchor "S", thereby freeing the distal end of the cartridge buttress "B". In particular, with knife blade 294 in the first position, as seen in FIG. 38, as drive assembly 50 is advanced distally, drive assembly 50 contacts or engages camming edge 294c of knife blade 294, as indicated by arrow "A". As drive assembly 50 is further advanced distally, drive assembly 50 creates a moment around pivot point 283a causing knife blade 294 to rotate thereabout, as indicated by arrow "B". In so doing, as seen in FIG. 39, knife edge 294d of knife blade 294 is advanced or rotated through anchor "S" thus severing anchor "S" and freeing the distal end of the cartridge buttress "B".

Figure 40:
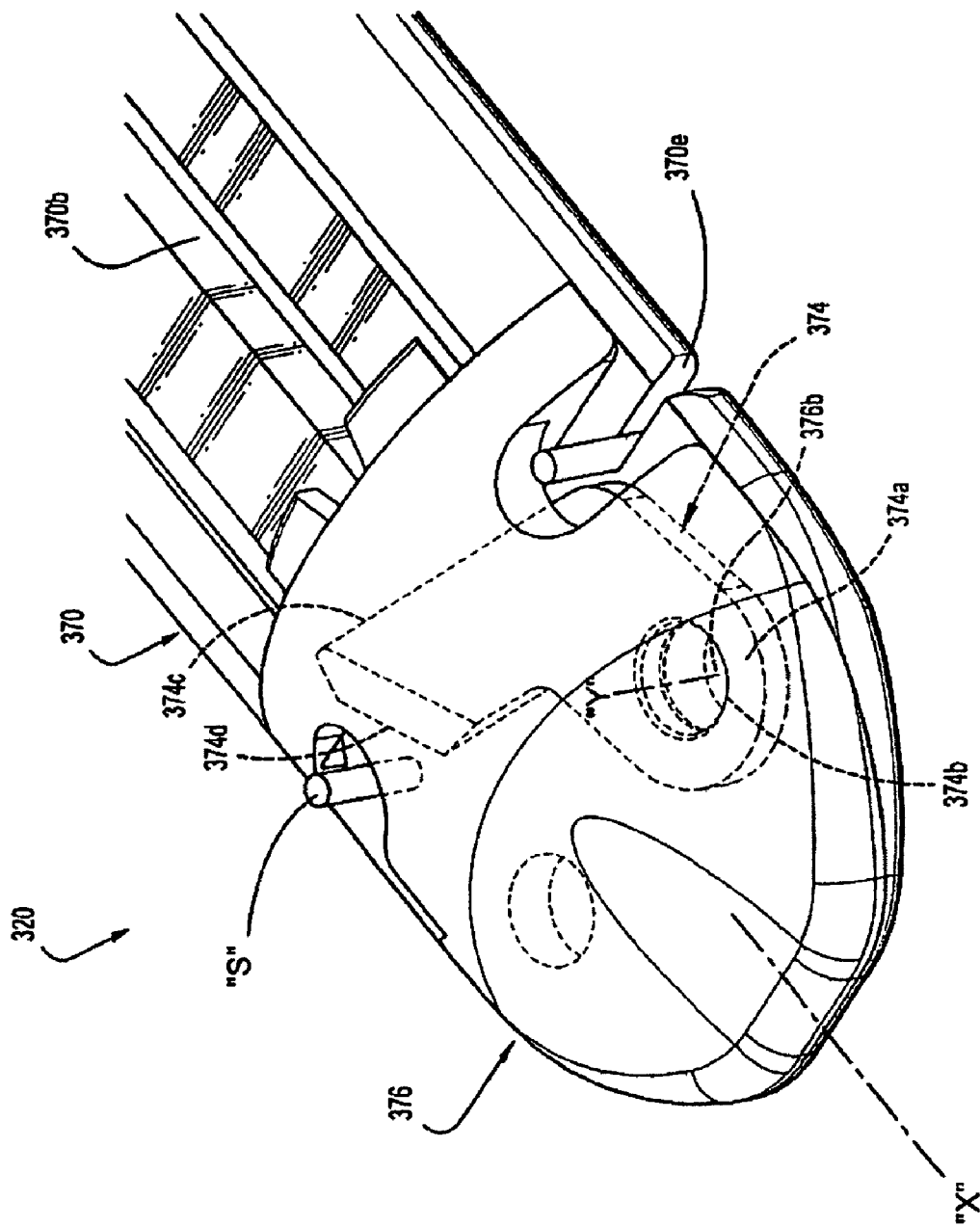
FIG. 40 is a perspective view of a distal end of an anvil assembly, according to yet another embodiment of the present disclosure, of a DLU of a surgical stapling apparatus.
Figure 41:
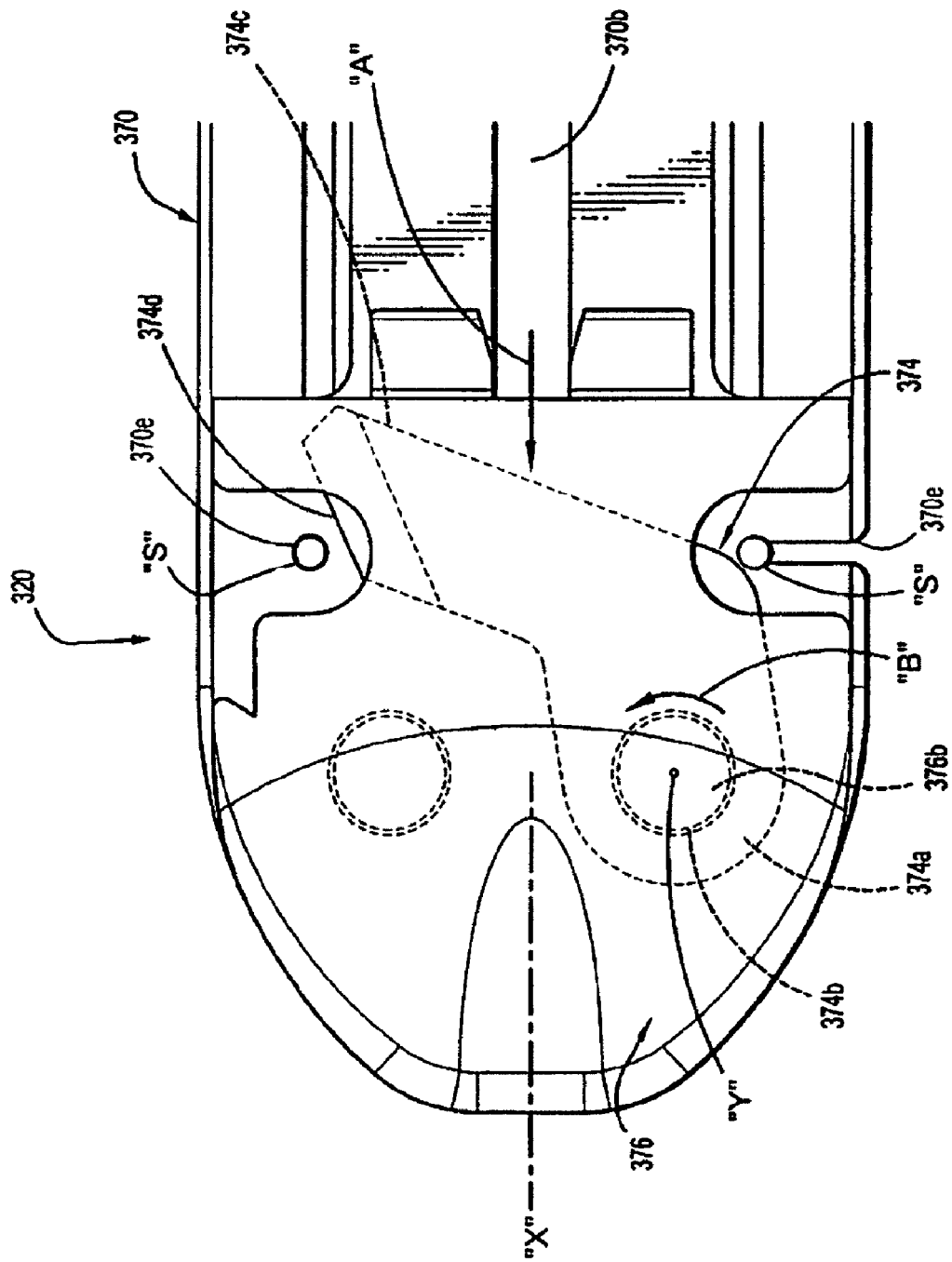
FIG. 41 is a top, plan view of the distal end of the anvil assembly of FIG. 40, illustrating a knife blade thereof in a first position.
Figure 42:
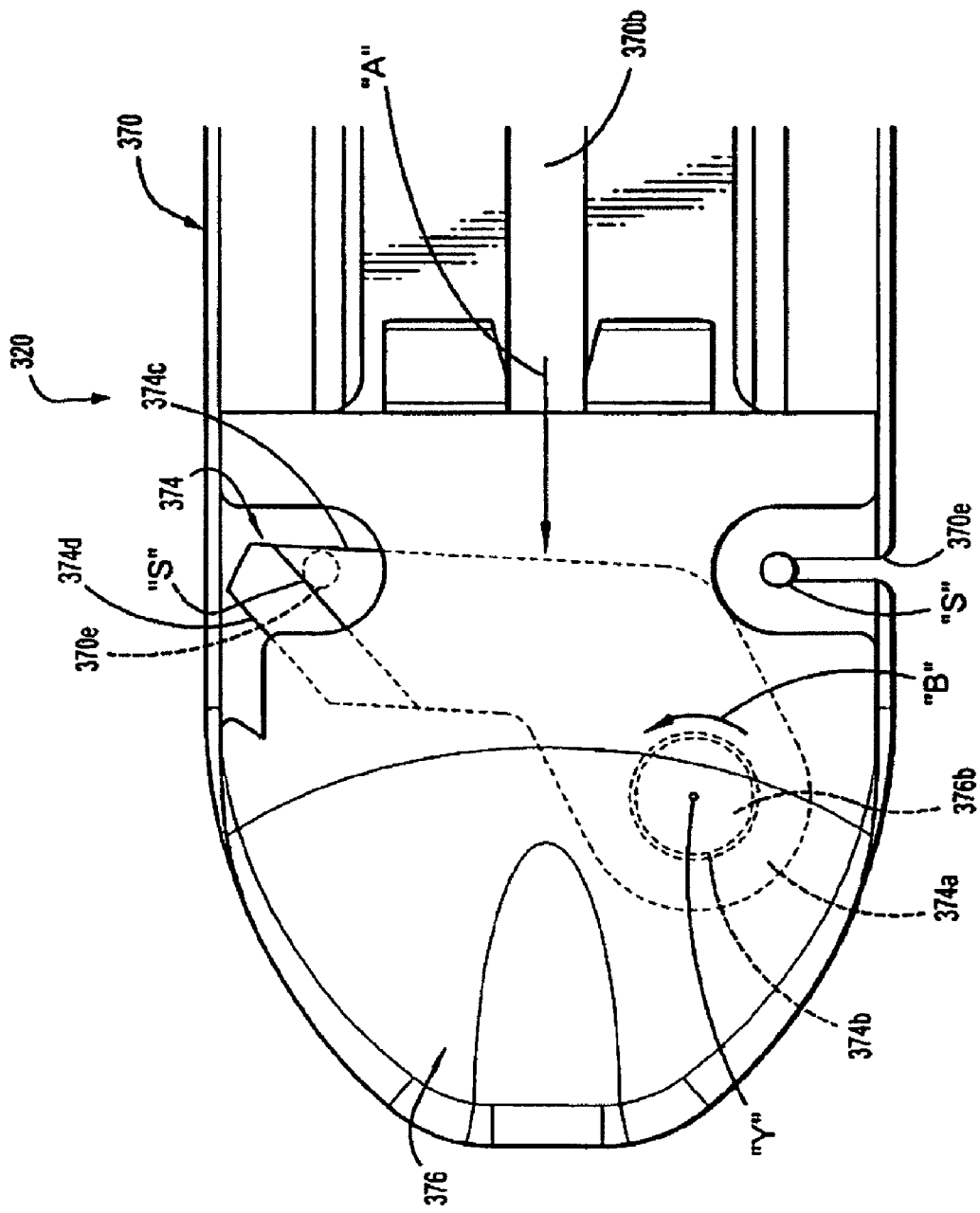
FIG. 42 is a top, plan view of the distal end of the anvil assembly of FIGS. 40 and 41, illustrating the knife blade thereof in a second position.

Turning now to FIGS. 40-42, an anvil assembly according to yet another embodiment of the present disclosure, for use in a DLU of a surgical stapling apparatus, is generally designated as 320. Anvil assembly 320 is substantially similar to anvil assembly 220 and thus will only be discussed herein to the extent necessary to identify differences in construction and operation thereof.

As seen in FIGS. 40-42, anvil assembly 320 includes a knife blade 374 pivotally secured thereto, in particular, near a distal end thereof. Knife blade 374 is positioned so as to rotate about a pivot point to sever anchor "S" as drive assembly 50 (see FIG. 2) is advanced to a distal-most position in anvil assembly 320.

In particular, with continued reference to FIGS. 40-42, anvil assembly 320 includes a pivot point 376b formed in distal cap 376, in cover plate (not shown) and/or in anvil plate 370 for pivotally engaging or supporting knife blade 374. Knife blade 374 includes a lobe 374a defining a pivot window 374b configured and dimensioned to pivotally engage pivot point 376b. Pivot point 376b and pivot window 374b define a pivot axis "Y" that is spaced a distance from a longitudinal axis "X" of longitudinal slot 370b of anvil plate 370.

Knife blade 374 defines a camming edge 374c extending across longitudinal slot 370b of anvil plate 370, and a knife edge 374d extending transverse to camming edge 374c. Knife blade 374 is configured and dimensioned such that camming edge 374c is disposed proximally of anchor "S" and a portion of knife edge 374d extends across anchor "S".

As seen in FIGS. 40 and 41, knife blade 374 has a first position in which knife edge 374d does not extend across recesses 370e and is out of engagement with anchor "S". In particular, when in the first position, knife edge 374d of knife blade 374 includes a portion extending proximally of recesses 370e. Also, when in the first position, camming edge 374c of knife blade 374 is disposed or located proximally of recesses 370e.

As seen in FIG. 42, knife blade 374 has a second position in which knife edge 374d extends across a recess 370e and is in engagement with anchor "S". In particular, when in the second position, knife edge 374d of knife blade 374 includes a portion extending or disposed beyond recess 370e.

In operation, during firing of surgical stapling apparatus 10, as drive assembly 50 (see FIG. 2) is advanced (i.e., moved from a proximal-most position to a distal-most position), drive assembly 50 causes knife blade 374 to slice through anchor "S", thereby freeing the distal end of the anvil buttress (see FIG. 2). In particular, with knife blade 374 in the first position, as seen in FIG. 41, as drive assembly 50 is advanced distally, drive assembly 50 contacts or engages camming edge 374c of knife blade 374, as indicated by arrow "A". As drive assembly 50 is further advanced distally, drive assembly 50 creates a moment around pivot point 376b causing knife blade 374 to rotate thereabout, as indicated by arrow "B". In so doing, as seen in FIG. 42, knife edge 374d of knife blade 374 is advanced or rotated through anchor "S" thus severing anchor "S" and freeing the distal end of the anvil buttress (see FIG. 2).

Figure 43:
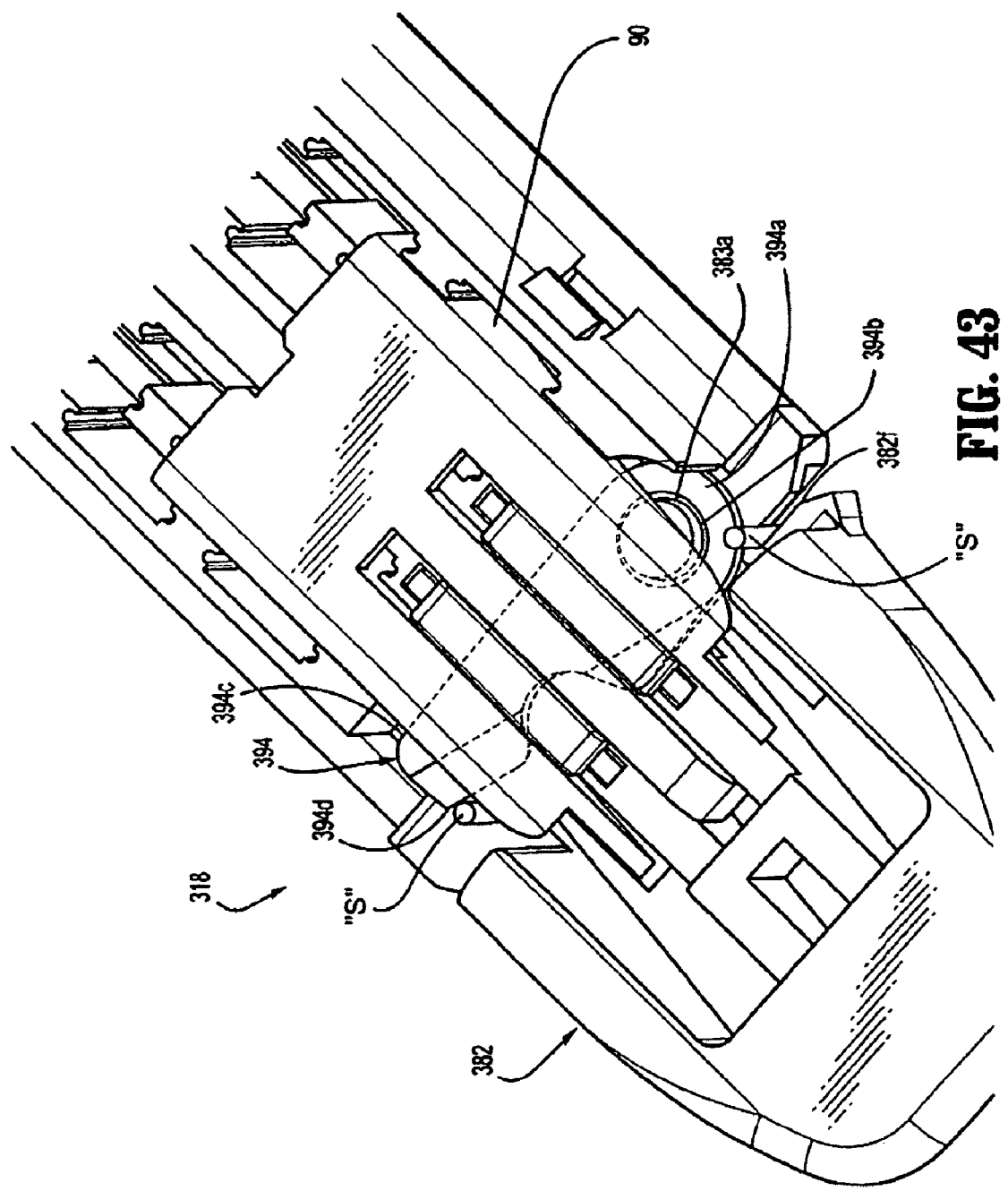
FIG. 43 is a perspective view of a distal end of a cartridge assembly, according to yet another embodiment of the present disclosure, of a DLU of a surgical stapling apparatus.
Figure 44:
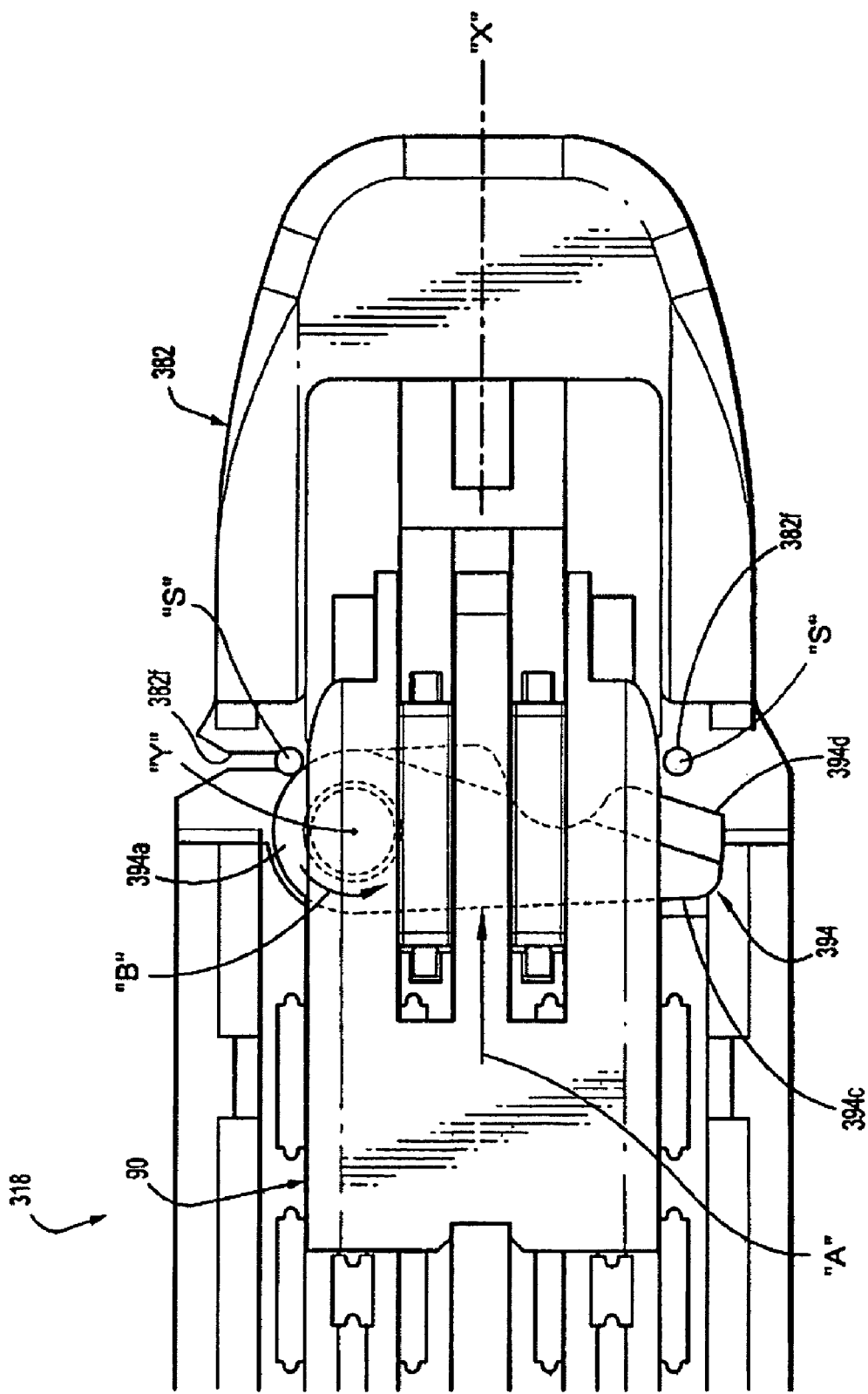
FIG. 44 is a top, plan view of the distal end of the cartridge assembly of FIG. 43, illustrating a knife blade thereof in a first position.
Figure 45:
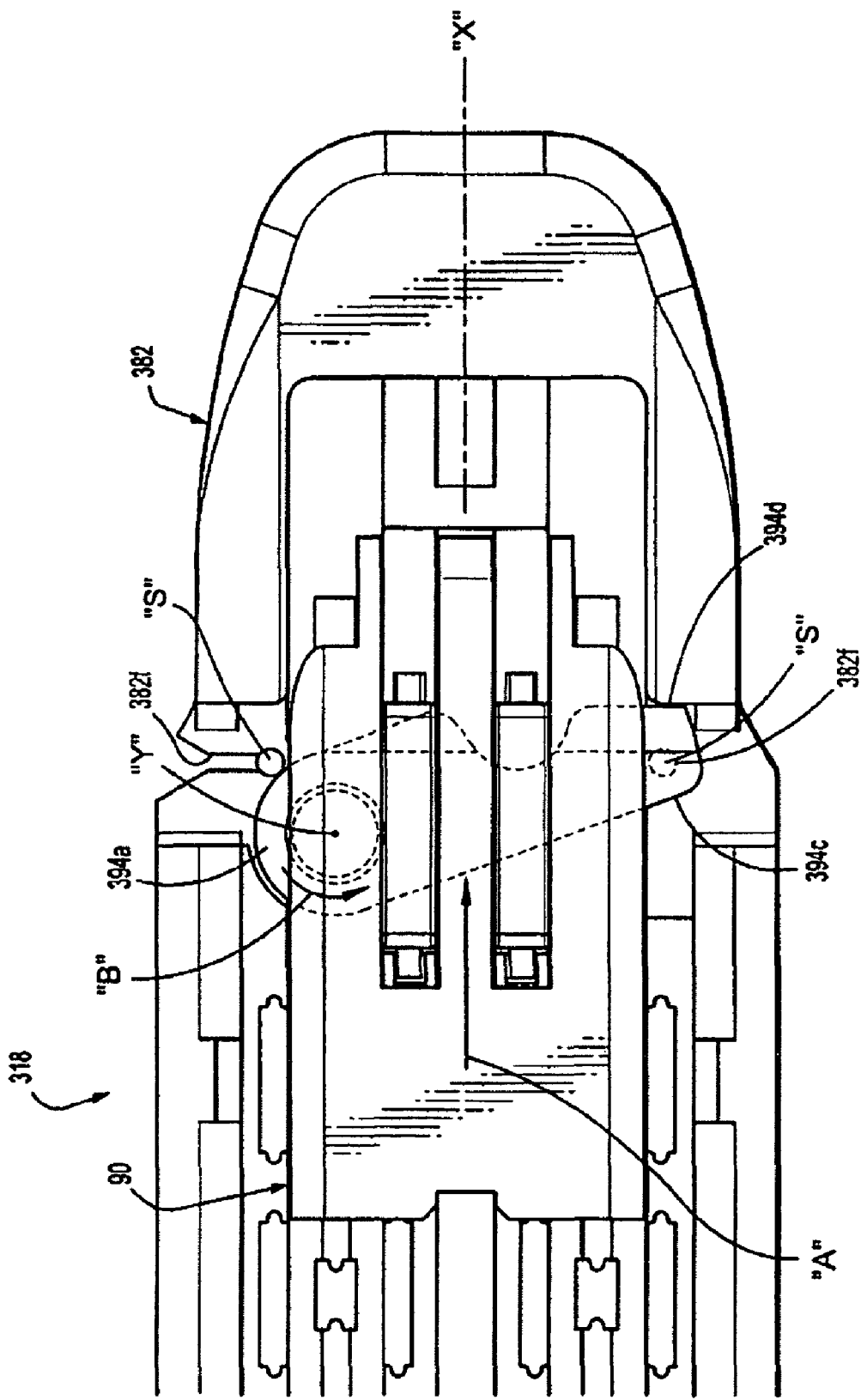
FIG. 45 is a top, plan view of the distal end of the cartridge assembly of FIGS. 43 and 44, illustrating the knife blade thereof in a second position.

Turning now to FIGS. 43-45, a cartridge assembly according to another embodiment of the present disclosure, for use in a DLU of a surgical stapling apparatus, is generally designated as 318. Cartridge assembly 318 is substantially similar to cartridge assembly 218 and thus will only be discussed herein to the extent necessary to identify differences in construction and operation thereof.

As seen in FIGS. 43-45, cartridge assembly 318 includes a knife blade 394 pivotally secured thereto, in particular, near a distal end thereof. Knife blade 394 is positioned so as to rotate about a pivot point to sever anchor "S" as drive assembly 50 (see FIG. 2) is advanced to a distal-most position in cartridge assembly 318.

In particular, with continued reference to FIGS. 43-45, cartridge assembly 318 includes a pivot point 383a formed in knife blade insert 383 and/or staple cartridge 382 for pivotally engaging or supporting knife blade 394. Knife blade 394 includes a lobe 394a defining a pivot window 394b configured and dimensioned to pivotally engage pivot point 383a. Pivot point 383a and pivot window 394b define a pivot axis "Y" that is spaced a distance from a longitudinal axis "X" of longitudinal slot 382c of staple cartridge 382.

Knife blade 394 defines a back or camming edge 394c extending across longitudinal slot 382c of staple cartridge 382, and a knife edge 394d extending parallel to camming edge 394c. Knife blade 394 is configured and dimensioned such that camming edge 394c and knife edge 394d are located proximal of anchor "S".

As seen in FIGS. 43 and 44, knife blade 394 has a first position in which knife edge 394d does not extend across recesses 382f and is out of engagement with anchor "S". In particular, when in the first position, knife edge 394d of knife blade 394 is located proximal of recess 382f.

As seen in FIG. 45, knife blade 394 has a second position in which knife edge 394d extends across a recess 382f and is in engagement with anchor "S". In particular, when in the second position, knife edge 394d of knife blade 394 includes a portion extending or disposed beyond recess 382f.

In operation, during firing of surgical stapling apparatus 10, as drive assembly 50 (see FIG. 2) is advanced (i.e., moved from a proximal-most position to a distal-most position), drive assembly 50 pushes actuation sled 90 into knife blade 394 causing knife blade 394 to slice through anchor "S", thereby freeing the distal end of the cartridge buttress "B". In particular, with knife blade 394 in the first position, as seen in FIG. 44, as drive assembly 50 is advanced distally, drive assembly 50 moved actuation sled 90 into contact or engagement with camming edge 394c of knife blade 394, as indicated by arrow "A". As drive assembly 50 is further advanced distally, actuation sled 90 creates a moment around pivot point 383a causing knife blade 394 to rotate thereabout, as indicated by arrow "B". In so doing, as seen in FIG. 45, knife edge 394d of knife blade 394 is advanced or rotated through anchor "S" thus severing anchor "S" and freeing the distal end of the cartridge buttress "B".

Figure 46:
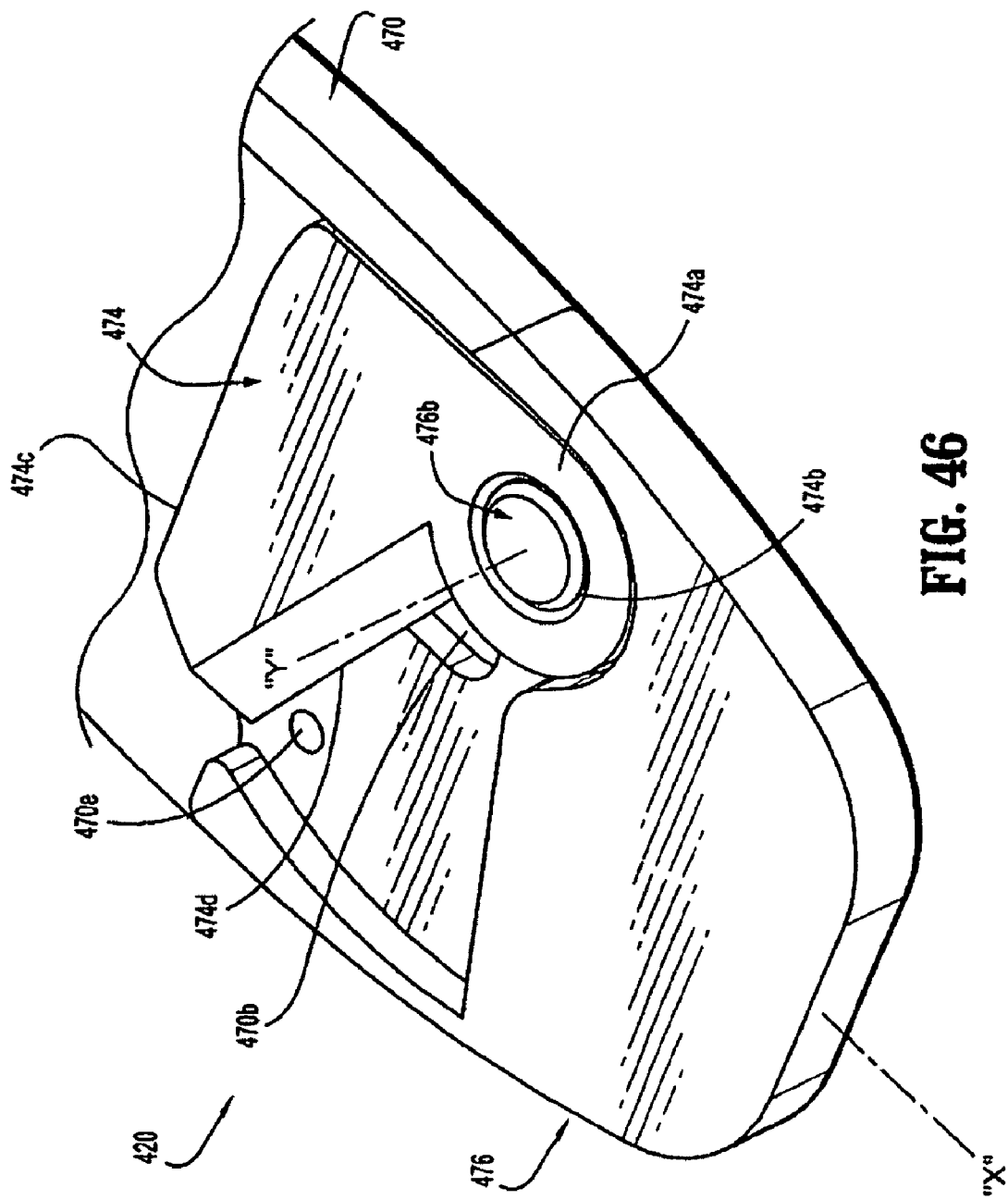
FIG. 46 is a schematic, perspective view of a distal end of an anvil assembly, according to still another embodiment of the present disclosure, of a DLU of a surgical stapling apparatus.

Turning now to FIG. 46, an anvil assembly according to yet another embodiment of the present disclosure, for use in a DLU of a surgical stapling apparatus, is generally designated as 420. Anvil assembly 420 is substantially similar to anvil assemblies 220 and 320 and thus will only be discussed herein to the extent necessary to identify differences in construction and operation thereof.

As seen in FIG. 46, anvil assembly 420 includes a knife blade 474 pivotally secured thereto, in particular, near a distal end thereof. Knife blade 474 is positioned so as to rotate about a pivot point to sever anchor "S" as drive assembly 50 (see FIG. 2) is advanced to a distal-most position in anvil assembly 420.

In particular, with continued reference to FIG. 46, anvil assembly 420 includes a pivot point 476b formed in distal cap 476, in the cover plate (not shown) and/or in anvil plate 470 for pivotally engaging or supporting knife blade 474. Knife blade 474 includes a lobe 474a defining a pivot window 474b configured and dimensioned to pivotally engage pivot point 476b. Pivot point 476b and pivot window 474b define a pivot axis "Y" that is spaced a distance from a longitudinal axis "X" of longitudinal slot 470b of anvil plate 470.

Knife blade 474 defines a camming edge 474c extending across longitudinal slot 470b of anvil plate 470, and a knife edge 474d extending transverse to camming edge 474c. Knife blade 474 is configured and dimensioned such that camming edge 474c is disposed proximally of the anchor (not shown) and a portion of knife edge 474d extends across anchor.

As seen in FIG. 46, knife blade 474 has a first position in which knife edge 474d does not extend across recesses 470e and is out of engagement with anchor. In particular, when in the first position, knife edge 474d of knife blade 474 includes a portion extending proximally of recesses 470e and a portion extending distally of recesses 470e. Also, when in the first position, camming edge 474c of knife blade 474 is disposed or located proximally of recesses 470e.

Turning now to FIGS. 47-75, an end effector, configured for use or connection with a handle of an endoscopic surgical stapling apparatus is generally designated as 1000. End effector 1000 includes a cartridge assembly 1200 housing a plurality of surgical fasteners or staples 1228 (see FIG. 48) and an anvil assembly 1300 movably secured in relation to cartridge assembly 1200. End effector 1000 measures from about 30 mm to about 60 mm in length. End effector 1000 may be configured to apply six (6) linear rows of staples.

Figure 47:
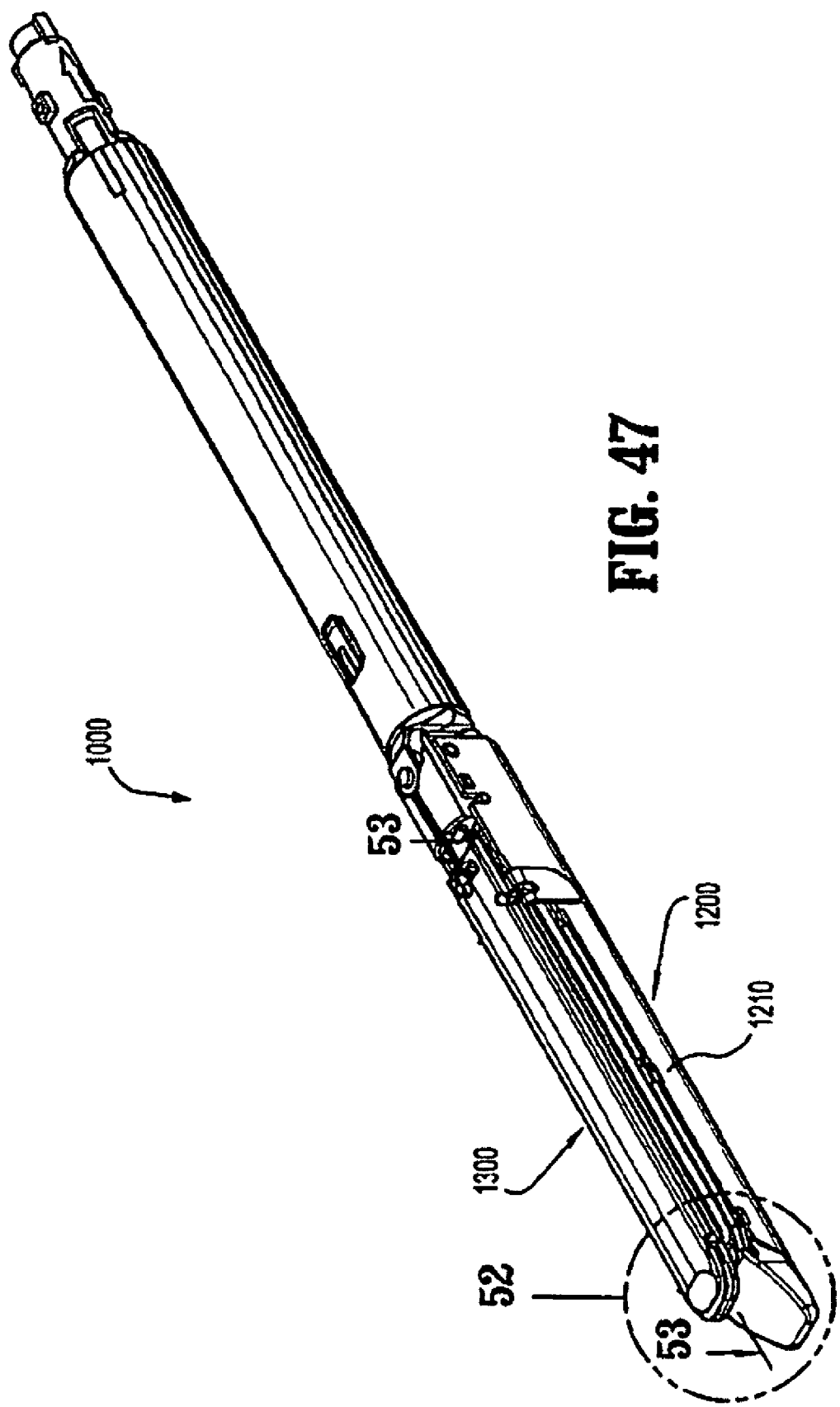
FIG. 47 is an exploded, perspective view of a DLU of the surgical stapling apparatus of FIG. 1, according to another embodiment of the present disclosure.
Figure 48:
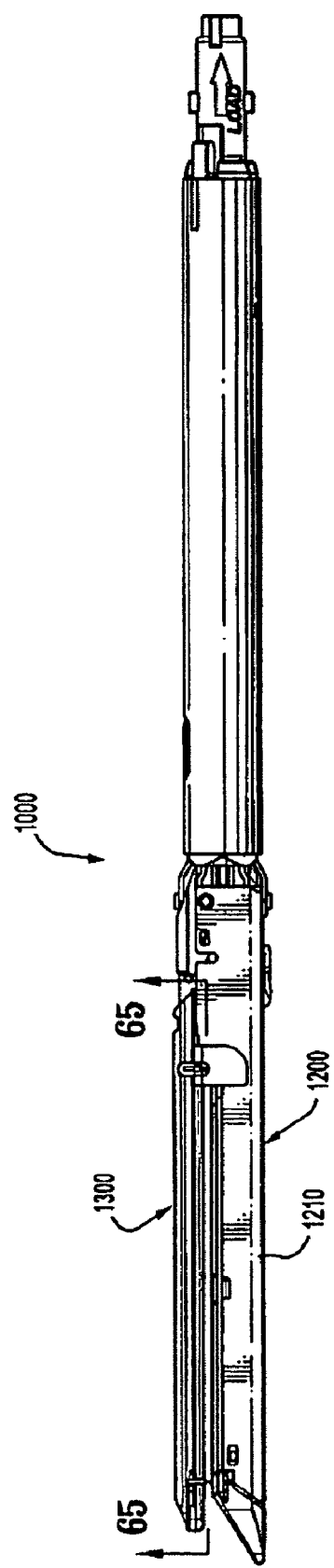
FIG. 48 is a side elevational view of the DLU of FIG. 47.
Figure 49:
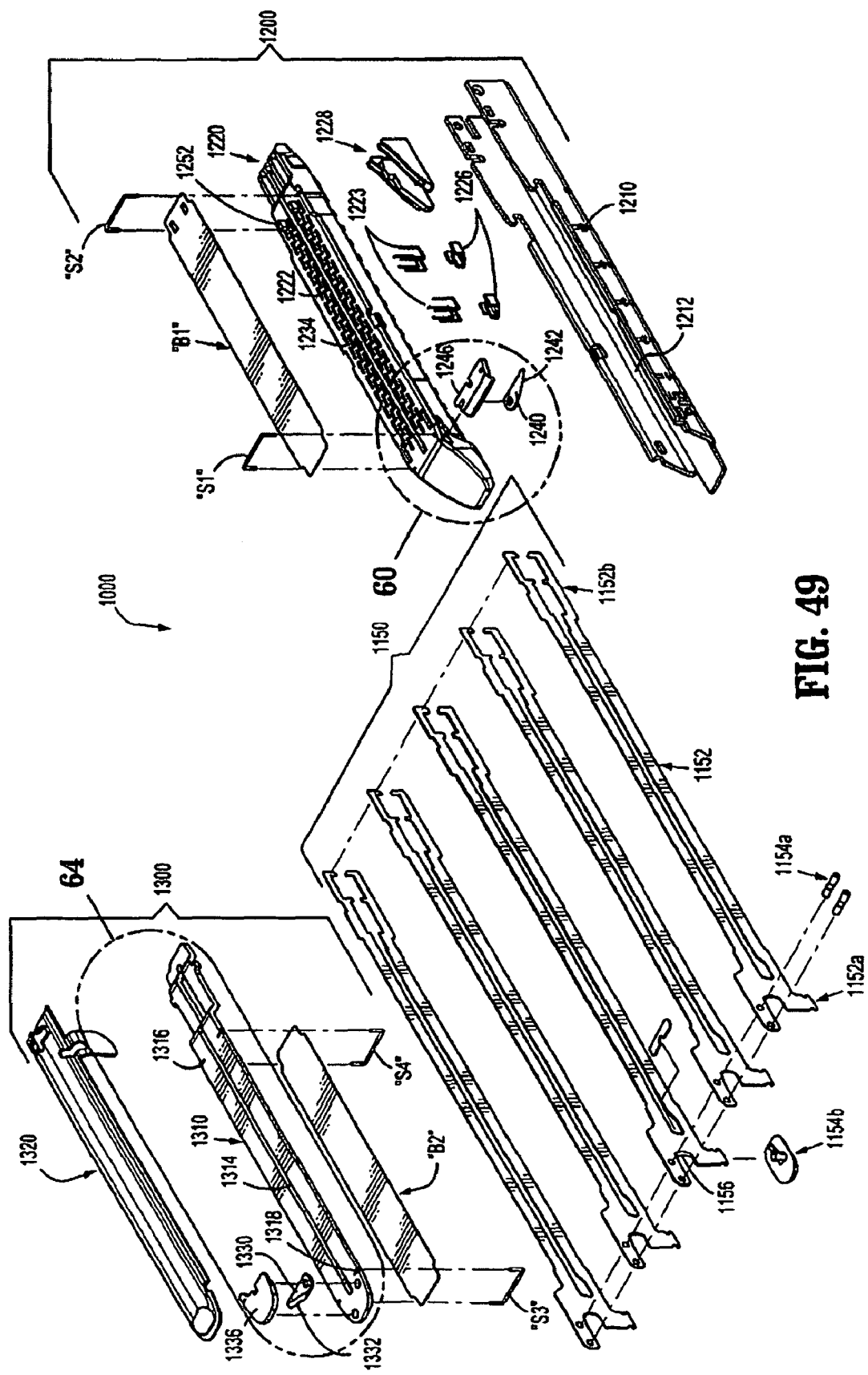
FIG. 49 is an exploded perspective view of the DLU of FIGS. 47 and 48.
Figure 52:
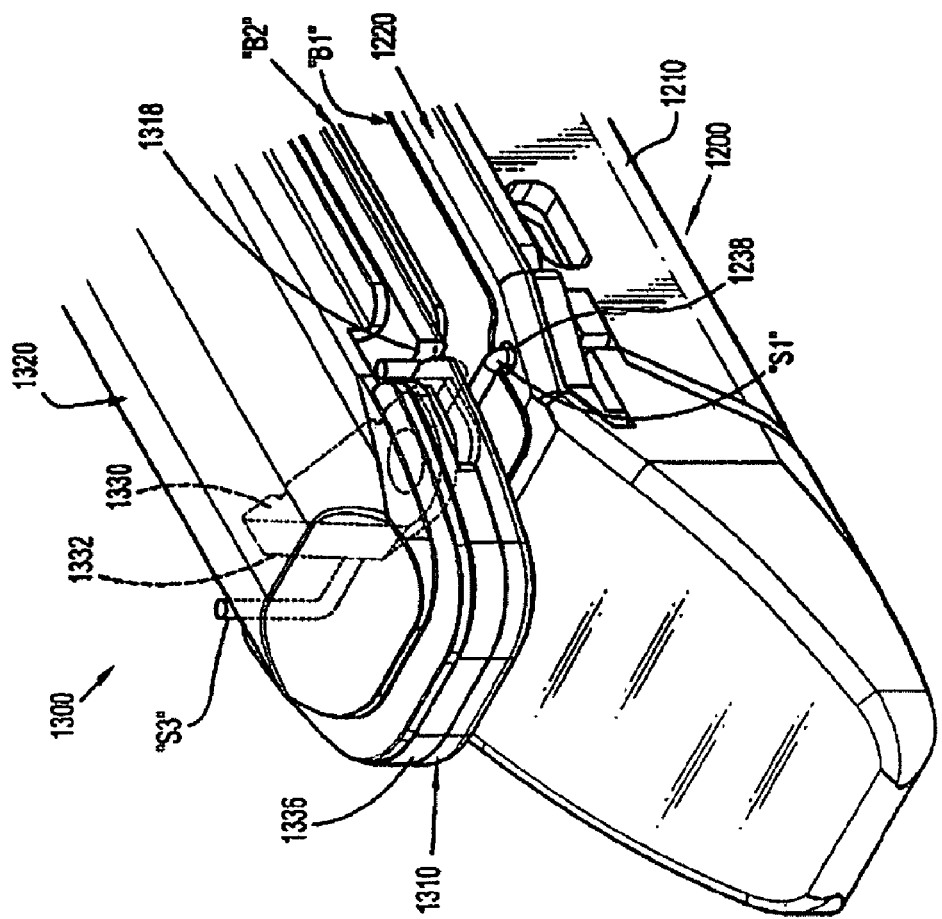
FIG. 52 is an enlarged view of the indicated area of detail of FIG. 47.
Figure 50:
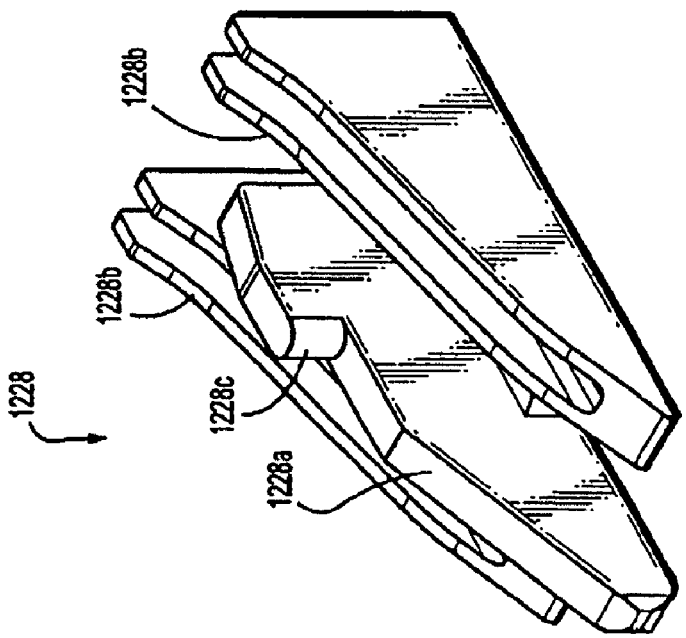
FIG. 50 is an enlarged perspective view of an actuation sled of the DLU of FIGS. 47-49.
Figure 51:
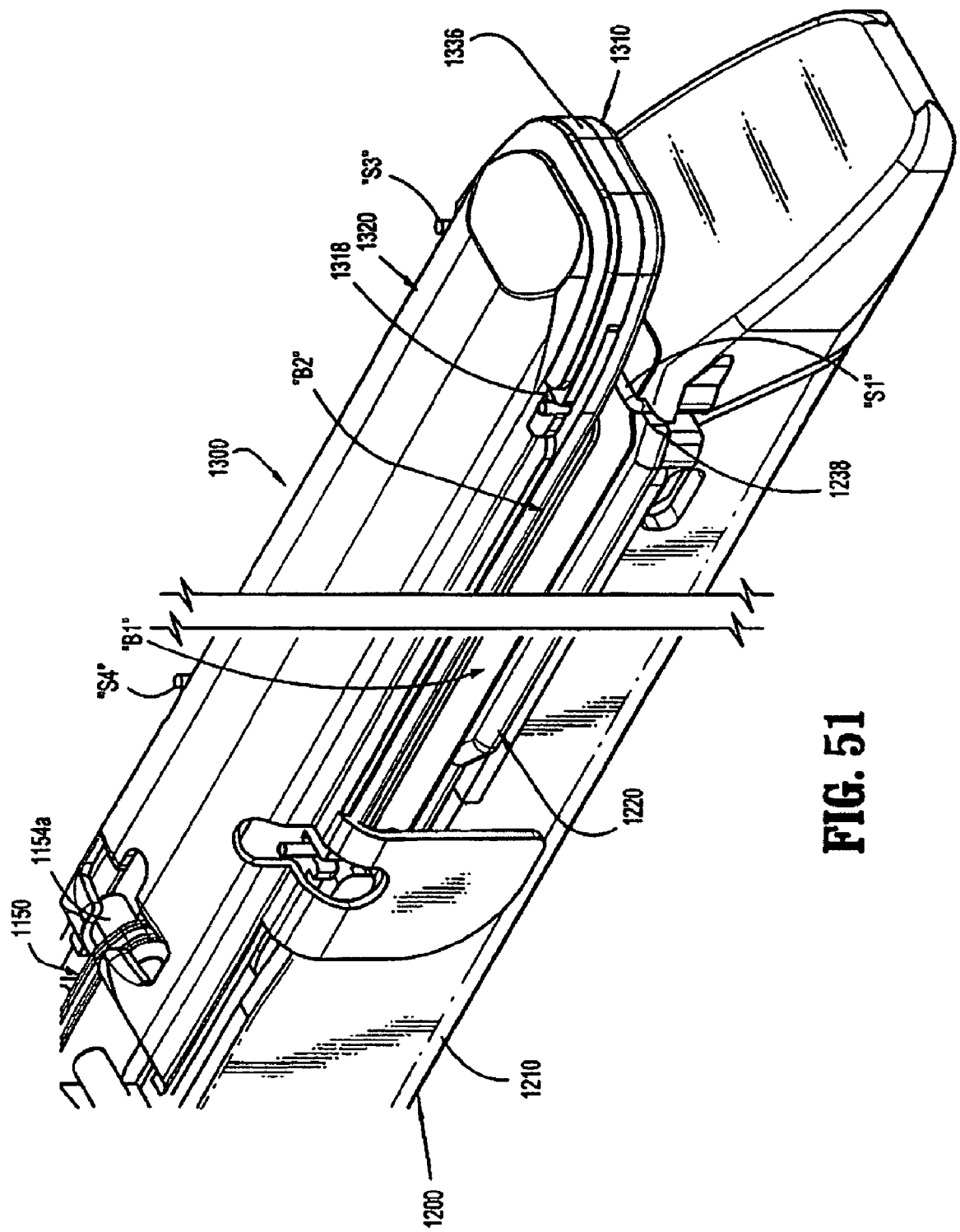
FIG. 51 is an enlarged perspective view of the DLU of FIGS. 47-49, shown in a closed condition.
Figure 53:
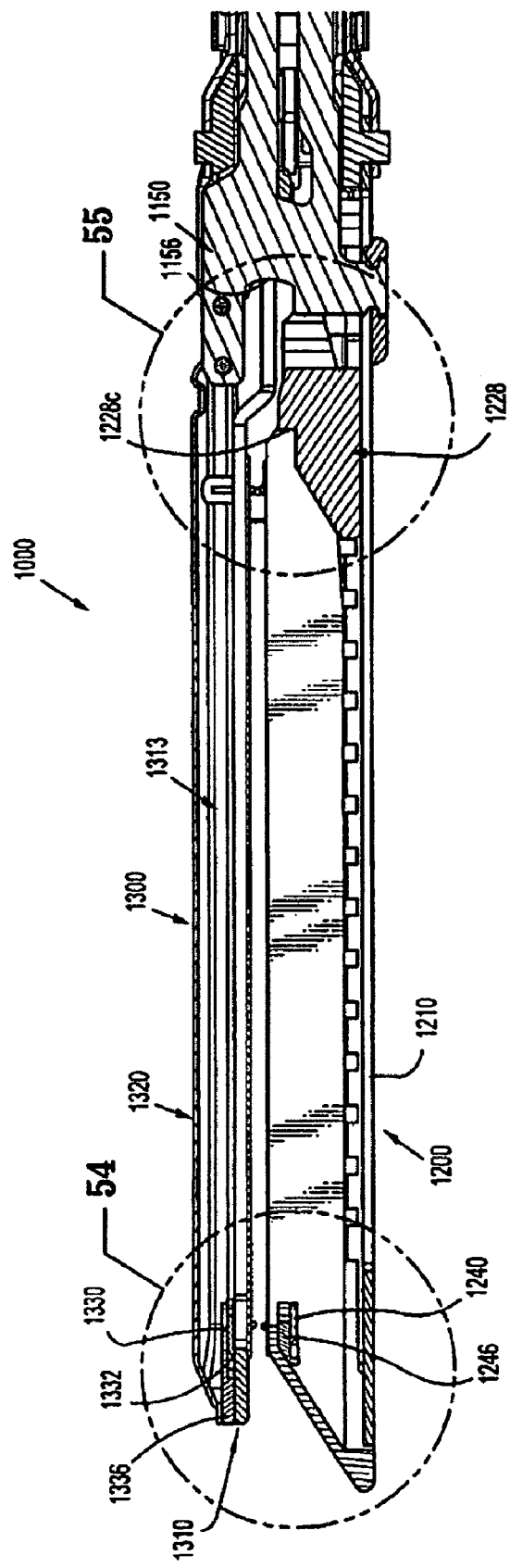
FIG. 53 is a longitudinal cross-sectional elevation view of the DLU, as taken through 53-53 of FIG. 47.
Figure 54:
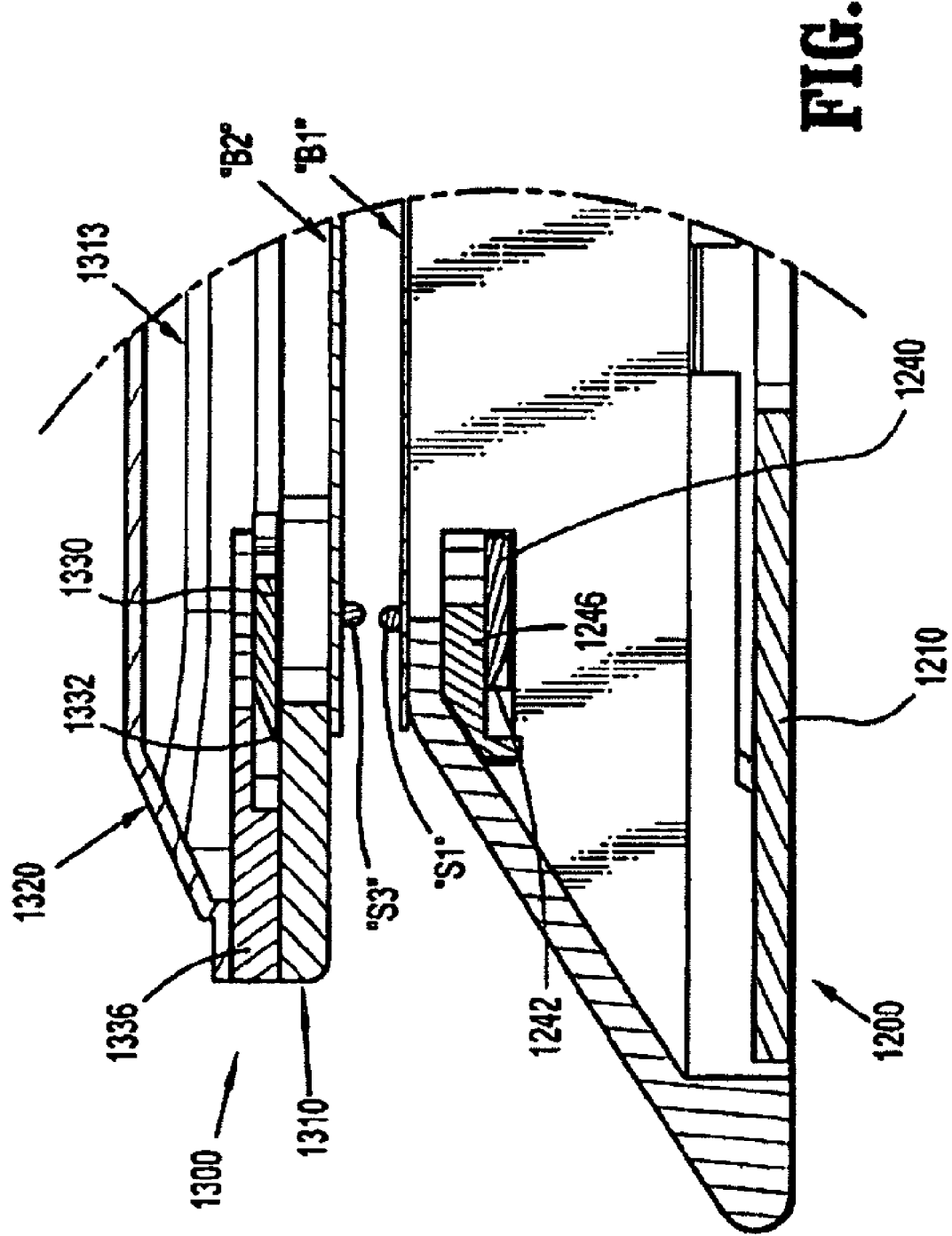
FIG. 54 is an enlarged view of the indicated area of detail of FIG. 53.
Figure 55:
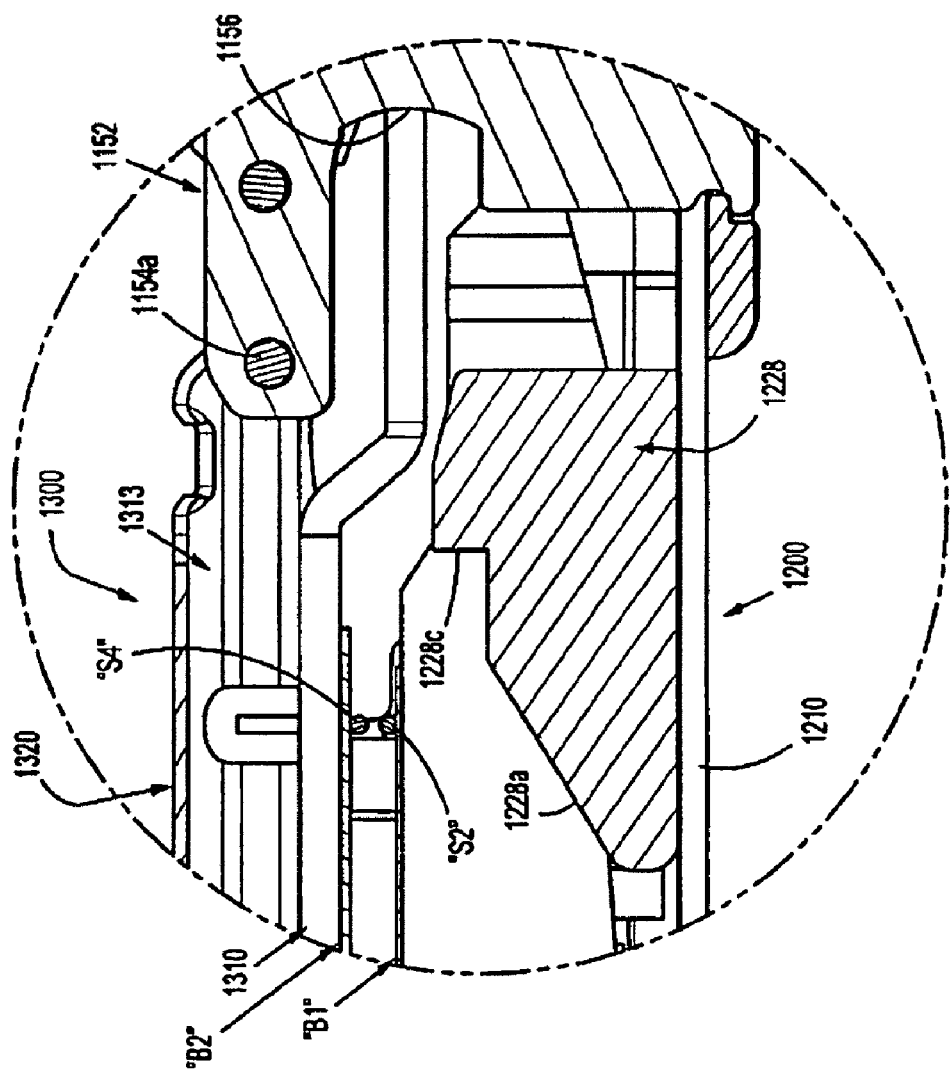
FIG. 55 is an enlarged view of the indicated area of detail of FIG. 53.

As seen in FIGS. 47-49, end effector 1000 is configured as a disposable loading unit configured for selective connection with a handle assembly (not shown).

As seen in FIG. 49, end effector 1000 includes an axial drive assembly 1150 operatively associated with and slidably disposed between cartridge assembly 1200 and anvil assembly 1300. Axial drive assembly 1150 includes an elongated drive beam 1152 having a distal end 1152a and a proximal end 1152b. Drive beam 1152 is constructed from multiple stacked beams.

Proximal end 1152b of drive beam 1152 is formed as a pair of resilient engagement fingers which are dimensioned and configured to mountingly engage a drive or control rod (not shown) when the proximal end of end effector 1000 is connected to the handle assembly.

Distal end 1152a of drive beam 1152 is configured as an I-beam including an upper and lower rail portion 1154a, 1154b, respectively, extending transversely therefrom. A distal edge of a central beam of drive beam 1152 defines a knife blade 1156.

As seen in FIGS. 49-62, cartridge assembly 1200 includes a carrier 1210 defining an elongated support channel 1212. Elongated support channel 1212 of carrier 1210 is dimensioned and configured to selectively receive a staple cartridge 1220 therein. Corresponding tabs and slots formed along staple cartridge 1220 and carrier 1210 function to retain staple cartridge 1220 within carrier 1210. Staple cartridge 1220 includes retention slots 1222 formed therein for receiving a plurality of surgical staples 1224 and pushers 1226.

As seen in FIGS. 49, 50, 53 and 55, cartridge assembly 1200 further includes an actuation sled 1228 slidably disposed between staple cartridge 1220 and carrier 1210. Actuation sled 1228 includes a central upstanding wedge or wall 1228a flanked by a pair of outer cam wedges or walls 1228b. Central wall 1228a defines a distal notch or shoulder 1228c formed therein.

As seen in FIGS. 49 and 60, a central longitudinal slot 1234 is formed in and extends along the length of staple cartridge 1220 to enable passage of drive beam 1152 therethrough. During operation of the surgical stapler, actuation sled 1228 translates along staple cartridge 1220 and carrier 1210 to advance outer cam wedges 1228b into sequential contact with pushers 1226, to cause pushers 1226 to translate vertically within retention slots 1222 and urge staples 1224 from slots 1222 into the staple forming cavities 1312 of anvil plate 1310 of anvil assembly 1300 (see FIG. 66).

Figure 56:
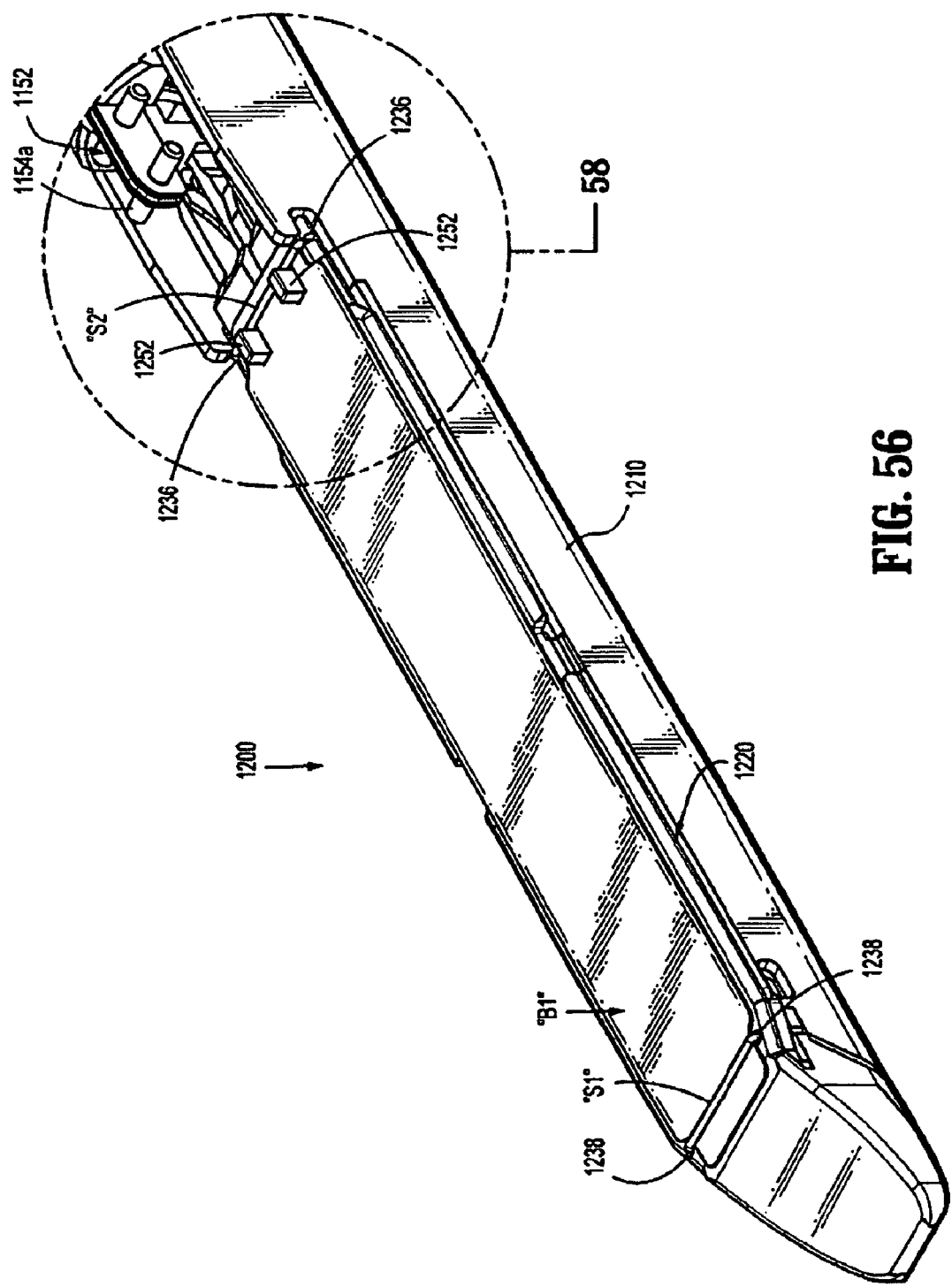
FIG. 56 is a perspective view of a cartridge assembly of the DLU of FIGS. 47-49.
Figure 57:
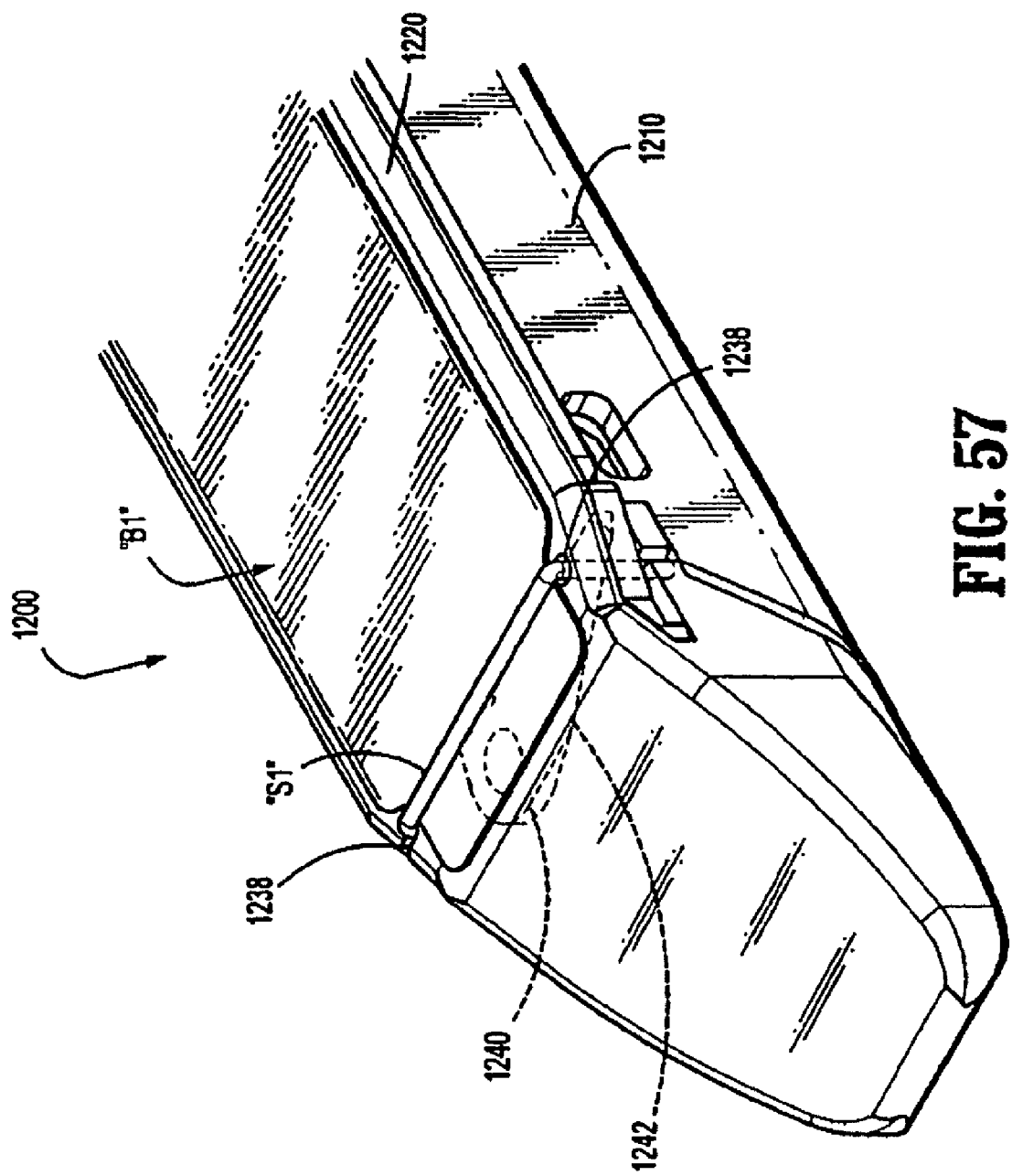
FIG. 57 is an enlarged perspective view of a distal end of the cartridge assembly of FIG. 56.
Figure 58:
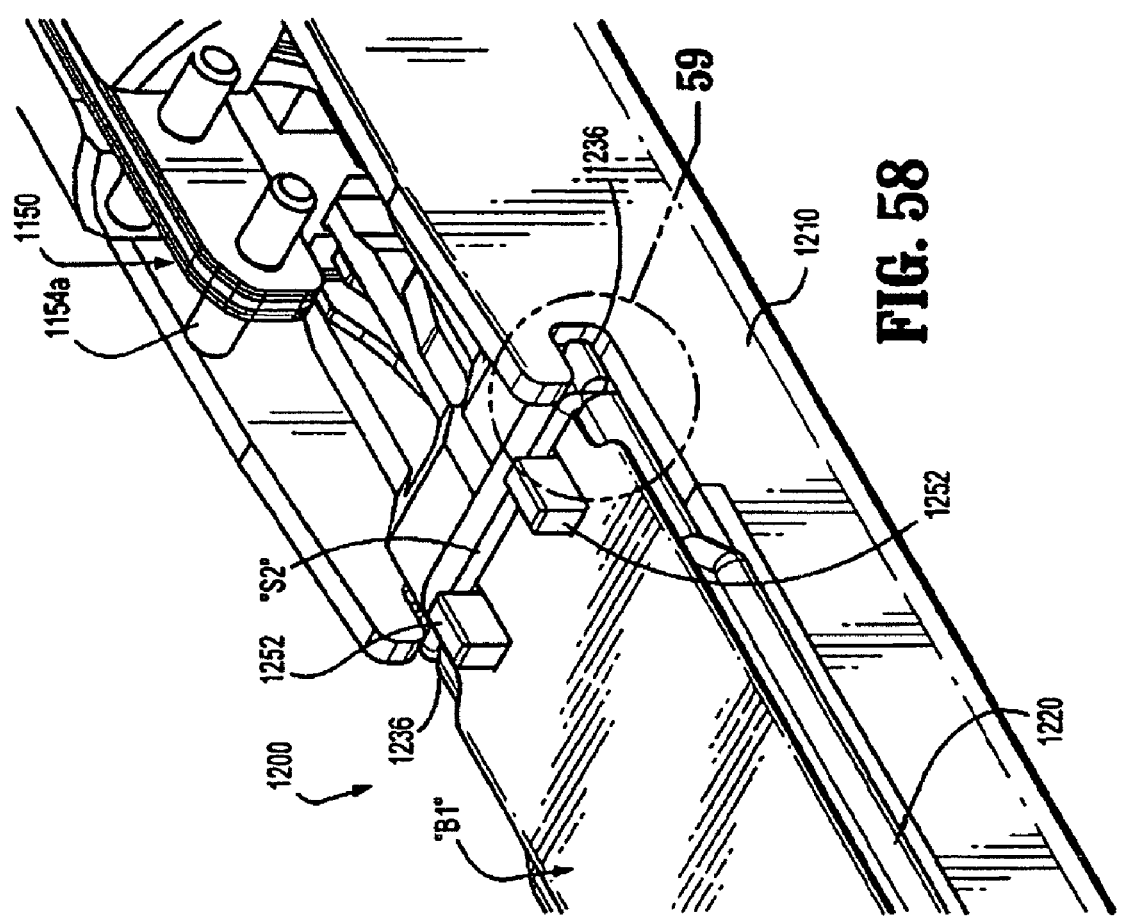
FIG. 58 is an enlarged view of the indicated area of detail of FIG. 56.
Figure 59:
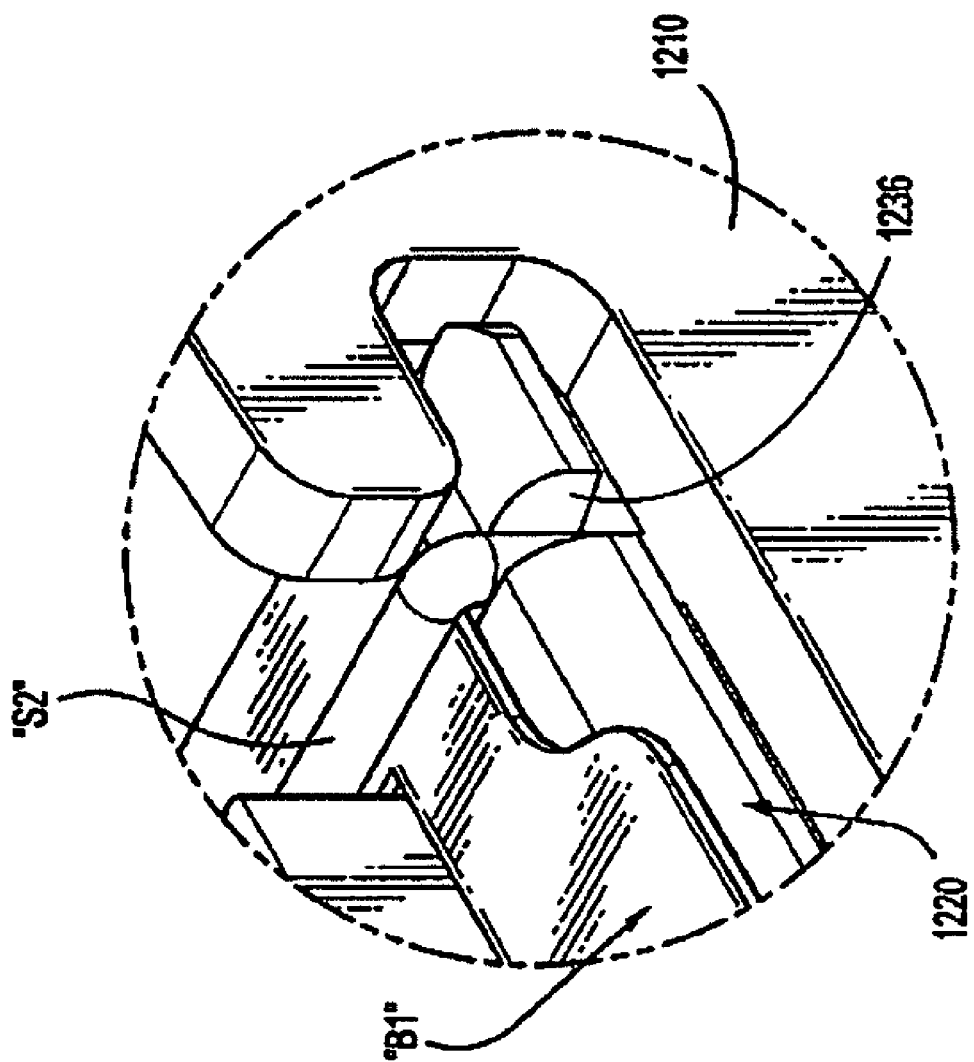
FIG. 59 is an enlarged view of the indicated area of detail of FIG. 58.
Figure 63:
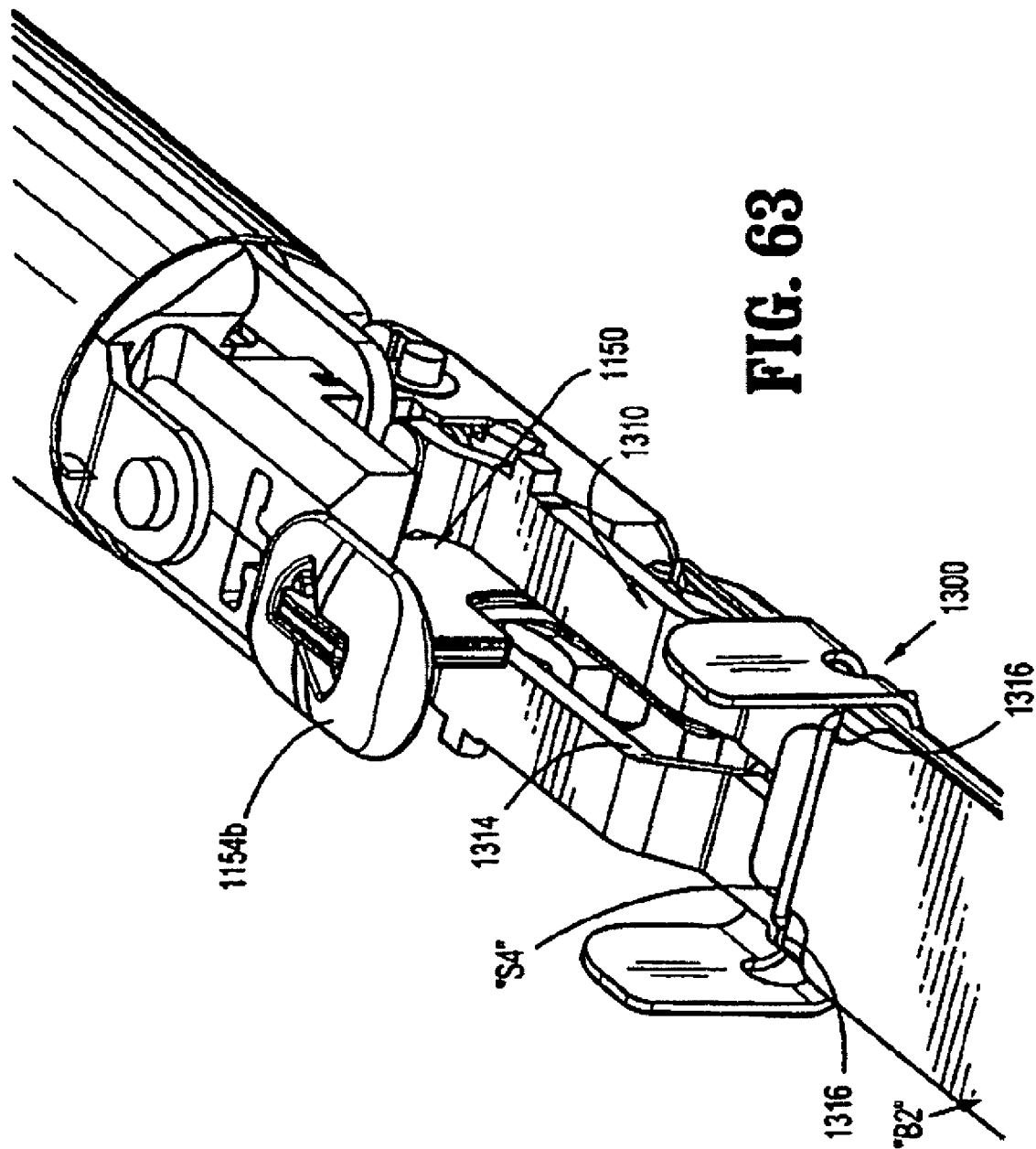
FIG. 63 is a bottom, perspective view of a proximal end of an anvil assembly of the DLU of FIGS. 47-49.

With reference to FIGS. 56-59, staple cartridge 1220 defines a proximal pair of recesses 1236 formed near a proximal end thereof and disposed, one each, on opposed sides of longitudinal slot 1234. Staple cartridge 1220 further defines a distal pair of recesses 1238 formed near a distal end thereof and disposed, one each, on opposed sides of longitudinal slot 1234. As seen in FIGS. 57-59, at least one recess of each of the proximal pair of recesses 1236 and the distal pair of recesses 1238 is in the form of a slot or notch having a constricting profile so as to frictionally engage and/or pinch a suture "S".

As seen in FIGS. 49, 53, 54, 57 and 60-62, cartridge assembly 1200 further includes a knife blade 1240 defining a distally oriented knife edge 1242 and being pivotally supported in staple cartridge 1220. Knife blade 1240 has an initial or first condition wherein knife edge 1242 is positioned proximal of one of the distal pair of recesses 1238 and a final or second condition wherein knife edge 1242 is positioned distal of the one of the distal pair of recesses 1238.

Cartridge assembly 1200 includes a knife blade housing 1246 supported in staple cartridge 1220 at a location associated with the distal pair of recesses 1238. As seen in FIG. 61, knife blade housing 1246 includes a hub 1246a onto which knife blade 1240 is rotatably connected.

As seen in FIGS. 49, 51, 52 and 54-59, cartridge assembly 1200 further includes a surgical cartridge buttress "B1" operatively secured to an upper surface of staple cartridge 1220, by sutures "S", to overlie at least some of retention slots 1222 and/or at least a portion of a length of longitudinal slot 1234. Surgical cartridge buttress "B1" includes a proximal end portion in the form of tongue "B1a" having a transverse width dimension which is less than a transverse width dimension of surgical cartridge buttress "B1", and a distal end portion in the form of tongue "B1b" having a transverse width dimension which is less than the transverse width dimension of surgical cartridge buttress "B1". The proximal end portion "B1a" of surgical cartridge buttress "B1" defines a pair of apertures "B1c" formed therein for receiving posts 1252 of staple cartridge 1220 therein. A first suture "S1" is threaded through each of the distal pair of recesses 1238 and around/over distal tongue "B1b" of cartridge buttress "B1" and, and a second suture "S2" is threaded through each of the proximal pair of recesses 1236 and around/over proximal tongue "B1a" of cartridge buttress "B1".

A first end of each suture "S1, S2" is anchored or fixed in a respective one recesses of the proximal and distal pair of recesses 1236, 1238 while a second end of each suture "S1, S2" passes transversely across respective distal and proximal tongues "B1b, B1a" of cartridge buttress "B1" and is anchored or fixed in a respective other recess of the proximal and distal pair of recesses 1236, 1238.

As seen in FIGS. 49, 56 and 58, staple cartridge 1220 includes a pair of spaced apart posts 1252 disposed on opposed sides of longitudinal slot 1234. Posts 1252 are located distal of and adjacent to proximal suture "S2". Posts 1252 are received in openings formed in cartridge buttress "B1". Posts 1252 function to maintain the position of cartridge buttress "B1" relative to staple cartridge 1220 as drive assembly 1150 is moved distally. Posts 1252 also function to brace proximal sutures "S2" as drive assembly 1150 is moved distally.

As seen in FIGS. 49, 51-55 and 63-67, anvil assembly 1300 includes an anvil plate 1310 having a plurality of staple deforming pockets/cavities 1312 (see FIG. 66) and a cover plate 1320 secured to a top surface of anvil plate 1310, wherein a cavity 1313 is defined therebetween. The cavity defined between anvil plate 1310 and cover plate 1320 is dimensioned to slidably receive upper rail portion 1154a of drive beam 1152 therein. A longitudinal slot 1314 extends through anvil plate 1310 to facilitate passage of drive beam 1152 therethrough.

In operation, an upper surface of anvil plate 1310 defines a camming surface 1310a against which upper rail portion 1154a of drive beam 1152 engages to cam, urge and clamp anvil assembly 1300 against the tissue as drive assembly 1150 advances drive beam 1152 through longitudinal slot 1314.

With continued reference to FIGS. 49, 51, 52 and 63-67, anvil plate 1310 defines a proximal pair of recesses 1316 formed near a proximal end of anvil plate 1310 and disposed, one each, on opposed sides of longitudinal slot 1314. Anvil plate 1310 defines a distal pair of recesses 1318 formed near a distal end of anvil plate 1310 and disposed, one each, on opposed sides of longitudinal slot 1314. At least one recess of each of the proximal pair of recesses 1316 and the distal pair of recesses 1318 is in the form of a slot or notch having a constricting profile so as to frictionally engage and/or pinch a suture "S".

As seen in FIGS. 49, 51-54 and 64-67, anvil assembly 1300 further includes a knife blade 1330 defining a distally oriented knife edge 1332 and being pivotably interposed within the cavity defined between anvil plate 1310 and cover plate 1320. Knife blade 1330 has an initial or first condition wherein knife edge 1332 is positioned proximal of one of the distal pair of recesses 1318 and a final or second condition wherein knife edge 1332 is positioned distal of the one of the distal pair of recesses 1318.

Figure 64:
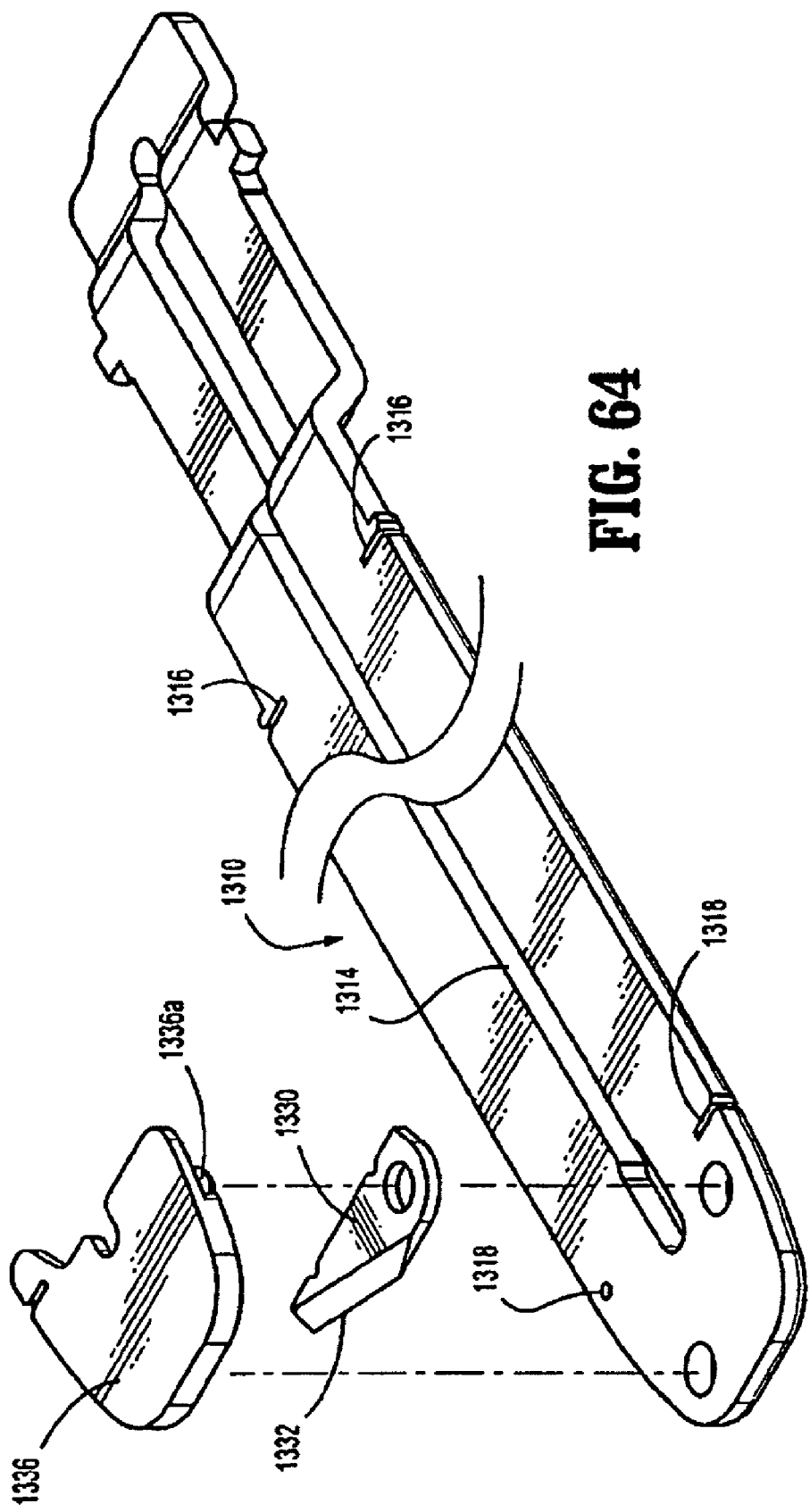
FIG. 64 is a perspective view, with parts separated, of the anvil assembly of FIG. 63.
Figure 65:
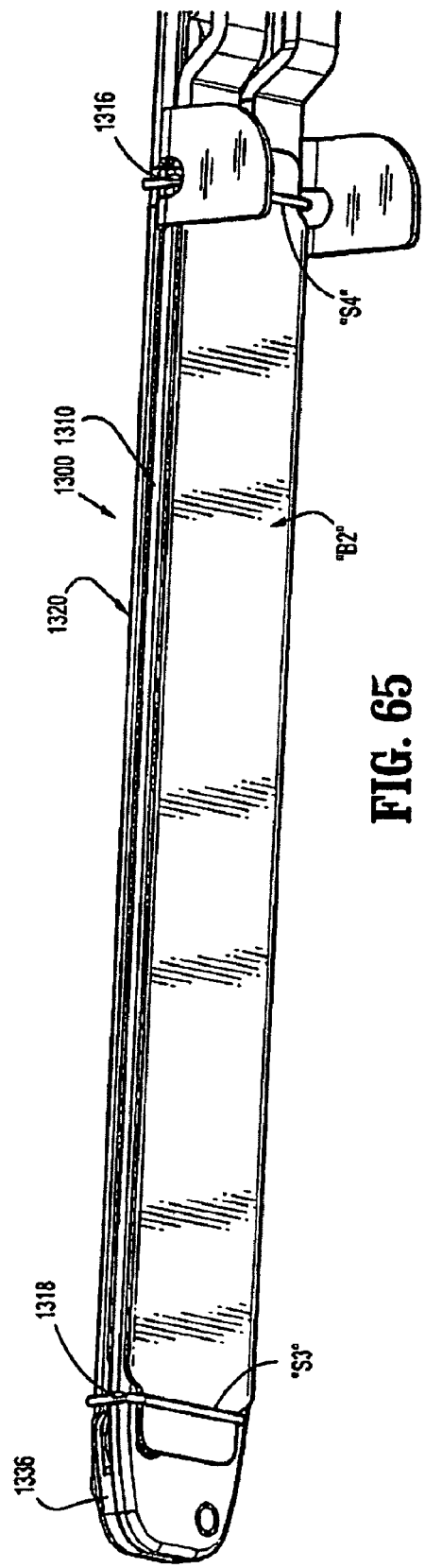
FIG. 65 is a bottom, perspective view of the anvil assembly of FIGS. 63 and 64.
Figure 73:
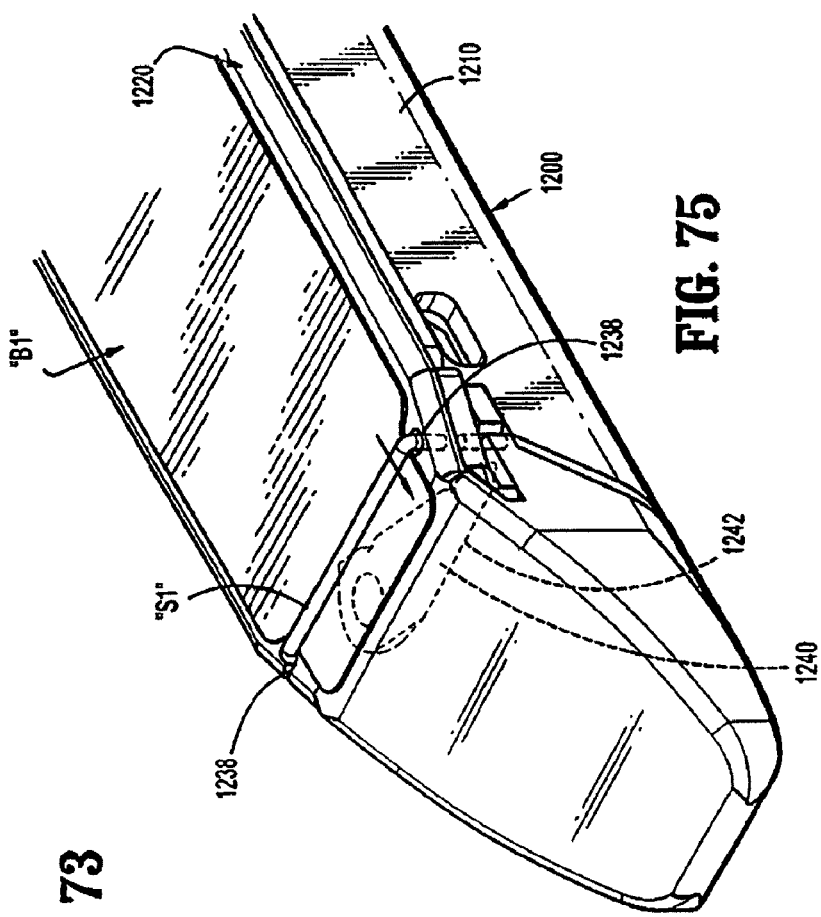
FIG. 73 is a schematic, perspective illustration of the actuation sled engaging a knife blade assembly.
Figure 74:
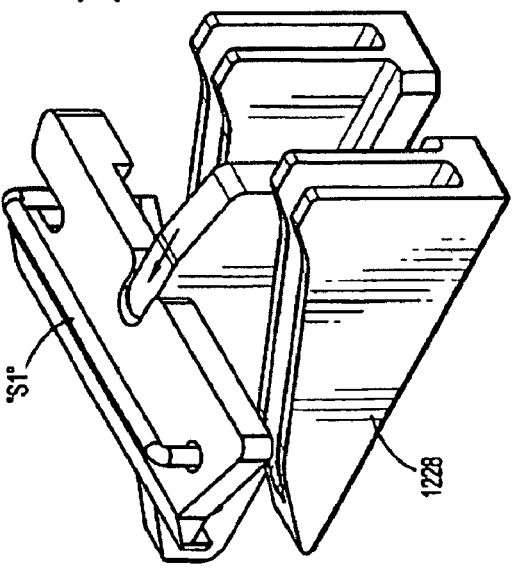
FIG. 74 is a top, plan view of the actuation sled engaging a knife blade assembly.
Figure 75:
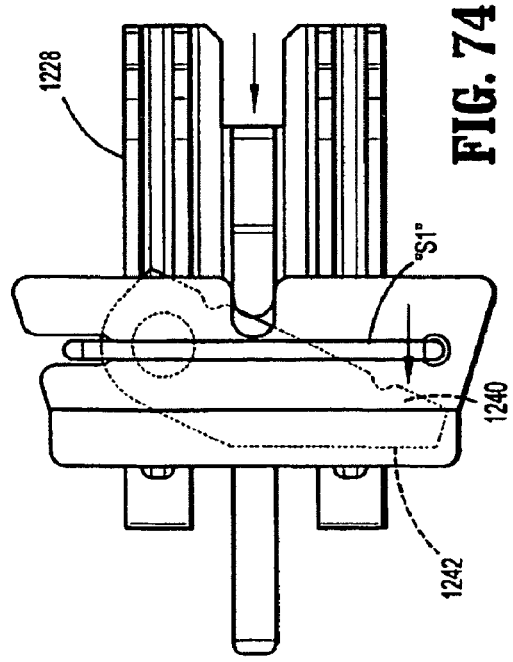
FIG. 75 is an enlarged perspective view of a distal end of the cartridge assembly following a complete actuation of the drive assembly.

As seen in FIGS. 49, 51-54 and 64-67, anvil assembly 1300 includes a knife blade housing 1336 supported between anvil plate 1310 and cover plate 1320 at a location associated with the distal pair of recesses 1318. As seen in FIGS. 64 and 67, knife blade housing 1336 includes a hub 1336a onto which knife blade 1330 is rotatably connected.

Anvil assembly 1300 further includes a surgical anvil buttress "B2" operatively secured to a lower surface of anvil plate 1310, by sutures "S", to overlie at least some of anvil pockets 1312a and/or at least a portion of a length of longitudinal slot 1314. Surgical anvil buttress "B2" includes a proximal end portion in the form of tongue "B2a" having a transverse width dimension which is less than a transverse width dimension of surgical anvil buttress "B2", and a distal end portion in the form of tongue "B2b" having a transverse width dimension which is less than the transverse width dimension of surgical anvil buttress "B2". A first suture "S3" is threaded through each of the distal pair of recesses 1318, and a second suture "S4" is threaded through each of the proximal pair of recesses 1316.

A first end of suture "S3" is anchored or fixed in a recess of the distal pair of recesses 1318 and a second end of suture "S3" passes around/over distal tongue "B2b" of anvil buttress "B2", transversely thereacross anvil buttress "B2", so as to be anchored or fixed in the other recess of the distal pair of recesses 1318.

A first end of suture "S4" is anchored or fixed in a recess of the proximal pair of recesses 1316 while a second end of suture "S4" passes around/over proximal tongue "B2a" of anvil buttress "B2" and is anchored or fixed in the other recess of the proximal and pair of recesses 1316.

As seen in FIGS. 47-49, 51, 63 and 65-67, cover plate 1320 of anvil assembly 1300 includes a pair of walls 1322 extending in a direction of anvil plate 1310. Walls 1322 are formed near a proximal end of cover plate 1320 and extend from opposed side edges thereof. Walls 1322 are configured such that when cartridge assembly 1200 and anvil assembly 1300 are in a closed or clamped condition, walls 1322 extends across a tissue gap defined therebetween. Walls 1322 function as tissue stops, inhibiting tissue flow in a proximal direction during a clamping or closing of end effector 1000.

In operation, as seen in FIGS. 68-72, with anvil buttress "B2" secured against the lower surface of anvil plate 1310, during firing of the surgical stapling apparatus, as drive assembly 1150 is advanced (e.g., moved from a proximal-most position to a distal-most position), knife blade 1156 slices through a central section of suture "S4", thereby freeing the proximal end of anvil buttress "B2" from anvil assembly 1300. As drive assembly 1150 approaches the distal end of anvil assembly 1300, upper rail portion 1154a of drive beam 1152 abuts against and urges knife blade 1330 to rotate distally. As knife blade 1330 is rotated distally, knife edge 1332 is rotated from the initial or first condition positioned proximal of one of the distal pair of recesses 1318 to the final or second condition positioned distal of the one of the distal pair of recesses 1318. In so doing, knife edge 1332 slices or cuts through suture "S3", thereby freeing the distal end of the anvil buttress "B2" from anvil assembly 1300.

Concomitantly therewith, in operation, as seen in FIGS. 68-75, with cartridge buttress "B1" secured against the tissue contacting surface of staple cartridge 1220, during firing of the surgical stapling apparatus, as drive assembly 1150 is advanced (e.g., moved from a proximal-most position to a distal-most position), knife blade 1156 slices through a central section of the proximal suture "S2", thereby freeing the proximal end of the cartridge buttress "B1" from cartridge assembly 1200.

As drive assembly 1150 approaches the distal end of staple cartridge 1220, shoulder 1228c of central upstanding wedge or wall 1228a of actuation sled 1228 abuts against and urges knife blade 1240 to rotate distally. As knife blade 1240 is rotated distally, knife edge 1242 is rotated from the initial or first condition positioned proximal of one of the distal pair of recesses 1238 to the final or second condition positioned distal of the one of the distal pair of recesses 1238. In so doing, knife edge 1242 slices or cuts through distal suture "S1", thereby freeing the distal end of the cartridge buttress "B1" from cartridge assembly 1200.

As drive assembly 1150 is advanced from a proximal-most position to a distal-most position, knife blade 1156 thereof slices or cuts longitudinally through both cartridge buttress "B1" and anvil buttress "B", thereby dividing the buttresses "B1, B2" substantially in half. Additionally, as drive assembly 1150 is advanced from a proximal-most position to a distal-most position, upstanding cam wedges 1228b of actuation sled 1228 actuates pushers 1226, to cause pushers 1226 to translate vertically within retention slots 1222 and urge staples 1224 from slots 1222. As staples 1224 are urged from slots 1222 of staple cartridge 1220, legs of staples 1224 penetrate and pass through both cartridge buttress "B1" and anvil buttress "B2", through any tissue (not shown) interposed between cartridge buttress "B1" and anvil buttress "B2", and are formed against or within staple deforming pockets 1312 of anvil plate 1310 of anvil assembly 1300.

Surgical buttresses "B1, B2" are each fabricated from a suitable biocompatible and bioabsorbable material. Surgical buttresses "B1, B2" are each fabricated from a non-absorbent material which does not retain fluid. Surgical buttresses "B1, B2" are each fabricated from "BIOSYN" made from GLYCOMER 631 (a block copolymer), a synthetic polyester composed of glycolide, dioxanone and trimethylene carbonate.

One block of the resulting copolymer contains randomly combined units derived from p-dioxanone(1,4-dioxan-2-one) and trimethylene carbonate(1,3-dioxan-2-one). The second block of the copolymer contains randomly combined units derived from glycolide and p-dioxanone. The resulting polyester is an ABA triblock terpolymer possessing about 60% glycolide, about 14% dioxanone, and about 26% trimethylene carbonate.

End effector 1000 is shown in FIGS. 47 and 48 as being capable of articulation about a pivot point. Cartridge assembly 1200 and anvil assembly 1300 may form a part of a non-articulating SULU.

Turning now to FIGS. 76 and 77, a surgical cartridge buttress "B1," according to another embodiment of the present disclosure, is shown operatively secured to a tissue side of the staple cartridge 220. The surgical cartridge buttress "B1" includes a proximal end portion "B1b," in the form of a tongue, having a transverse width dimension that is less than a transverse width dimension of a central body portion "B1a" of the surgical cartridge buttress "B1;" and a distal end portion "B1c," in the form of a tongue, also having a transverse width dimension that is less than the transverse width dimension of central body portion "B1a" of surgical cartridge buttress "B1."

The proximal tongue "B1b" of surgical cartridge buttress "B1" of FIGS. 76 and 77 defines a pair of lateral notches "B1d, B1e" formed in a rear edge thereof, and a central notch "B1f" formed in a rear edge thereof between lateral notches "B1d, B1e" and located along a center line of surgical cartridge buttress "B1." Lateral notches "B1d, B1e" are sized to receive posts 252 projecting from of staple cartridge 220. Central notch "B1f" has a triangular or V-shape configuration for providing a lead in for the knife during a cutting of surgical cartridge buttress "B1."

Surgical cartridge buttress "B1" of FIGS. 76 and 77 further includes a pair of lateral recesses "B1h, B1i" formed in the lateral side edges of body portion "B1a," near a proximal end thereof; and a pair of lateral recesses "B1j, B1k" formed in the lateral side edges of body portion "B1a," near a distal end thereof. Each recess is substantially triangular in shape and is dimensioned to extend beyond the respective proximal and distal pair of recesses 236, 238 of staple cartridge 220.

Figure 78:
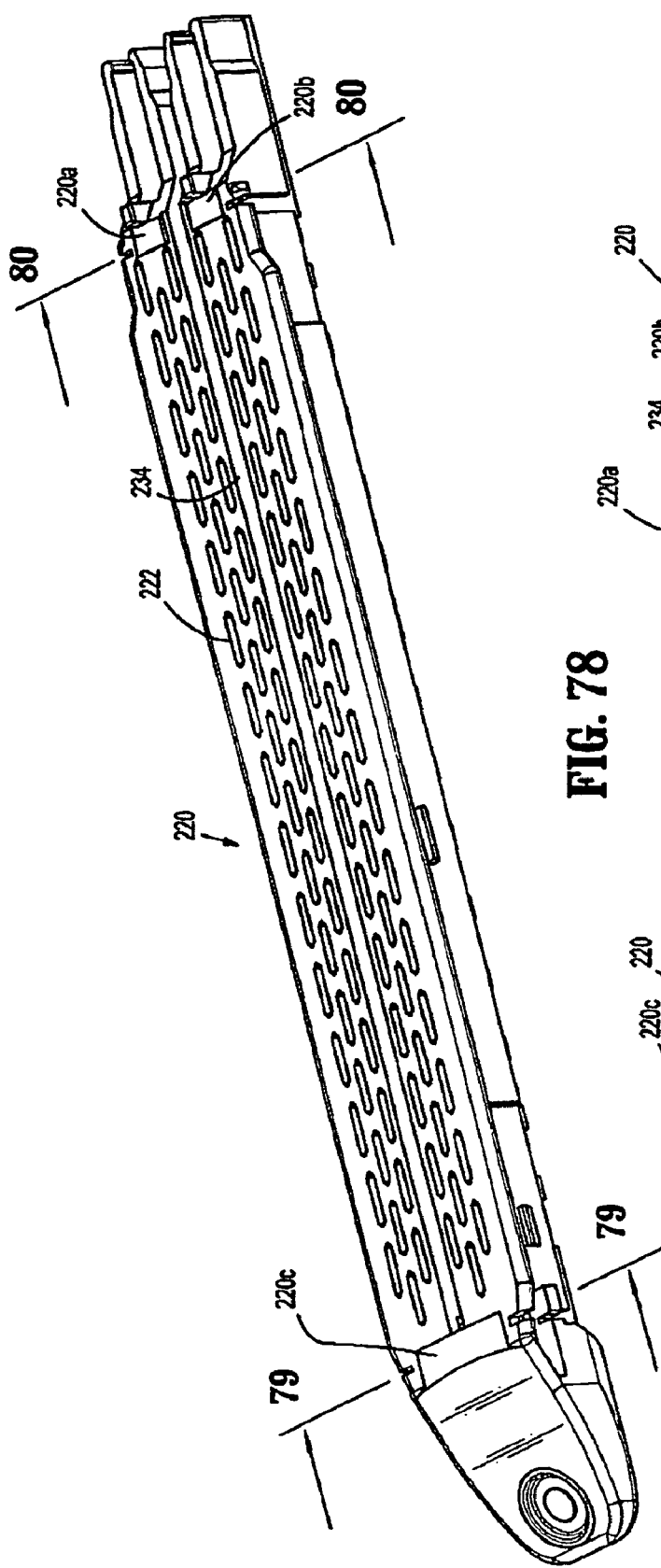
FIG. 78 is a perspective view of the cartridge assembly of FIGS. 76-77, with the surgical cartridge buttress removed therefrom.
Figure 80:
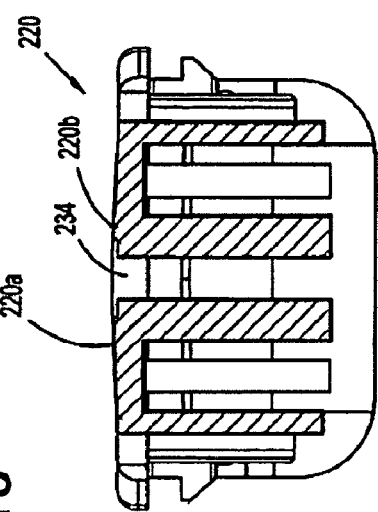
FIG. 80 is a cross-section view taken through 80-80 of FIG. 78.
Figure 79:
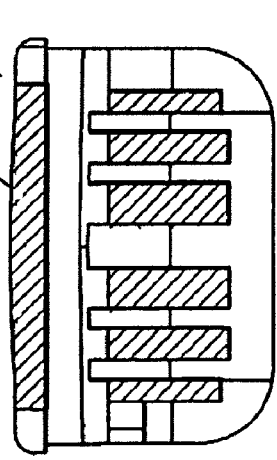
FIG. 79 is a cross-section view taken through 79-79 of FIG. 78.

As seen in FIGS. 78-80, staple cartridge 220 defines a central longitudinal slot 234, and a plurality of rows of staple retention slots 222 formed on either side of central longitudinal slot 234. Staple cartridge 220 includes a pair of proximal pads 220a, 220b projecting from an upper surface thereof. Pads 220a, 220b are disposed on opposite sides of longitudinal slot 234, near a proximal end thereof. Staple cartridge 220 further includes a distal pad 220c projecting from an upper surface thereof. Pad 220c is disposed distally of longitudinal slot 234. In use, pads 220a-220c enhance a gripping effect between surgical cartridge buttress "B1" and staple cartridge 220 when surgical cartridge buttress "B1" is cinched thereto by the sutures.

Figure 81:
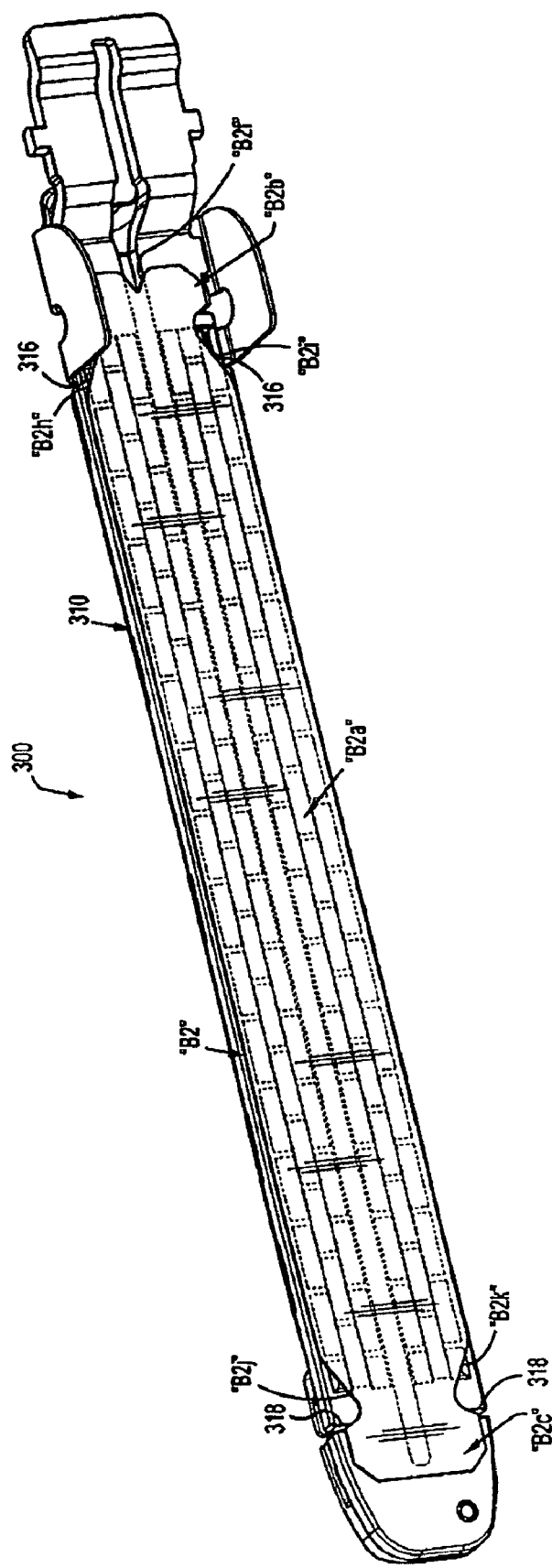
FIG. 81 is a perspective view of an anvil assembly of a DLU according to another embodiment of the present disclosure, including a surgical anvil buttress according to another embodiment of the present disclosure.

Turning now to FIG. 81, a surgical anvil buttress "B2" according to another embodiment of the present disclosure is shown operatively secured to a tissue side of the anvil plate 310 of anvil assembly 300. The surgical anvil buttress "B2" of FIG. 81 includes a proximal end portion "B2b," in the form of a tongue, having a transverse width dimension that is less than a transverse width dimension of a central body portion "B2a" of the surgical anvil buttress "B2;" and a distal end portion "B2c," in the form of a tongue, also having a transverse width dimension that is less than the transverse width dimension of central body portion "B2a" of surgical anvil buttress "B2."

Figure 82:
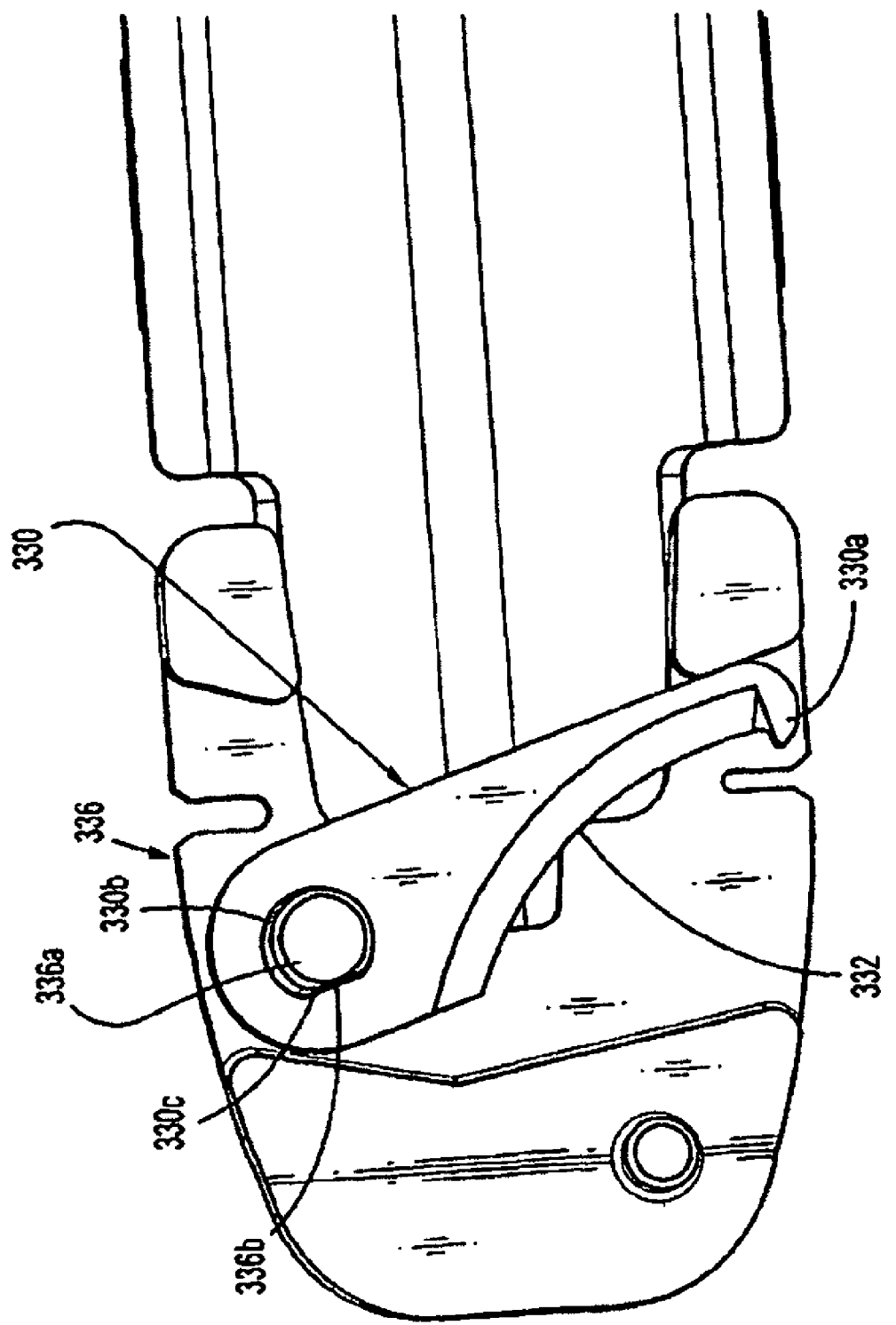
FIG. 82 is a plan view of a distal end of the anvil assembly of FIG. 81, with an anvil plate removed therefrom, illustrating a knife blade housing supporting an anvil knife blade thereon.

As seen in FIG. 82, proximal tongue "B2b" of surgical anvil buttress "B2" defines a central notch "B2f" formed in a rear edge thereof and located along a center line of surgical anvil buttress "B2." Central notch "B2f" has a triangular or V-shape.

Surgical anvil buttress "B2" as seen in FIG. 82 further includes a pair of lateral recesses "B2h, B2i" formed in the lateral side edges of body portion "B2a," near a proximal end thereof; and a pair of lateral recesses "B2j, B2k" formed in the lateral side edges of body portion "B2a," near a distal end thereof. Each recess is substantially triangular in shape and is dimensioned to extend beyond the respective proximal and distal pair of recesses 316, 318 of anvil plate 310 of anvil assembly 300.

As seen in FIGS. 82-84A, anvil knife blade 330 may be configured to include a distally oriented, double-beveled, knife edge 332 having a concave profile. Anvil knife blade 330 includes a distally extending finger or tooth 330a formed at a free end thereof.

Anvil knife blade 330 defines a substantially circular aperture 330b, including a flattened portion 330c, formed in an end thereof. Aperture 330b is configured to receive a hub 336a of a knife blade housing 336 including a complementarily shaped flattened portion 336b. In use, flattened portion 330c of anvil knife blade 330 mates with the complementary flattened portion 336b of hub 336a to help maintain the relative orientation of anvil knife blade 330 prior to an actuation by the drive assembly.

Figure 83:
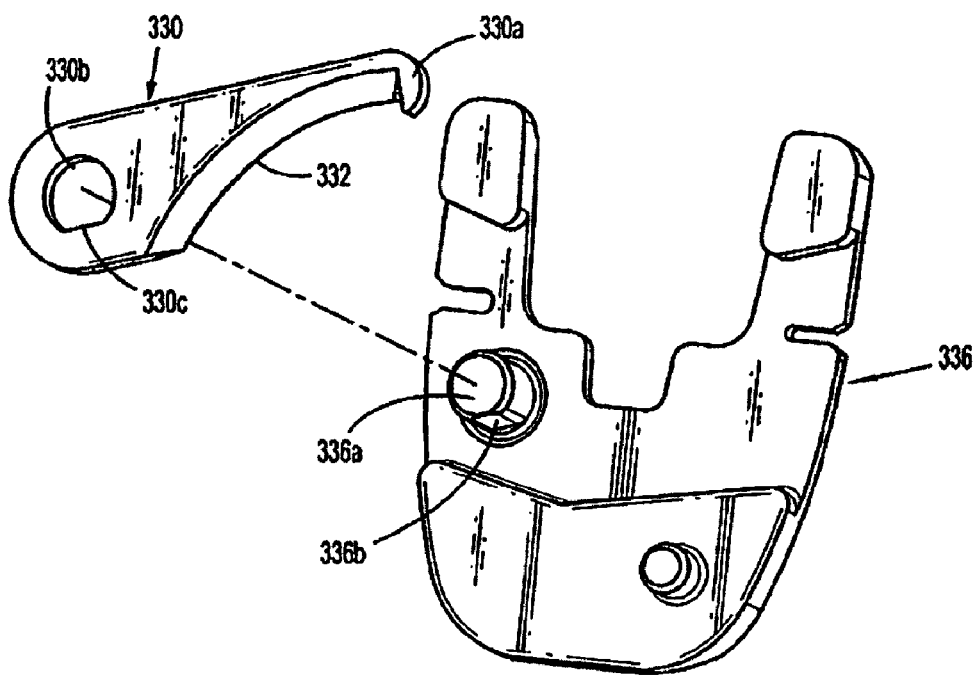
FIG. 83 is a perspective view, with parts separated, of the knife blade housing and anvil knife blade of FIG. 82.
Figures 84, 84A:
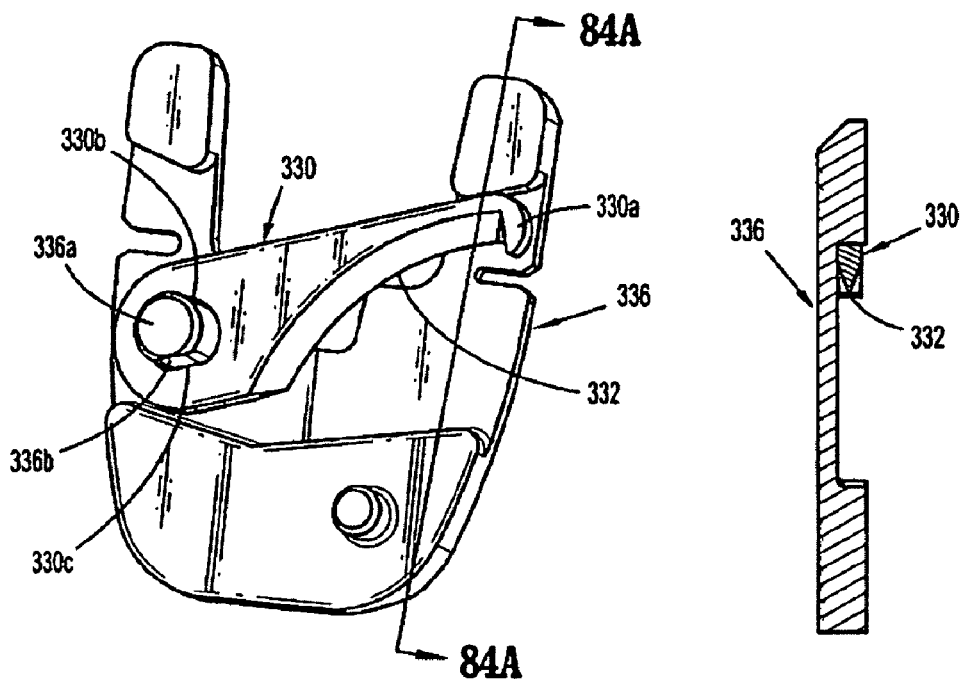
FIG. 84 is a perspective view of the knife blade housing and anvil knife blade of FIGS. 82 and 83, shown in an assembled condition.
FIG. 84A is a cross-sectional view as taken through 84A-84A of FIG. 84.

As seen in FIGS. 82-84, knife blade housing 336 includes a pair of extensions or legs, for a 12 mm DLU or SULU, and only a single leg or extension (see FIG. 86), for a 15 mm DLU or SULU.

Figure 85:
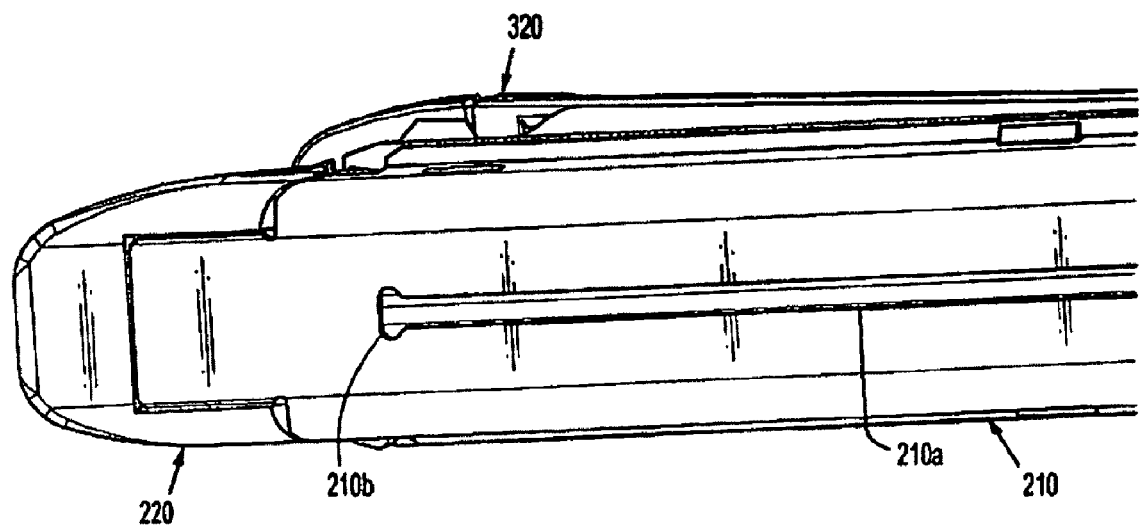
FIG. 85 is a bottom perspective view of the cartridge assembly of FIGS. 76-78.

As seen in FIG. 85, cartridge carrier 210 may include a longitudinally extending slot 210a terminating in an enlarged distal end 210b. Distal end 210b has a transverse width dimension that is greater than a transverse width dimension of slot 210a. The width dimension of distal end 210b has been enlarged to make sure the drive bar stops on a flat surface as compared to a full round configuration and provides more control of overall stroke of the drive bar.

As seen in FIGS. 76 and 78, staple cartridge 220 defines a distal pair of recesses, formed in side edges thereof, for receiving a suture therein, wherein each recess is a constricting slot for cinched receipt of the suture. As seen in FIG. 81, anvil assembly 300 and anvil plate 310 define a distal pair of recesses 318, formed in side edges thereof, for receiving a suture therein, wherein each recess 318 is a constricting slot for cinched receipt of the suture.

Figure 87:
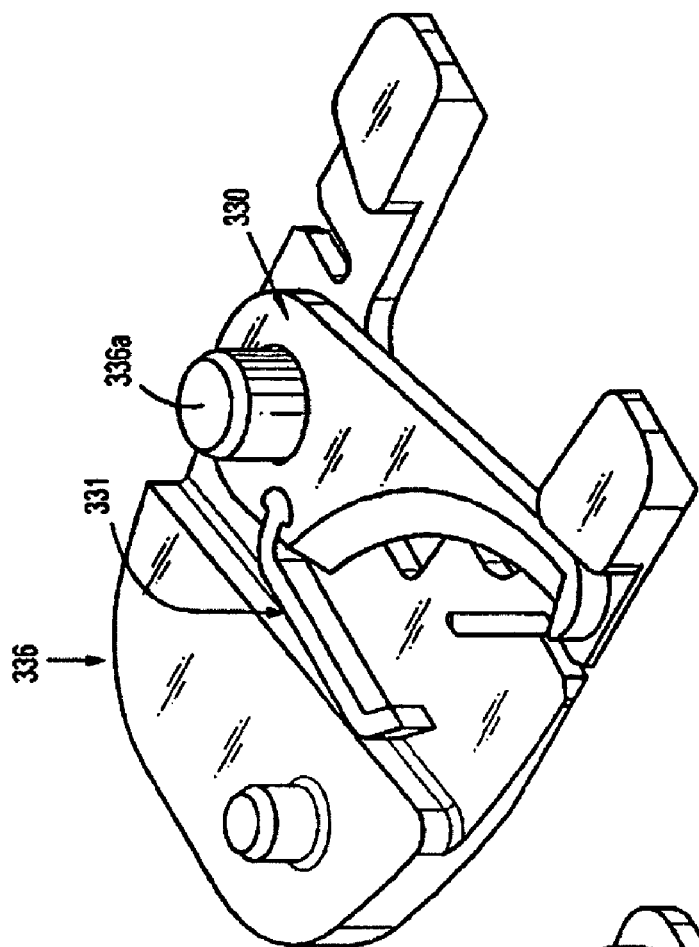
FIG. 87 is a perspective view of an anvil blade housing according to yet another embodiment of the present disclosure including an anvil knife blade rotatable connected thereto and supported thereon.
Figure 86:
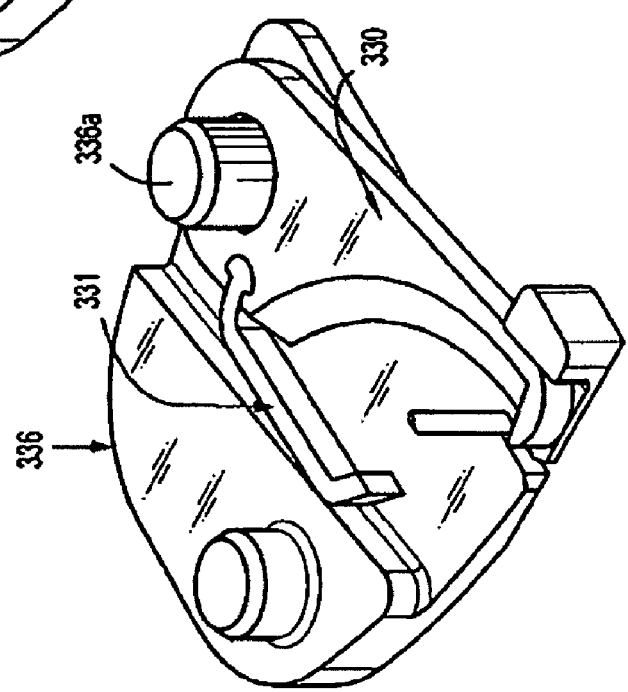
FIG. 86 is a perspective view of an anvil blade housing according to another embodiment of the present disclosure including an anvil knife blade rotatable connected thereto and supported thereon.
Figure 88:
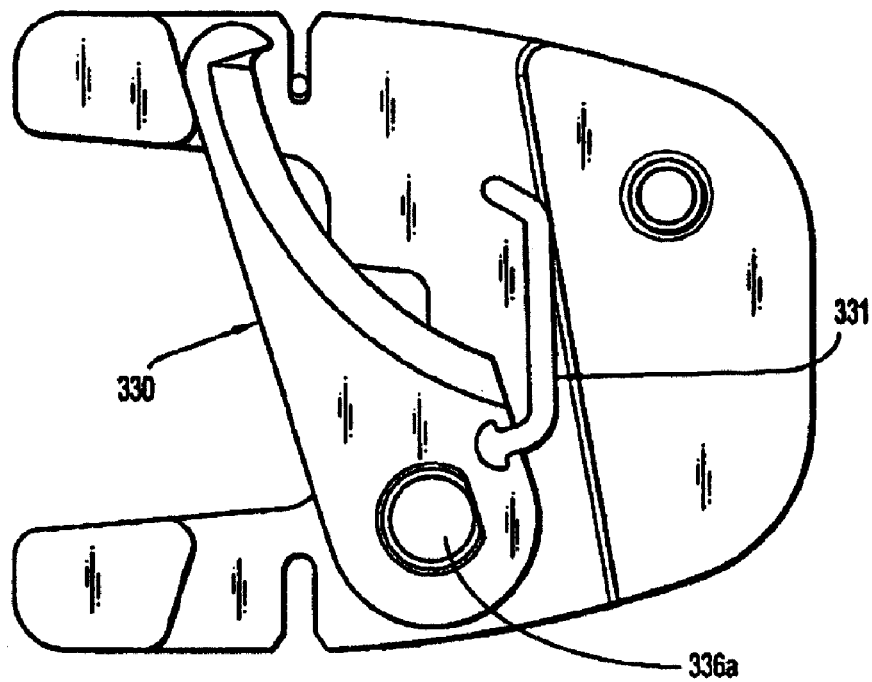
FIG. 88 is a plan view of the anvil blade housing and anvil blade of FIG. 87, shown in an unactuated condition.
Figure 89:
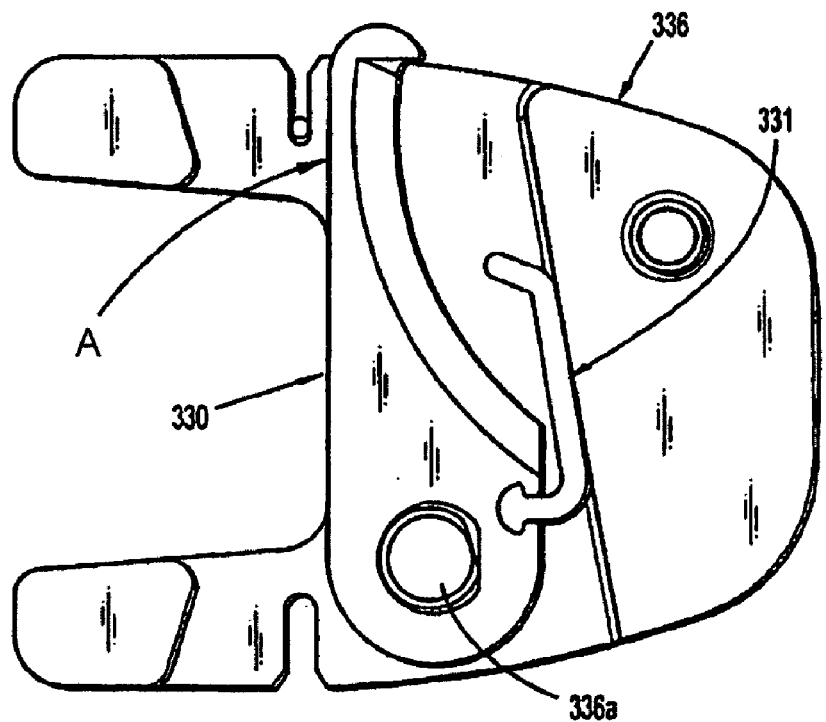
FIG. 89 is a plan view of the anvil blade housing and anvil blade of FIGS. 87 and 88, shown in an actuated condition.

As seen in FIGS. 86 and 87, anvil knife blade 330 is supported on knife blade housing 336, for either a 12 mm DLU/SULU or a 15 mm DLU/SULU, in a biased manner. In particular, a resilient member 331 is interposed between anvil knife blade 330 and a surface of knife blade housing 336 in such a manner so as to maintain anvil knife blade 330 in a first position disposed proximal of the suture or either of the distal pair of suture receiving recesses thereof prior to any firing of the surgical instrument. As seen in FIGS. 86 and 87, resilient member 331 may be in the form of a leaf spring including a first end connected to anvil knife blade 330 and a second end in contact with a surface of knife blade housing 336. In operation, as drive assembly 50 (see FIG. 2) is driven distally, the upper rail 64a of I-beam 60 (see for example FIGS. 4 and 5) abuts against and urges anvil knife blade 330 distally ("A"), thus rotating anvil knife blade 300 across the suture to sever the suture, and thereby releasing a distal end of the surgical anvil buttress. In doing so, leaf spring 331 is biased or deflected.

Figure 90:
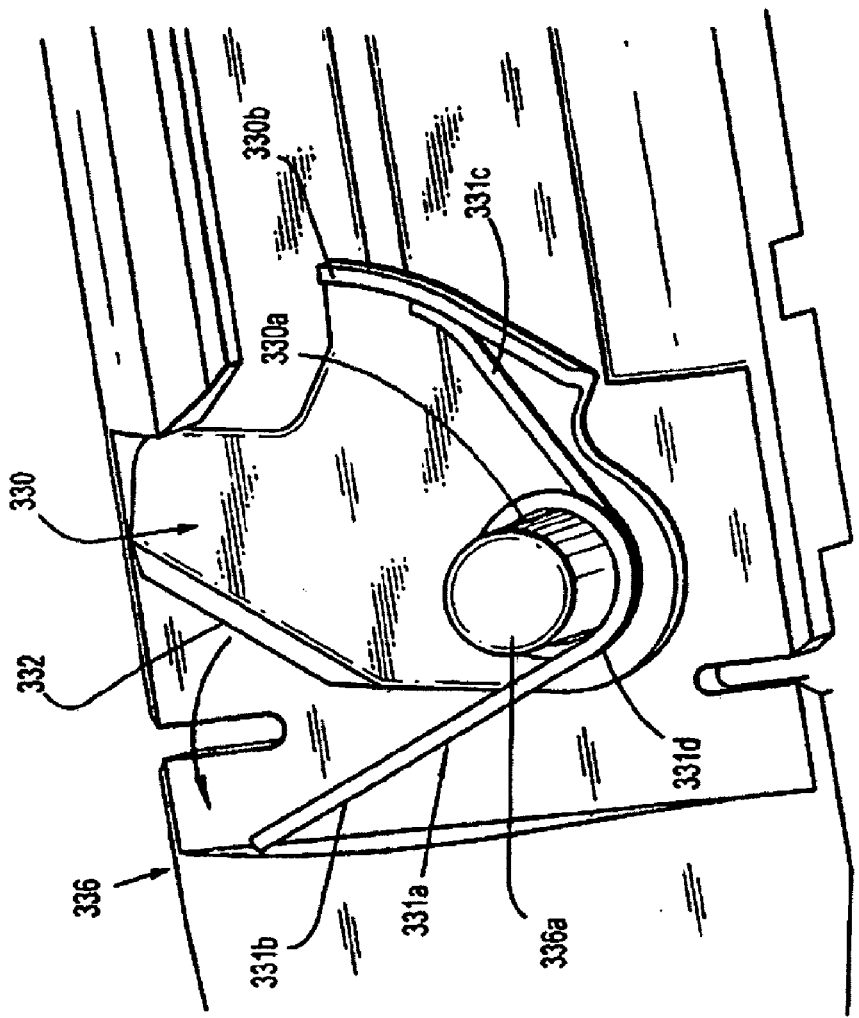
FIG. 90 is a perspective view of an anvil blade according to a further embodiment of the present disclosure.

In an alternate embodiment, as seen in FIG. 90, a resilient member 331a may be in the form of a coil spring including a first leg 331b in contact with a surface of knife blade housing 336, a second leg 331c in contact with a surface 330b of anvil knife blade 330, and a coil portion 331d positioned on hub 336a of knife blade housing 336 and interconnecting first leg 331b and second leg 331c.

In accordance with the present disclosure, it is further envisioned and contemplated that at least one of surgical cartridge buttress "B1" and surgical anvil buttress "B2" may be at least partially opaque, translucent and/or transparent. In this manner, the user may be able to better view the staple line following a firing of the surgical instrument. It is further envisioned that at least one of surgical cartridge buttress "B1" and surgical anvil buttress "B2" may be photo-luminescent, dyed and/or photoresponsive/photoreactive (i.e., able to change colors) in the presence of blood or the like.

While the above-described embodiments surgical staplers incorporating the use of movable knife blades to sever and release surgical buttresses from the tissue contacting surfaces of the anvil assembly and the cartridge assembly have been shown and described in relation to endoscopic surgical staplers, it is envisioned and within the scope of the present disclosure that any of the above-embodiments may be incorporated into any type of surgical stapler, including and not limited to open surgical staplers, such as, for example, linear surgical staplers; arcuate or annular surgical staplers; and transverse surgical staplers.

It will be understood that various modifications may be made to the embodiments disclosed herein. For example, the stapling apparatus need not apply staples but rather may apply two part fasteners as is known in the art. Further, the length of the linear row of staples or fasteners may be modified to meet the requirements of a particular surgical procedure. Thus, the length of a single stroke of the actuation shaft and/or the length of the linear row of staples and/or fasteners within a disposable loading unit may be varied accordingly. Therefore, the above description should not be construed as limiting, but merely as exemplifications of preferred embodiments. Those skilled in the art will envision other modifications within the scope and spirit of the claims appended thereto.

What is claimed is:

1. A surgical apparatus of the type including a handle assembly operable with a drive assembly to eject at least one staple from the surgical apparatus, the surgical apparatus comprising:
   a cartridge assembly defining a tissue contacting surface and a longitudinally extending elongate slot;
   an anvil assembly defining a tissue contacting surface and a longitudinally extending elongate slot; and
   a surgical buttress releasably secured to at least one of the tissue contacting surface of the cartridge assembly and the tissue contacting surface of the anvil assembly by at least one anchor, and
   an axial drive assembly movable for firing surgical staples from the cartridge assembly, wherein the axial drive assembly has a central knife blade slidably disposable in the longitudinally extending elongate slot of the cartridge assembly and the anvil assembly, the central knife blade being received in a notch of the surgical buttress upon an advancement of the central knife blade through the longitudinal extending slot;
   wherein at least one of the cartridge assembly and the anvil assembly including:
      a pair of recesses formed in a respective side edge thereof,
      wherein the anchor extends across the pair of recesses of the at least one of the cartridge assembly and the anvil assembly for securing the surgical buttress thereto,
      an other knife blade pivotably mounted on the at least one of the cartridge assembly and the anvil assembly, the other knife blade having a distally oriented knife edge and being movable from a position proximal of the pair of recesses to a position distal of the pair of recesses, the other knife blade being movable to cut the anchor.

2. The surgical apparatus according to claim 1, wherein each of the cartridge assembly and the anvil assembly includes:
   a distal pair of recesses formed in a respective side edge thereof; and
   a proximal pair of recesses formed in a respective side edge thereof; and
   wherein a suture extends across respective distal and proximal pairs of recesses of the cartridge assembly and the anvil assembly for securing a respective surgical buttress thereto.

3. The Surgical apparatus according to claim 2, wherein a knife blade is supported in a distal end portion of each of the cartridge assembly and the anvil assembly.

4. The surgical apparatus according to claim 1, wherein the axial drive assembly moves the knife blade from the position proximal of the pair of recesses to the position distal of the pair of recesses.

5. The surgical apparatus according to claim 1, wherein the anchor is a suture.

6. The surgical apparatus according to claim 1, wherein the surgical buttress is pre-loaded onto the at least one of the cartridge assembly and the anvil assembly by the manufacturer before use.

7. A surgical apparatus of the type including a handle assembly operable with a drive assembly to eject at least one staple from the surgical apparatus, the surgical apparatus comprising:
   a cartridge assembly defining a tissue contacting surface and a longitudinally extending elongate slot;
   an anvil assembly defining a tissue contacting surface and a longitudinally extending elongate slot;
   wherein each of the cartridge assembly and the anvil assembly includes:
      a distal pair of recesses formed in a respective side edge thereof; and
      a proximal pair of recesses formed in a respective side edge thereof; and
      wherein a suture extends across respective distal and proximal pairs of recesses of the cartridge assembly and the anvil assembly for securing a respective surgical buttress thereto; and
   a surgical buttress releasably secured to at least one of the tissue contacting surface of the cartridge assembly and the tissue contacting surface of the anvil assembly by at least one anchor, wherein
   at least one of the cartridge assembly and the anvil assembly including:
      a pair of recesses formed in a respective side edge thereof, wherein the anchor extends from one of the pair of recesses to the other of the pair of recesses for securing the surgical buttress thereto,
      a knife blade pivotably mounted on the at least one of the cartridge assembly and the anvil assembly, the knife blade having a distally oriented knife edge and being movable from a position proximal of the pair of recesses to a position distal of the pair of recesses upon an actuation of the axial drive assembly, the knife being movable to cut the anchor.

8. The surgical apparatus according to claim 7, further comprising an axial drive assembly movable for firing surgical staples from the cartridge assembly.

9. The surgical apparatus according to claim 8, wherein the axial drive assembly has a central knife blade slidably disposable in the longitudinal extending elongate slot of the cartridge assembly and the anvil assembly.

10. The surgical apparatus according to claim 7, wherein a knife blade is supported in a distal end portion of each of the cartridge assembly and the anvil assembly.

11. The surgical apparatus according to claim 8, wherein the axial drive assembly moves the knife blade from the position proximal of the pair of recesses to the position distal of the pair of recesses.

12. The surgical apparatus according to claim 7, wherein the anchor is a suture.

13. The surgical apparatus according to claim 7, wherein the surgical buttress is pre-loaded onto the at least one of the cartridge assembly and the anvil assembly by the manufacturer before use.

14. A surgical apparatus of the type including a handle assembly operable with a drive assembly to eject at least one staple from the surgical apparatus, the surgical apparatus comprising:
 a cartridge assembly defining a tissue contacting surface and a longitudinally extending elongate slot;
 an anvil assembly defining a tissue contacting surface and a longitudinally extending elongate slot;
 a surgical buttress releasably secured to at least one of the tissue contacting surface of the cartridge assembly and the tissue contacting surface of the anvil assembly by at least one anchor, the anchor being a suture,
 at least one of the cartridge assembly and the anvil assembly including:
  a pair of recesses formed in a respective side edge thereof,
  wherein the anchor extends across the pair of recesses of the at least one of the cartridge assembly and the anvil assembly for securing the surgical buttress thereto,
  a knife blade pivotably mounted on the at least one of the cartridge assembly and the anvil assembly, the knife blade having a distally oriented knife edge and being movable from a position proximal of the pair of recesses to a position distal of the pair of recesses upon an actuation of the axial drive assembly, the knife being movable to cut the anchor.

15. The surgical apparatus according to claim 14, further comprising an axial drive assembly movable for firing surgical staples from the cartridge assembly.

16. The surgical apparatus according to claim 15, wherein the axial drive assembly has a central knife blade slidably disposable in the longitudinal extending elongate slot of the cartridge assembly and the anvil assembly.

17. The surgical apparatus according to claim 15, wherein the axial drive assembly moves the knife blade from the position proximal of the pair of recesses to the position distal of the pair of recesses.

18. The surgical apparatus according to claim 14, wherein each of the cartridge assembly and the anvil assembly includes:
 a distal pair of recesses formed in a respective side edge thereof; and
 a proximal pair of recesses formed in a respective side edge thereof; and
 wherein a suture extends across respective distal and proximal pairs of recesses of the cartridge assembly and the anvil assembly for securing a respective surgical buttress thereto.

19. The surgical apparatus according to claim 18, wherein a knife blade is supported in a distal end portion of each of the cartridge assembly and the anvil assembly.

20. The surgical apparatus according to claim 14, wherein the surgical buttress is pre-loaded onto the at least one of the cartridge assembly and the anvil assembly by the manufacturer before use.

\* \* \* \* \*